(12) United States Patent
Mitsudera et al.

(10) Patent No.: US 7,846,956 B2
(45) Date of Patent: Dec. 7, 2010

(54) MALONONITRILE COMPOUND AS PESTICIDES

(75) Inventors: Hiromasa Mitsudera, Toyonaka (JP); Ken Otaka, Iwaki (JP); Jun Fujiwara, Ashiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1187 days.

(21) Appl. No.: 10/585,478

(22) PCT Filed: Jan. 13, 2005

(86) PCT No.: PCT/JP2005/000629

§ 371 (c)(1),
(2), (4) Date: Jul. 7, 2006

(87) PCT Pub. No.: WO2005/068432

PCT Pub. Date: Jul. 28, 2005

(65) Prior Publication Data

US 2009/0149425 A1    Jun. 11, 2009

(30) Foreign Application Priority Data

Jan. 16, 2004   (JP)   ............................. 2004-009149

(51) Int. Cl.
| | |
|---|---|
| C07D 277/30 | (2006.01) |
| C07D 275/02 | (2006.01) |
| C07D 285/04 | (2006.01) |
| C07D 271/06 | (2006.01) |
| C07D 271/10 | (2006.01) |
| C07D 263/32 | (2006.01) |
| C07D 261/08 | (2006.01) |
| C07D 233/64 | (2006.01) |
| C07D 231/12 | (2006.01) |
| A61K 31/433 | (2006.01) |
| A61K 31/426 | (2006.01) |
| A61K 31/425 | (2006.01) |
| A61K 31/4245 | (2006.01) |
| A61K 31/421 | (2006.01) |
| A61K 31/42 | (2006.01) |
| A61K 31/4164 | (2006.01) |
| A61K 31/415 | (2006.01) |

(52) U.S. Cl. ....................... 514/378; 514/361; 514/364; 514/365; 514/372; 514/374; 514/396; 514/406; 548/128; 548/131; 548/143; 548/202; 548/214; 548/236; 548/247; 548/337.1; 548/375.1

(58) Field of Classification Search .................. 514/378, 514/361, 364, 365, 372, 374, 396, 406; 548/128, 548/131, 143, 202, 214, 236, 247, 337.1, 548/375.1

See application file for complete search history.

(56) References Cited

U.S. PATENT DOCUMENTS

| | | | |
|---|---|---|---|
| 6,663,860 B1 * | 12/2003 | Tvedten | .................... 424/94.63 |
| 2004/0138065 A1 | 7/2004 | Otaka et al. | |
| 2004/0142821 A1 | 7/2004 | Otaka et al. | |
| 2004/0143007 A1 | 7/2004 | Otaka et al. | |

FOREIGN PATENT DOCUMENTS

| | | | |
|---|---|---|---|
| JP | 11171702 A | * | 6/1999 |
| WO | 2002/089579 | | 11/2002 |
| WO | 2002/090320 | | 11/2002 |
| WO | 2002/090321 | | 11/2002 |
| WO | 2004/006677 | | 1/2004 |
| WO | 2004/020399 | | 3/2004 |

OTHER PUBLICATIONS

International Plant Protection Convention (29th Session of the FAO Conference, Nov. 1997).*
Hamilton and Crossley (Pesticide Residues in Food and Drinking Water, John Wiley & Sons, Ltd. 2004, p. 2).*
Patent Abstracts of Japan, vol. 1998, No. 6, JP 10-029966, Feb. 3, 1998.
Patent Abstracts of Japan, vol. 2003, No. 12, JP 2004-099597, Apr. 2, 2004.

* cited by examiner

*Primary Examiner*—Rebecca L Anderson
*Assistant Examiner*—Matthew P Coughlin
(74) *Attorney, Agent, or Firm*—Wenderoth, Lind & Ponack, L.L.P.

(57) ABSTRACT

The present invention provides a malononitrile compound represented by the formula (I): wherein any one of $X^1$, $X^2$, $X^3$ and $X^4$ is $CR^{100}$, wherein $R^{100}$ is a group represented by the formula: the other three of $X^1$, $X^2$, $X^3$ and $X^4$ each represent nitrogen or $CR^5$, provided that 1 to 3 of $X^1$, $X^2$, $X^3$ and $X^4$ represent nitrogen, and Z represents oxygen, sulfur or $NR^6$, which has pest-controlling activity.

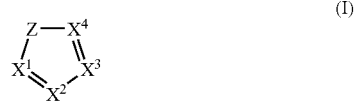

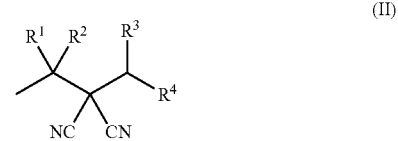

22 Claims, No Drawings

MALONONITRILE COMPOUND AS PESTICIDES

TECHNICAL FIELD

The present invention relates to a malononitrile compound and a use thereof.

BACKGROUND ART

For controlling pests, compounds having pest-controlling efficacy have been developed and put into practice.

DISCLOSURE OF INVENTION

An object of the present invention is to provide a compound having an excellent controlling effect on a pest, a pesticidal composition comprising the compound as an active ingredient, and a method for controlling a pest by using the compound.

The present invention relates to a malononitrile compound represented by the formula (I):

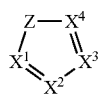

(I)

wherein any one of $X^1$, $X^2$, $X^3$ and $X^4$ is $CR^{100}$, (wherein $R^{100}$ represents a group represented by the formula:

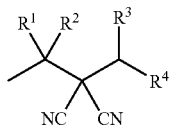

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen), the other three of $X^1$, $X^2$, $X^3$ and $X^4$ each represent nitrogen or $CR^5$, provided that one to three of $X^1$, $X^2$, $X^3$ and $X^4$ represent nitrogen, Z represents oxygen, sulfur or $NR^6$, $R^5$ independently represents halogen, cyano, nitro, hydroxyl, mercapto, formyl, $SF_5$, carboxyl, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, C2-C5 alkoxycarbonyl optionally substituted with one or more halogen, a group represented by $NR^{10}R^{11}$, a group represented by $C(=X^5)NR^{12}R^{13}$, a group represented by $(CH_2)_mQ$, a group represented by $C(=NOR^{17})R^{18}$, a group represented by $C(OR^{19})R^{20}R^{21}$, or hydrogen, $R^6$ represents C1-C5 alkyl optionally substituted with one or more halogen, C3-C5 alkenyl optionally substituted with one or more halogen, C3-C5 alkynyl optionally substituted with one or more halogen, C3-C6 cycloalkyl optionally substituted with one or more halogen, (C1-C5 alkoxy optionally substituted with one or more halogen) C1-C3 alkyl, C1-C5 alkylsulfinyl optionally substituted with one or more halogen, C1-C5 alkylsulfonyl optionally substituted with one or more halogen, C2-C6 alkylcarbonyl optionally substituted with one or more halogen, C2-C5 alkoxycarbonyl optionally substituted with one or more halogen, a group represented by $C(=X^5)NR^{12}R^{13}$, a group represented by $(CH_2)_mQ$, or hydrogen, and when two $CR^5$, or $CR^5$ and $NR^6$ are adjacent to each other, they may be taken together to represent C2-C6 alkanediyl or C4-C6 alkenediyl optionally substituted with one or more halogen, in which at least one methylene group forming the alkanediyl or the alkenediyl may be substituted with oxygen, sulfur or $NR^7$, $R^7$ represents C1-C5 alkyl optionally substituted with one or more halogen, C3-C5 alkenyl optionally substituted with one or more halogen, C3-C5 alkynyl optionally substituted with one or more halogen, C3-C6 cycloalkyl optionally substituted with one or more halogen, C2-C6 alkylcarbonyl optionally substituted with one or more halogen, C2-C5 alkoxycarbonyl optionally substituted with one or more halogen, or hydrogen, $R^{10}$ and $R^{11}$ each represent C1-C5 alkyl optionally substituted with one or more halogen, C3-C5 alkenyl optionally substituted with one or more halogen, C3-C5 alkynyl optionally substituted with one or more halogen, C3-C6 cycloalkyl optionally substituted with one or more halogen, (C1-C5 alkoxy optionally substituted with one or more halogen) C1-C3 alkyl, C1-C5 alkylsulfinyl optionally substituted with one or more halogen, C1-C5 alkylsulfonyl optionally substituted with one or more halogen, C2-C6 alkylcarbonyl optionally substituted with one or more halogen, C2-C5 alkoxycarbonyl optionally substituted with one or more halogen, or hydrogen, or the group represented by $NR^{10}R^{11}$ is 1-pyrrolyl, $R^{12}$ and $R^{13}$ each represent C1-C5 alkyl optionally substituted with one or more halogen, C3-C5 alkenyl optionally substituted with one or more halogen, C3-C5 alkynyl optionally substituted with one or more halogen, C3-C6 cycloalkyl optionally substituted with one or more halogen, a group represented by $(CH_2)_mQ$, or hydrogen, or $R^{12}$ and $R^{13}$ are taken together to represent C2-C6 alkanediyl optionally substituted with one or more halogen or C4-C6 alkenediyl optionally substituted with one or more halogen, $R^{17}$ and $R^{18}$ each represent C1-C5 alkyl optionally substituted with one or more halogen, C3-C5 alkenyl optionally substituted with one or more halogen, C3-C5 alkynyl optionally substituted with one or more halogen, C3-C6 cycloalkyl optionally substituted with one or more halogen, a group represented by $(CH_2)_mQ$, or hydrogen, $R^{19}$ represents C1-C5 alkyl optionally substituted with one or more halogen, C3-C5 alkenyl optionally substituted with one or more halogen, C3-C5 alkynyl optionally substituted with one or more halogen, C3-C6 cycloalkyl optionally substituted with one or more halogen, (C1-C5 alkoxy optionally substituted with one or more halogen) C1-C3 alkyl, C1-C5 alkylsulfinyl optionally substituted with one or more halogen, C1-C5 alkylsulfonyl optionally substituted with one or more halogen, C2-C6 alkylcarbonyl optionally substituted with one or more halogen, C2-C5 alkoxycarbonyl optionally substituted with one or more halogen, a group represented by $C(=X^5)NR^{12}R^{13}$, a group represented by $(CH_2)_mQ$, trialkylsilyl, or hydrogen, $R^{20}$ and $R^{21}$ each represent C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen, or hydrogen, Q represents aryl optionally substituted with $R^{14}$ n times, $R^{14}$ independently represents C1-C5 alkyl optionally substituted with one or more halogen, C3-C6 cycloalkyl optionally substituted with one or more halogen, C1-C5 alkoxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, C2-C5 alkoxycarbonyl optionally substituted with one or more halogen, or halogen, m and n each represent an integer of 0 to 5, and $X^5$ represents oxygen or sulfur (hereinafter, referred to as the present compound); a pesticidal composition comprising an effective amount of the present compound and an inert carrier, and a method for controlling a pest comprising applying an effective amount of the present compound to said pest or a place where said pest inhabits.

MODE FOR CARRYING OUT THE INVENTION

In the present invention, the "alkanediyl" represents a chain saturated hydrocarbon group in which two different constituting carbon atoms have a free valence. The "alkenediyl" represents a chain hydrocarbon group having one or two double bonds in which two different constituting carbon atoms have a free valence.

In the present invention, the "fluoroalkyl" represents alkyl substituted with one or two fluorine atoms. The description of C1-C6 or the like means the total number of carbon atoms constituting a substituent.

In the present invention, examples of the C1-C5 alkyl optionally substituted with one or more halogen represented by $R^1$ or $R^2$ include C1-C3 alkyl optionally substituted with one or more halogen; specifically, methyl, ethyl, propyl, 1-methylethyl, 2,2-dimethylpropyl, chloromethyl, fluoromethyl, difluoromethyl, trifluoromethyl, 2,2,2-trifluoroethyl and a 1,1,2,2-tetrafluoroethyl; and 1,1-diemethylethyl.

Examples of the C2-C5 alkenyl optionally substituted with one or more halogen include vinyl, 2,2-difluorovinyl, 1,2,2-trifluorovinyl, 1-propenyl and 2-propenyl.

Examples of the C2-C5 alkynyl optionally substituted with one or more halogen include ethynyl, 1-propynyl, 2-propynyl and 3,3,3-trifluoro-1-propynyl.

Examples of the C1-C5 alkoxy optionally substituted with one or more halogen represented by $R^2$ include C1-C3 alkyl optionally substituted with one or more halogen, such as methoxy, ethoxy, 1-methylethoxy, fluoromethoxy, difluoromethoxy, trifluoromethoxy, 2,2,2-trifluoroethoxy and 1,1,2,2-tetrafluoroethoxy; and butoxy.

Examples of the C1-C5 alkyl optionally substituted with one or more halogen represented by $R^3$ or $R^4$ include methyl, ethyl, 1-methylethyl, 2-methylpropyl, propyl, butyl, 3-methylbutyl, 2,2-dimethylpropyl, fluoromethyl, chloromethyl, 2,2-difluoroethyl, 2,2-dichloroethyl, 3,3-difluoropropyl, 3,3-dichloropropyl, trifluoromethyl, trichloromethyl, 2,2,2-trifluoroethyl, 2,2,2-trichloroethyl, 3,3,3-trifluoropropyl, 3,3,3-trichloropropyl, 2,2-difluoropropyl, 3,3-difluorobutyl, 1-bromo-2,2,2-trifluoroethyl, 1-chloro-2,2,2-trifluoroethyl, 1,2,2,2-tetrafluoroethyl, pentafluoroethyl, 2,2,3,3,3-pentafluoropropyl, 1,1,2,2-tetrafluoroethyl and 2,2,3,3-tetrafluoropropyl.

Examples of the C2-C5 alkenyl optionally substituted with one or more halogen include vinyl, allyl, 1-propenyl, 3-butenyl, 2-methyl-1-propenyl, 3-methyl-2-butenyl, 3-pentenyl, 4-pentenyl, 3-methyl-3-butenyl, 4-methyl-3-pentenyl, 1-chlorovinyl, 2-chlorovinyl, 1-fluorovinyl, 2-fluorovinyl, 2,2-dichlorovinyl, 2,2-dibromovinyl, 2,2-difluorovinyl, 1,2,2-trifluorovinyl, 1-(trifluoromethyl) vinyl, 2-chloro-2-propenyl, 3-chloro-2-propenyl, 2-fluoro-2-propenyl, 3-fluoro-2-propenyl, 3,3-dichloro-2-propenyl, 3,3-dibromo-2-propenyl, 3,3-difluoro-2-propenyl, 2,3,3-trifluoro-2-propenyl, 2-(trifluoromethyl)-2-propenyl, 2,3,3,3-tetrafluoro-1-propenyl, 1,2,3,3,3-pentafluoro-1-propenyl, 3,4,4-trifluoro-3-butenyl, 3,4,4,4-tetrafluoro-2-butenyl, 2,3,4,4,4-pentafluoro-2-butenyl and 4,5,5-trifluoro-4-pentenyl.

Examples of the C2-C5 alkynyl optionally substituted with one or more halogen include ethynyl, 1-propynyl, 2-propynyl, 1-butynyl, 3-methyl-1-butynyl, 3-chloro-2-propynyl, 3,3,3-trifluoro-1-propynyl and 4,4,4-trifluoro-2-butynyl.

Examples of the C3-C5 cycloalkyl optionally substituted with one or more halogen include cyclopropyl, 2,2-dichlorocyclopropyl, 2,2-difluorocyclopropyl, 2,2,3,3-tetrafluorocyclopropyl, 2,2-dichlorocyclobutyl, 2,2-difluorocyclobutyl, 2,2,3,3-tetrafluorocyclobutyl, cyclobutyl, cyclopentyl and cyclohexyl.

Examples of the C4-C5 cycloalkenyl optionally substituted with one or more halogen include 2-fluoro-2-cyclopentenyl.

Examples of the C2-C6 alkanediyl optionally substituted with one or more halogen represented by $R^3$ and $R^4$ together include ethylene, propylene, trimethylene and tetramethylene.

Examples of the C4-C6 alkenediyl optionally substituted with one or more halogen include 2-butynylene and 2-pentenylene.

Examples of the halogen represented by $R^5$ or $R^{14}$ include fluorine, chlorine, bromine and iodine.

Examples of the C1-C5 alkyl optionally substituted with one or more halogen represented by $R^5$, $R^6$, $R^7$, $R^{10}$, $R^{11}$, $R^{12}$, $R^{13}$, $R^{14}$, $R^{17}$, $R^{18}$, $R^{19}$, $R^{20}$ or $R^{21}$ include methyl, ethyl, 1-methylethyl, 1-ethylethyl, 1,1-dimethylethyl, propyl, 1-methylpropyl, 1-ethylpropyl, 1,1-dimethylpropyl, 2,2-dimethylpropyl, 1,2-dimethylpropyl, 1,1,2-trimethylpropyl, butyl, 1-methylbutyl, 2-methylbutyl, 3-methylbutyl, pentyl, fluoromethyl, chloromethyl, bromomethyl, iodomethyl, difluoromethyl, chlorodifluoromethyl, bromodifluoromethyl, trifluoromethyl, dichloromethyl, trichloromethyl, 1-chloroethyl, 1-bromoethyl, 1-iodoethyl, 1-fluoroethyl, 2-chloroethyl, 2-bromoethyl, 2-iodoethyl, 2-fluoroethyl, 2,2-difluoroethyl, 2,2,2-trifluoroethyl, 2,2,2-trichloroethyl, pentafluoroethyl, 2,2,2-trifluoro-1-chloroethyl, 3-fluoropropyl, 3-chloropropyl, 1-fluoro-1-methylethyl, 1-chloro-1-methylethyl, 1-bromo-1-methylethyl, 2-chloro-1,1-dimethylethyl, 1,1-difluoroethyl, 2-fluoro-1,1-dimethylethyl, heptafluoropropyl, 1,1,2,2,3,3-hexafluoropropyl, 4-chlorobutyl, 4-fluorobutyl, 5-chloropentyl and 5-fluoropentyl.

Examples of the C2-C5 alkenyl optionally substituted with one or more halogen represented by $R^5$, $R^{20}$ or $R^{21}$ include vinyl, 1-methylvinyl, 1-propenyl, 1-methyl-1-propenyl, 2-methyl-1-propenyl, 1,2-dimethyl-1-propenyl, 2-propenyl, 1-methyl-2-propenyl, 2-methyl-2-propenyl, 1,1-dimethyl-2-propenyl, 1,2-dimethyl-2-propenyl, 2,2-difluorovinyl, 2-chloro-2-propenyl, 2,2-dichloro-2-propenyl, 2-bromo-2-propenyl, 2,2-dibromo-2-propenyl and 2-fluoro-2-propenyl.

Examples of the C3-C5 alkenyl optionally substituted with one or more halogen represented by $R^6$, $R^7$, $R^{10}$, $R^{11}$, $R^{12}$, $R^{13}$, $R^{17}$, $R^{18}$ or $R^{19}$ include 2-propenyl, 1-methyl-2-propenyl, 2-methyl-2-propenyl, 1,1-dimethyl-2-propenyl, 1,2-dimethyl-2-propenyl, 2-chloro-2-propenyl, 2,2-dichloro-2-propenyl, 2-bromo-2-propenyl, 2,2-dibromo-2-propenyl, 2-fluoro-2-propenyl and 2,2-difluoro-2-propenyl.

Examples of the C2-C5 alkynyl optionally substituted with one or more halogen represented by $R^5$, $R^{20}$ or $R^{21}$ include ethynyl, 1-propynyl, 2-propynyl and 3,3,3-trifluoro-1-propynyl.

Examples of the C3-C5 alkynyl optionally substituted with one or more halogen represented by $R^6$, $R^7$, $R^{10}$, $R^{11}$, $R^{12}$, $R^{13}$, $R^{17}$, $R^{18}$ or $R^{19}$ include 1-propynyl, 2-propynyl and 3,3,3-trifluoro-1-propynyl.

Examples of the C3-C6 cycloalkyl optionally substituted with halogen or C1-C3 alkyl represented by $R^5$ include cyclopropyl, 1-methylcyclopropyl, 2,2-dichlorocyclopropyl, 2,2-dichloro-1-methylcyclopropyl, 2,2-difluorocyclopropyl, 2,2-difluoro-1-methylcyclopropyl, cyclobutyl, cyclopentyl and cyclohexyl.

Examples of the C3-C6 cycloalkyl optionally substituted with one or more halogen represented by $R^6$, $R^7$, $R^{10}$, $R^{11}$, $R^{12}$, $R^{13}$, $R^{14}$, $R^{17}$, $R^{18}$, $R^{19}$, $R^{20}$ or $R^{21}$ include cyclopropyl, 2,2-dichlorocyclopropyl, 2,2-difluorocyclopropyl, cyclobutyl, cyclopentyl and cyclohexyl.

Examples of the C1-C5 alkoxy optionally substituted with one or more halogen represented by $R^5$ or $R^{14}$ include methoxy, ethoxy, propoxy, trifluoromethoxy, bromodifluoromethoxy, difluoromethoxy, fluoromethoxy, chlorodifluoromethoxy, pentafluoroethoxy, 2,2,2-trifluoroethoxy and 1,1,2,2-tetrafluoroethoxy.

Examples of the C3-C6 alkenyloxy optionally substituted with one or more halogen represented by $R^5$ include 1-propenyloxy, 2-propenyloxy and 2,2-difluoro-2-propenyloxy.

Examples of the C3-C6 alkynyloxy optionally substituted with one or more halogen represented by $R^5$ include 2-propynyloxy and 2-butynyloxy.

Examples of the (C1-C5 alkoxy optionally substituted with one or more halogen) C1-C3 alkyl represented by $R^6$, $R^{10}$, $R^{11}$ or $R^{19}$ include methoxymethyl, ethoxymethyl, 1-methoxyethyl, 1-ethoxyethyl and trifluoromethoxymethyl.

Examples of the C1-C5 alkylthio optionally substituted with one or more halogen represented by $R^5$ or $R^{14}$ include methylthio, ethylthio, trifluoromethylthio, chlorodifluoromethylthio, bromodifluoromethylthio, dibromofluoromethylthio, 2,2,2-trifluoroethylthio, 1,1,2,2-tetrafluoroethylthio and pentafluoroethylthio.

Examples of the C3-C5 alkenylthio optionally substituted with one or more halogen represented by $R^5$ or $R^{14}$ include 2-propenylthio and 2,2-difluoro-2-propenylthio.

Examples of the C3-C5 alkynylthio optionally substituted with one or more halogen represented by $R^5$ or $R^{14}$ include 2-propynylthio, 2-butynylthio and 3,3,3-trifluoro-1-propynyl.

Examples of the C1-C5 alkylsulfinyl optionally substituted with one or more halogen represented by $R^5$, $R^6$, $R^{10}$, $R^{11}$ or $R^{14}$ include methylsulfinyl, ethylsulfinyl and trifluoromethylsulfinyl.

Examples of the C1-C5 alkylsulfonyl optionally substituted with one or more halogen represented by $R^5$, $R^6$, $R^{10}$, $R^{11}$, $R^{14}$ or $R^{19}$ include methylsulfonyl and trifluoromethylsulfonyl.

Examples of the C2-C6 alkylcarbonyl optionally substituted with one or more halogen represented by $R^5$, $R^6$, $R^7$, $R^{10}$, $R^{11}$, $R^{14}$ or $R^{19}$ include acetyl, propionyl, 2,2-dimethylpropionyl and trifluoroacetyl.

Examples of the C2-C5 alkoxycarbonyl represented by $R^5$, $R^6$, $R^7$, $R^{10}$, $R^{11}$, $R^{14}$ or $R^{19}$ include methoxycarbonyl, ethoxycarbonyl, 1-methylethoxycarbonyl and t-butoxycarbonyl.

Examples of the trialkylsilyl represented by $R^{19}$ include trimethylsilyl, triisopropylsilyl and t-butyldimethylsilyl.

Examples of the C2-C6 alkanediyl optionally substituted with one or more halogen represented by two $CR^5$ or $CR^5$ and $NR^6$ together include propylene, trimethylene, tetramethylene, ethyleneoxy, dimethyleneoxy, ethylenethio and dimethylenethio.

Examples of the C4-C6 alkenediyl optionally substituted with one or more halogen include 2-butenylene and 2-pentenylene.

Examples of the C2-C6 alkanediyl optionally substituted with one or more halogen represented by $R^{12}$ and $R^{13}$ together include ethylene, propylene, trimethylene and tetramethylene.

Examples of the C4-C6 alkenediyl optionally substituted with one or more halogen include 2-butenylene and 2-pentenylene.

Examples of the group represented by $C(OR^{19})R^{20}R^{21}$ include 1-hydroxy-1-methylethyl, 1-methyl-1-methoxyethyl and 1-methyl-1-propargyloxyethyl.

Aspects of the present compound include the following compounds:

a malononitrile compound of the formula (I) in which $R^1$ is hydrogen;

a malononitrile compound of the formula (I) in which $R^2$ is methyl;

a malononitrile compound of the formula (I) in which $R^1$ and $R^2$ are hydrogen;

a malononitrile compound of the formula (I) in which $R^1$ is hydrogen and $R^2$ is methyl;

a malononitrile compound of the formula (I) in which $R^1$ is C1-C3 alkyl optionally substituted with one or more halogen or hydrogen, and $R^2$ is C1-C3 alkyl optionally substituted with one or more halogen, C2-C5 alkenyl optionally substituted with one or more halogen, C2-C5 alkynyl optionally substituted with one or more halogen, hydrogen or cyano;

a malononitrile compound of the formula (I) in which $R^1$ is hydrogen and $R^2$ is C1-C3 alkyl optionally substituted with one or more halogen or hydrogen;

a malononitrile compound of the formula (I) in which $R^3$ is hydrogen;

a malononitrile compound of the formula (I) in which $R^4$ is C2-C5 alkenyl optionally substituted with one or more halogen;

a malononitrile compound of the formula (I) in which $R^4$ is vinyl;

a malononitrile compound of the formula (I) in which $R^4$ is 2-propenyl;

a malononitrile compound of the formula (I) in which $R^4$ is 2,2-difluorovinyl;

a malononitrile compound of the formula (I) in which $R^4$ is 1-(trifluoromethyl)vinyl;

a malononitrile compound of the formula (I) in which $R^4$ is 3,3-difluoro-2-propenyl;

a malononitrile compound of the formula (I) in which $R^4$ is 2,3,3-trifluoro-2-propenyl;

a malononitrile compound of the formula (I) in which $R^4$ is 3,3,3-trifluoro-1-propenyl;

a malononitrile compound of the formula (I) in which $R^4$ is C2-C5 alkynyl optionally substituted with one or more halogen;

a malononitrile compound of the formula (I) in which $R^4$ is C1-C5 fluoroalkyl;

a malononitrile compound of the formula (I) in which $R^4$ is fluoromethyl;

a malononitrile compound of the formula (I) in which $R^4$ is 2,2-difluoroethyl;

a malononitrile compound of the formula (I) in which $R^4$ is 2,2,2-trifluoroethyl;

a malononitrile compound of the formula (I) in which $R^4$ is pentafluoroethyl;

a malononitrile compound of the formula (I) in which $R^4$ is 3,3,3-trifluoropropyl;

a malononitrile compound of the formula (I) in which $R^4$ is 2,2,3,3,3-pentafluoropropyl;

a malononitrile compound of the formula (I) in which $R^4$ is C3-C6 cycloalkyl optionally substituted with one or more halogen;

a malononitrile compound of the formula (I) in which $R^4$ is 2,2-dichlorocyclopropyl;

a malononitrile compound of the formula (I) in which $R^4$ is cyclopropyl;

a malononitrile compound of the formula (I) in which $R^4$ is cyclobutyl;

a malononitrile compound of the formula (I) in which $R^3$ and $R^4$ each represent C1-C3 alkyl optionally substituted with one or more halogen, C2-C5 alkenyl optionally substituted with one or more halogen, C2-C3 alkynyl optionally substituted with one or more halogen, C3-C5 cycloalkyl optionally substituted with one or more halogen or hydrogen, or $R^3$ and $R^4$ are taken together to represent C2-C6 alkanediyl optionally substituted with one or more halogen;

a malononitrile compound of the formula (I) in which $R^3$ is hydrogen, and $R^4$ represents C1-C3 alkyl optionally substituted with one or more halogen, C2-C5 alkenyl optionally substituted with halogen, or C2-C5 alkynyl optionally substituted with one or more halogen, or $R^3$ and $R^4$ are taken together to form C2-C6 alkanediyl optionally substituted halogen;

a malononitrile compound of the formula (I) in which $R^3$ is hydrogen, and $R^4$ is vinyl or 2-propenyl;

a malononitrile compound of the formula (I) in which $R^3$ is hydrogen, and $R^4$ is 2,2-difluorovinyl, 1-(trifluoromethyl)vinyl, 3,3-difluoro-2-propenyl, 2,3,3-trifluoro-2-propenyl or 3,3,3-trifluoro-1-propenyl;

a malononitrile compound of the formula (I) in which $R^3$ is hydrogen, and $R^4$ is fluoromethyl, 2,2-difluoroethyl, 2,2,2-trifluoroethyl, 1,1,1,2,2,2-pentafluoroethyl, 3,3,3-trifluoropropyl or 2,2,3,3,3-pentafluoropropyl;

a malononitrile compound of the formula (I) in which $R^3$ is hydrogen, and $R^4$ is cyclopropyl, cyclobutyl or 2,2-dichlorocyclopropyl;

a malononitrile compound of the formula (I) in which $R^1$, $R^2$ and $R^3$ are hydrogen, and $R^4$ is vinyl or 2-propenyl;

a malononitrile compound of the formula (I) in which $R^1$, $R^2$ and $R^3$ are hydrogen, and $R^4$ is 2,2-difluorovinyl, 1-(trifluoromethyl)vinyl, 3,3-difluoro-2-propenyl, 2,3,3-trifluoro-2-propenyl or 3,3,3-trifluoro-1-propenyl;

a malononitrile compound of the formula (I) in which $R^1$ and $R^3$ are hydrogen, $R^2$ is methyl, and $R^4$ is 2,2-difluorovinyl, 1-(trifluoromethyl)vinyl, 3,3-difluoro-2-propenyl, 2,3,3-trifluoro-2-propenyl or 3,3,3-trifluoro-1-propenyl;

a malononitrile compound of the formula (I) in which $R^1$, $R^2$ and $R^3$ are hydrogen, and $R^4$ is fluoromethyl, 2,2-difluoroethyl, 2,2,2-trifluoroethyl, pentafluoroethyl, 3,3,3-trifluoropropyl or 2,2,3,3,3-pentafluoropropyl;

a malononitrile compound of the formula (I) in which $R^1$ and $R^3$ are hydrogen, $R^2$ is methyl, and $R^4$ is fluoromethyl, 2,2-difluoroethyl, 2,2,2-trifluoroethyl, pentafluoroethyl, 3,3,3-trifluoropropyl or 2,2,3,3,3-pentafluoropropyl;

a malononitrile compound of the formula (I) in which $R^1$, $R^2$ and $R^3$ are hydrogen, and $R^4$ is cyclopropyl, cyclobutyl or 2,2-dichlorocyclopropyl;

a malononitrile compound of the formula (I) in which $R^1$ is hydrogen and $R^2$ is C1-C3 alkyl optionally substituted with one or more halogen or hydrogen;

a malononitrile compound of the formula (I) in which $R^1$ is C1-C3 alkyl optionally substituted with one or more halogen or hydrogen, and $R^2$ is C1-C3 alkyl optionally substituted with one or more halogen, C1-C3 alkoxy optionally substituted with one or more halogen, C2-C5 alkenyl optionally substituted with one or more halogen, C2-C5 alkynyl optionally substituted with one or more halogen, hydrogen or cyano;

a malononitrile compound of the formula (I) in which $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, or hydrogen, or $R^3$ and $R^4$ are taken together to form C2-C6 alkanediyl optionally substituted with one or more halogen;

a malononitrile compound of the formula (I) in which $R^3$ is hydrogen and $R^4$ is C1-C5 alkyl optionally substituted with one or more halogen, C2-C5 alkenyl optionally substituted with one or more halogen, C2-C5 alkynyl optionally substituted with one or more halogen, or $R^3$ and $R^4$ are taken together to form C2-C6 alkanediyl optionally substituted with one or more halogen;

a malononitrile compound of the formula (I) in which $R^1$ is hydrogen, $R^2$ is C1-C3 alkyl optionally substituted with one or more halogen or hydrogen, and $R^3$ and $R^4$ each represent C1-C3 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, or hydrogen, or $R^3$ and $R^4$ are taken together to form C2-C6 alkanediyl optionally substituted with one or more halogen;

a malononitrile compound of the formula (I) in which $R^1$ is C1-C3 alkyl optionally substituted with one or more halogen or hydrogen, $R^2$ is C1-C3 alkyl optionally substituted with one or more halogen, C1-C3 alkoxy optionally substituted with one or more halogen, C2-C5 alkenyl optionally substituted with one or more halogen, C2-C5 alkynyl optionally substituted with one or more halogen, hydrogen or cyano, and $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen or hydrogen, or $R^3$ and $R^4$ are taken together to form C2-C6 alkanediyl optionally substituted with one or more halogen;

a malononitrile compound of the formula (I) in which $R^1$ is hydrogen, $R^2$ is C1-C3 alkyl optionally substituted with one or more halogen, or hydrogen, and $R^3$ and $R^4$ each represent C1-C3 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, or hydrogen, or $R^3$ and $R^4$ are taken together to form C2-C6 alkanediyl optionally substituted with one or more halogen;

a malononitrile compound of the formula (I) in which $R^1$ is C1-C3 alkyl optionally substituted with one or more halogen, or hydrogen, $R^2$ is C1-C3 alkyl optionally substituted with one or more halogen, C1-C3 alkoxy optionally substituted with one or more halogen, C2-C5 alkenyl optionally substituted one or more halogen, C2-C5 alkynyl optionally substituted with one or more halogen, hydrogen or cyano, $R^3$ is hydrogen, and $R^4$ is C1-C5 alkyl optionally substituted with one or more halogen, C2-C5 alkenyl optionally substituted with one or more halogen or C2-C5 alkyl optionally substituted with one or more halogen, or $R^3$ and $R^4$ are taken together to form C2-C6 alkanediyl optionally substituted with one or more halogen;

a malononitrile compound of the formula (I) in which Z is $NR^6$, $X^1$ is nitrogen, and $X^2$, $X^3$ and $X^4$ each are $CR^5$;

a malononitrile compound of the formula (I) in which Z is oxygen, $X^1$ is nitrogen, and $X^2$, $X^3$ and $X^4$ each are $CR^5$;

a malononitrile compound of the formula (I) in which Z is sulfur, $X^1$ is nitrogen, and $X^2$, $X^3$ and $X^4$ each are $CR^5$;

a malononitrile compound of the formula (I) in which Z is $NR^6$, $X^2$ is nitrogen, and $X^1$, $X^3$ and $X^4$ each are $CR^5$;

a malononitrile compound of the formula (I) in which Z is oxygen, $X^2$ is nitrogen, and $X^1$, $X^3$ and $X^4$ each are $CR^5$;

a malononitrile compound of the formula (I) in which Z is sulfur, $X^2$ is nitrogen, and $X^1$, $X^3$ and $X^4$ each are $CR^5$;

a malononitrile compound of the formula (I) in which Z is $NR^6$, $X^1$ and $X^2$ are nitrogen, and $X^3$ and $X^4$ each are $CR^5$;

a malononitrile compound of the formula (I) in which Z is $NR^6$; $X^1$ and $X^3$ are nitrogen, and $X^2$ and $X^4$ each are $CR^5$;

a malononitrile compound of the formula (I) in which Z is oxygen, $X^1$ and $X^3$ are nitrogen, and $X^2$ and $X^4$ each are $CR^5$;

a malononitrile compound of the formula (I) in which Z is oxygen, $X^2$ and $X^3$ are nitrogen, and $X^1$ and $X^4$ each are $CR^5$;

a malononitrile compound of the formula (I) in which Z is sulfur, $X^1$ and $X^3$ are nitrogen, and $X^2$ and $X^4$ each are $CR^5$;

a malononitrile compound of the formula (I) in which Z is sulfur, $X^2$ and $X^3$ are nitrogen, and $X^1$ and $X^4$ each are $CR^5$;

a malononitrile compound of the formula (I) in which Z is $NR^6$, $X^1$, $X^2$ and $X^3$ are nitrogen, and $X^4$ is $CR^5$;

a malononitrile compound represented by the formula (I-i)

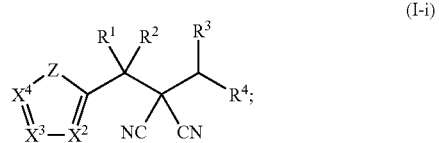

(I-i)

a malononitrile compound of the formula (I-i) in which any one of $X^3$ and $X^4$ is a carbon atom bound to ethyl;

a malononitrile compound of the formula (I-i) in which any one of $X^3$ and $X^4$ is a carbon atom bound to 1-methylethyl;

a malononitrile compound of the formula (I-i) in which any one of $X^3$ and $X^4$ is a carbon atom bound to 1,1-dimethylethyl;

a malononitrile compound of the formula (I-i) in which any one of $X^3$ and $X^4$ is a carbon atom bound to 2,2-dimethylpropyl;

a malononitrile compound of the formula (I-i) in which any one of $X^3$ and $X^4$ is a carbon atom bound to trifluoromethyl;

a malononitrile compound of the formula (I-i) in which any one of $X^3$ and $X^4$ is a carbon atom bound to pentafluoroethyl;

a malononitrile compound of the formula (I-i) in which any one of $X^3$ and $X^4$ is a carbon atom bound to 1-methylvinyl;

a malononitrile compound of the formula (I-i) in which any one of $X^3$ and $X^4$ is a carbon atom bound to ethynyl;

a malononitrile compound of the formula (I-i) in which any one of $X^3$ and $X^4$ is a carbon atom bound to cyclopropyl;

a malononitrile compound of the formula (I-i) in which any one of $X^3$ and $X^4$ is a carbon atom bound to 1-methylcyclopropyl;

a malononitrile compound of the formula (I-i) in which any one of $X^3$ and $X^4$ is a carbon atom bound to propargyloxy;

a malononitrile compound of the formula (I-i) in which any one of $X^3$ and $X^4$ is a carbon atom bound to 2-butynyloxy;

a malononitrile compound of the formula (I-i) in which any one of $X^3$ and $X^4$ is a carbon atom bound to 3-butynyloxy;

a malononitrile compound of the formula (I-i) in which any one of $X^3$ and $X^4$ is a carbon atom bound to methylthio a malononitrile compound of the formula (I-i) in which any one of $X^3$ and $X^4$ is a carbon atom bound to trifluoromethylthio;

a malononitrile compound of the formula (I-i) in which any one of $X^3$ and $X^4$ is a carbon atom bound to propargylthio;

a malononitrile compound of the formula (I-i) in which any one of $X^3$ and $X^4$ is a carbon atom bound to methylsulfinyl;

a malononitrile compound of the formula (I-i) in which any one of $X^3$ and $X^4$ is a carbon atom bound to trifluoromethylsulfynyl;

a malononitrile compound of the formula (I-i) in which any one of $X^3$ and $X^4$ is a carbon atom bound to methylsulfonyl;

a malononitrile compound of the formula (I-i) in which any one of $X^3$ and $X^4$ is a carbon atom bound to trifluoromethylsulfonyl;

a malononitrile compound of the formula (I-i) in which any one of $X^3$ and $X^4$ is a carbon atom bound to cyano;

a malononitrile compound of the formula (I-i) in which any one of $X^3$ and $X^4$ is a carbon atom bound to a bromine atom;

a malononitrile compound of the formula (I-i) in which any one of $X^3$ and $X^4$ is a carbon atom bound to a chlorine atom;

a malononitrile compound of the formula (I-i) in which any one of $X^3$ and $X^4$ is a carbon atom bound to a fluorine atom;

a malononitrile compound of the formula (I-i) in which any one of $X^3$ and $X^4$ is a carbon atom bound to nitro;

a malononitrile compound of the formula (I-i) in which $X^3$ is a carbon atom bound to halogen, cyano or nitro;

a malononitrile compound of the formula (I-i) in which $X^3$ is a carbon atom bound to C1-C5 alkylthio optionally substituted with one or more halogen, C1-C5 alkylsulfynyl optionally substituted with one or more halogen or C1-C5 alkylsulfonyl optionally substituted with one or more halogen;

a malononitrile compound of the formula (I-i) in which $X^3$ is a carbon atom bound to C1-C5 alkyl optionally substituted with one or more halogen, C2-C5 alkenyl optionally substituted with one or more halogen, C2-C5 alkynyl optionally substituted with one or more halogen or C3-C6 alkynyl optionally substituted with one or more halogen;

a malononitrile compound of the formula (I-i) in which $X^3$ is a carbon atom bound to C1-C5 alkoxy optionally substituted with one or more halogen, C3-C6 alkenyloxy optionally substituted with one or more halogen, C3-C6 alkynyloxy optionally substituted with one or more halogen or C3-C6 alkynyl optionally substituted with one or more halogen;

a malononitrile compound of the formula (I-i) in which $X^4$ is a carbon atom bound to halogen, cyano or nitro; a malononitrile compound of the formula (I-i) in which $X^4$ is a carbon atom bound to C1-C5 alkylthio optionally substituted with one or more halogen, C1-C5 alkylsulfinyl optionally substituted with one or more halogen or C1-C5 alkylsulfonyl optionally substituted with one or more halogen;

a malononitrile compound of the formula (I-i) in which $X^4$ is a carbon atom bound to C1-C5 alkyl optionally substituted with one or more halogen, C2-C5 alkenyl optionally substituted with one or more halogen, C2-C5 alkynyl optionally substituted with one or more halogen or C3-C6 alkynyl optionally substituted with one or more halogen;

a malononitrile compound of the formula (I-i) in which $X^4$ is a carbon atom bound to C1-C5 alkoxy optionally substituted with one or more halogen, C3-C6 alkenyloxy optionally substituted with one or more halogen, C3-C6 alkynyloxy optionally substituted with one or more halogen or C3-C6 alkynyl optionally substituted with one or more halogen;

a malononitrile compound represented by the formula (I-ii):

$$\begin{array}{c}\text{(I-ii)}\\ Z\diagup X^1\diagdown \overset{R^1}{\underset{}{\diagup}}\overset{R^2}{\underset{}{\diagdown}}\overset{R^3}{\underset{}{\diagup}}R^4;\\ X^4=X^3\quad NC\quad CN\end{array}$$

a malononitrile compound of the formula (I-ii) in which Z is $NR^6$ and $R^6$ is ethyl;

a malononitrile compound of the formula (I-ii) in which $X^4$ is a carbon atom bound to ethyl;

a malononitrile compound of the formula (I-ii) in which Z is $NR^6$ and $R^6$ is 1-methylethyl;

a malononitrile compound of the formula (I-ii) in which $X^4$ is a carbon atom bound to 1-methylethyl;

a malononitrile compound of the formula (I-ii) in which Z is $NR^6$ and $R^6$ is 1,1-dimethylethyl;

a malononitrile compound of the formula (I-ii) in which $X^4$ is a carbon atom bound to 1,1-dimethylethyl;

a malononitrile compound of the formula (I-ii) in which Z is $NR^6$ and $R^6$ is 2,2-dimethylpropyl;

a malononitrile compound of the formula (I-ii) in which $X^4$ is a carbon atom bound to 2,2-dimethylpropyl;

a malononitrile compound of the formula (I-ii) in which $X^4$ is a carbon atom bound to trifluoromethyl;

a malononitrile compound of the formula (I-ii) in which $X^4$ is a carbon atom bound to pentafluoroethyl;

a malononitrile compound of the formula (I-ii) in which $X^4$ is a carbon atom bound to 1-methylvinyl;

a malononitrile compound of the formula (I-ii) in which $X^4$ is a carbon atom bound to ethynyl;

a malononitrile compound of the formula (I-ii) in which Z is $NR^6$ and $R^6$ is 2-propargyl;

a malononitrile compound of the formula (I-ii) in which Z is $NR^6$ and $R^6$ is cyclopropyl;

a malononitrile compound of the formula (I-ii) in which $X^4$ is a carbon atom bound to cyclopropyl;

a malononitrile compound of the formula (I-ii) in which Z is $NR^6$ and $R^6$ is 1-methylcyclopropyl;

a malononitrile compound of the formula (I-ii) in which $X^4$ is a carbon atom bound to 1-methylcyclopropyl;

a malononitrile compound of the formula (I-ii) in which $X^4$ is a carbon atom bound to propargyloxy;

a malononitrile compound of the formula (I-ii) in which $X^4$ is a carbon atom bound to 2-butynyloxy;

a malononitrile compound of the formula (I-ii) in which $X^4$ is a carbon atom bound to 3-butynyloxy;

a malononitrile compound of the formula (I-ii) in which $X^4$ is a carbon atom bound to methylthio;

a malononitrile compound of the formula (I-ii) in which $X^4$ is a carbon atom bound to trifluoromethylthio;

a malononitrile compound of the formula (I-ii) in which $X^4$ is a carbon atom bound to propargylthio;

a malononitrile compound of the formula (I-ii) in which $X^4$ is a carbon atom bound to methylsulfinyl;

a malononitrile compound of the formula (I-ii) in which $X^4$ is a carbon atom bound to trifluoromethylsulfinyl;

a malononitrile compound of the formula (I-ii) in which $X^4$ is a carbon atom bound to methylsulfonyl;

a malononitrile compound of the formula (I-ii) in which $X^4$ is a carbon atom bound to trifluoromethylsulfonyl;

a malononitrile compound of the formula (I-ii) in which $X^4$ is a carbon atom bound to cyano;

a malononitrile compound of the formula (I-ii) in which $X^4$ is a carbon atom bound to a bromine atom;

a malononitrile compound of the formula (I-ii) in which $X^4$ is a carbon atom bound to a chlorine atom;

a malononitrile compound of the formula (I-ii) in which $X^4$ is a carbon atom bound to a fluorine atom;

a malononitrile compound of the formula (I-ii) in which $X^4$ is a carbon atom bound to nitro;

a malononitrile compound of the formula (I-ii) in which $X^4$ is a carbon atom bound to halogen, cyano or nitro;

a malononitrile compound of the formula (I-ii) in which $X^4$ is a carbon atom bound to C1-C5 alkylthio optionally substituted with one or more halogen, C1-C5 alkylsulfinyl optionally substituted with one or more halogen or C1-C5 alkylsulfonyl optionally substituted with one or more halogen;

a malononitrile compound of the formula (I-ii) in which $X^4$ is a carbon atom bound to C1-C5 alkyl optionally substituted with one or more halogen, C2-C5 alkenyl optionally substituted with one or more halogen, C2-C5 alkynyl optionally substituted with one or more halogen or C3-C6 alkynyl optionally substituted with one or more halogen;

a malononitrile compound of the formula (I-ii) in which $X^4$ is a carbon atom bound to C1-C5 alkoxy optionally substituted with one or more halogen, C3-C6 alkenyloxy optionally substituted with one or more halogen, C3-C6 alkynyloxy optionally substituted with one or more halogen or C3-C6 alkynyl optionally substituted with one or more halogen;

a malononitrile compound of the formula (I-ii) in which Z is $NR^6$ and $R^6$ is C1-C5 alkyl optionally substituted with one or more halogen, C3-C5 alkenyl optionally substituted with one or more halogen, C3-C5 alkynyl optionally substituted with one or more halogen or a C3-C6 cycloalkyl optionally substituted with one or more halogen;

a malononitrile compound represented by the formula (II-i):

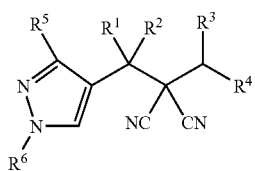

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen;

$R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen;

$R^5$ represent halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, $R^6$ represents C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-i) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, and $R^6$ is C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-i) in which $R^1$ and $R^2$ are hydrogen, $R^3$ is hydrogen, $R^4$ is C1-C5 alkyl optionally substituted with one or more halogen or C2-C5 alkenyl optionally substituted with one or more halogen, $R^5$ is C1-C5 alkyl optionally substituted with one or more halogen, and $R^6$ is C1-C5 alkyl optionally substituted with one or more halogen;

a malononitrile compound of the formula (II-i) in which $R^1$ and $R^2$ are hydrogen, $R^3$ is hydrogen, $R^4$ is 2,2,2-trifluoroethyl, $R^5$ is C1-C5 alkyl optionally substituted with one or more halogen, and $R^6$ is C1-C5 alkyl optionally substituted with one or more halogen;

a malononitrile compound represented by the formula (II-ii):

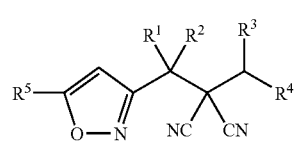

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen C2-C6 alkylcarbonyl optionally substituted with one or more halogen, a group represented by $C(OR^{19})R^{20}R^{21}$, or hydrogen, $R^{19}$ represents C1-C5 alkyl optionally, substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-ii) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-ii) in which $R^1$ and $R^2$ are hydrogen, $R^3$ is hydrogen, $R^4$ is C1-C5 alkyl optionally substituted with one or more halogen or C2-C5 alkenyl optionally substituted with one or more halogen, and $R^5$ is C1-C5 alkyl optionally substituted with one or more halogen;

a malononitrile compound of the formula (II-ii) in which $R^1$ and $R^2$ are hydrogen, $R^3$ is hydrogen, $R^4$ is 2,2,2-trifluoroethyl, and $R^5$ is C1-C5 alkyl optionally substituted with one or more halogen;

a compound represented by the formula (II-iii):

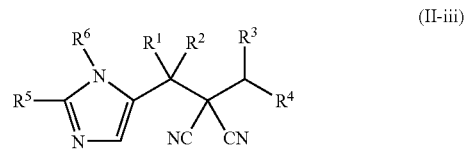

(II-iii)

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, and $R^6$ represents C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-iii) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally, substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^6$ is C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;
a malononitrile compound of the formula (II-iii) in which $R^1$ and $R^2$ are hydrogen, $R^3$ is hydrogen, $R^4$ is C1-C5 alkyl optionally substituted with one or more halogen or C2-C5 alkenyl optionally substituted with one or more halogen, $R^5$ is C1-C5 alkyl optionally substituted with one or more halogen, and $R^6$ is C1-C5 alkyl optionally substituted with one or more halogen;
a malononitrile compound of the formula (II-iii) in which $R^1$ and $R^2$ are hydrogen, $R^3$ is hydrogen, $R^4$ is 2,2,2-trifluoroethyl, $R^5$ is C1-C5 alkyl optionally substituted with one or more halogen, and $R^6$ is C1-C5 alkyl optionally substituted with one or more halogen;
a malononitrile compound represented by the formula (II-iv):

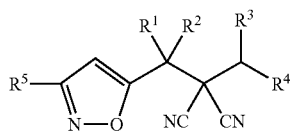

(II-iv)

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;
a malononitrile compound of the formula (II-iv) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;
a malononitrile compound of the formula (II-iv) in which $R^1$ and $R^2$ are hydrogen, R³ is hydrogen, R⁴ is C1-C5 alkyl optionally substituted with one or more halogen, or C2-C5 alkenyl optionally substituted with one or more halogen, and R⁵ is C1-C5 alkyl optionally substituted with one or more halogen;

a malononitrile compound of the formula (II-iv) in which R¹ and R² are hydrogen, R³ is hydrogen, R⁴ is 2,2,2-trifluoroethyl, and R⁵ is C1-C5 alkyl optionally substituted with one or more halogen;

a malononitrile compound represented by the formula (II-v):

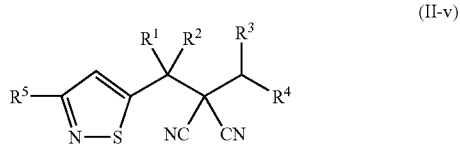

(II-v)

wherein R¹ represents C1-C5 alkyl optionally substituted with one or more halogen, C2-C5 alkenyl optionally substituted with one or more halogen, C2-C5 alkynyl optionally substituted with one or more halogen, or hydrogen, R² represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, R³ and R⁴ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or R³ and R⁴ are taken together to represent C2-C6 alkanediyl optionally substituted with one or more halogen or C4-C6 alkenediyl optionally substituted with one or more halogen, R⁵ represents halogen, cyano, nitro, formyl, SF₅, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by C(OR¹⁹)R²⁰R²¹, or hydrogen, R¹⁹ represents C1-C5 alkyl optionally substituted with one or more halogen, C3-C5 alkynyl optionally substituted with one or more halogen, or hydrogen, and R²⁰ and R²¹ each represent C1-C5 alkyl optionally substituted with one or more halogen, or hydrogen;

a malononitrile compound of the formula (II-v) in which R¹ is hydrogen,

R² is C1-C5 alkyl optionally substituted with one or more halogen, or hydrogen,

R³ and R⁴ each are C1-C5 alkyl optionally substituted with one or more halogen, C2-C5 alkenyl optionally substituted with one or more halogen, or hydrogen, R⁵ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by C(OR¹⁹)R²⁰R²¹, or hydrogen, R¹⁹ represents C1-C5 alkyl optionally substituted with one or more halogen, C3-C5 alkynyl optionally substituted with one or more halogen, or hydrogen, and R²⁰ and R²¹ each represent C1-C5 alkyl optionally substituted with one or more halogen, or hydrogen;

a malononitrile compound of the formula (II-v) in which R¹ and R² are hydrogen,

R³ is hydrogen,

R⁴ is C1-C5 alkyl optionally substituted with one or more halogen, or C2-C5 alkenyl optionally substituted with one or more halogen, and R⁵ is C1-C5 alkyl optionally substituted with one or more halogen;

a malononitrile compound of the formula (II-v) in which R¹ and R² are hydrogen,

R³ is hydrogen,

R⁴ is 2,2,2-trifluoroethyl, and

R⁵ is C1-C5 alkyl optionally substituted with one or more halogen;

a malononitrile compound represented by the formula (II-vi):

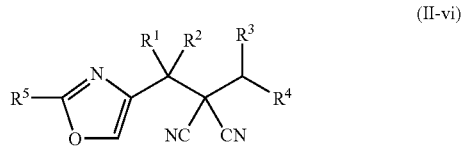

(II-vi)

wherein R¹ represents C1-C5 alkyl optionally substituted with one or more halogen, C2-C5 alkenyl optionally substituted with one or more halogen, C2-C5 alkynyl optionally substituted with one or more halogen, or hydrogen, R² represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-vi) in which $R^1$ is hydrogen, $R^2$ is C1-C5 alkyl optionally substituted with one or more halogen, or hydrogen, $R^3$ and $R^4$ each represent C1-C5 alkyl optionally substituted with one or more halogen, C2-C5 alkenyl optionally substituted with one or more halogen, or hydrogen, $R^5$ represents halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-vi) in which $R^1$ and $R^2$ are hydrogen, $R^3$ is hydrogen, $R^4$ is C1-C5 alkyl optionally substituted with one or more halogen, or C2-C5 alkenyl optionally substituted with one or more halogen, and $R^5$ is C1-C5 alkyl optionally substituted with one or more halogen;

a malononitrile compound of the formula (II-vi) in which $R^1$ and $R^2$ are hydrogen, $R^3$ is hydrogen, $R^4$ is 2,2,2-trifluoroethyl, and $R^5$ is C1-C5 alkyl optionally substituted with one or more halogen;

a malononitrile compound represented by the formula (II-vii):

$$\text{(II-vii)}$$

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen; C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-vii) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^9)R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-vii) in which $R^1$ and $R^2$ are hydrogen, $R^3$ is hydrogen, $R^4$ is C1-C5 alkyl optionally substituted with one or more halogen, or C2-C5 alkenyl optionally substituted with one or more halogen, and $R^5$ is C1-C5 alkyl optionally substituted with one or more halogen;

a malononitrile compound of the formula (II-vii) in which $R^1$ and $R^2$ are hydrogen, $R^3$ is hydrogen, $R^4$ is 2,2,2-trifluoroethyl, and $R^5$ is C1-C5 alkyl optionally substituted with one or more halogen;

a malononitrile compound represented by the formula (II-viii):

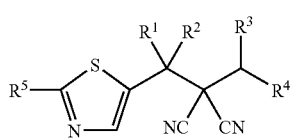

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-viii) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-viii) in which $R^1$ and $R^2$ are hydrogen, $R^3$ is hydrogen, $R^4$ is C1-C5 alkyl optionally substituted with one or more halogen, or C2-C5 alkenyl optionally substituted with one or more halogen, and $R^5$ is C1-C5 alkyl optionally substituted with one or more halogen;

a malononitrile compound of the formula (II-viii) in which $R^1$ and $R^2$ are hydrogen, $R^3$ is hydrogen, $R^4$ is 2,2,2-trifluoroethyl, and $R^5$ is C1-C5 alkyl optionally substituted with one or more halogen;

a malononitrile compound represented by the formula (II-ix):

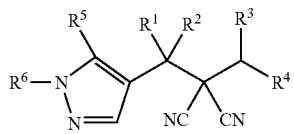

(II-ix)

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, $R^6$ represents C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-ix) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^6$ is C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-ix) in which $R^1$ and $R^2$ are hydrogen, $R^3$ is hydrogen, $R^4$ is C1-C5 alkyl optionally substituted with one or more halogen, or C2-C5 alkenyl optionally substituted with one or more halogen, $R^5$ is C1-C5 alkyl optionally substituted with one or more halogen, and $R^6$ is C1-C5 alkyl optionally substituted with one or more halogen;

a malononitrile compound of the formula (II-ix) in which $R^1$ and $R^2$ are hydrogen, $R^3$ is hydrogen, $R^4$ is 2,2,2-trifluoroethyl, $R^5$ is C1-C5 alkyl optionally substituted with one or more halogen, and $R^6$ is C1-C5 alkyl optionally substituted with one or more halogen;

a malononitrile compound represented by the formula (II-x)

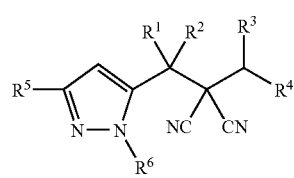

(II-x)

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen;

$R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen;

$R^5$ represent halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by $C(OR^{19})R^{20}R^{21}$, or hydrogen, $R^6$ represents C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;
 a malononitrile compound of the formula (II-x) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, and $R^6$ is C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;
 a malononitrile compound of the formula (II-x) in which $R^1$ and $R^2$ are hydrogen, $R^3$ is hydrogen, $R^4$ is C1-C5 alkyl optionally substituted with one or more halogen or C2-C5 alkenyl optionally substituted with one or more halogen, $R^5$ is C1-C5 alkyl optionally substituted with one or more halogen, and $R^6$ is C1-C5 alkyl optionally substituted with one or more halogen;
 a malononitrile compound of the formula (II-x) in which $R^1$ and $R^2$ are hydrogen, $R^3$ is hydrogen, $R^4$ is 2,2,2-trifluoroethyl, $R^5$ is C1-C5 alkyl optionally substituted with one or more halogen, and $R^6$ is C1-C5 alkyl optionally substituted with one or more halogen;
 a malononitrile compound represented by the formula (II-xi):

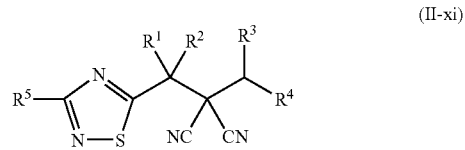

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen C2-C6 alkylcarbonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-xi) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-xi) in which $R^1$ and $R^2$ are hydrogen, $R^3$ is hydrogen, $R^4$ is C1-C5 alkyl optionally substituted with one or more halogen or C2-C5 alkenyl optionally substituted with one or more halogen, and $R^5$ is C1-C5 alkyl optionally substituted with one or more halogen;

a malononitrile compound of the formula (II-xi) in which $R^1$ and $R^2$ are hydrogen, $R^3$ is hydrogen, $R^4$ is 2,2,2-trifluoroethyl, and $R^5$ is C1-C5 alkyl optionally substituted with one or more halogen;

a malononitrile compound represented by the formula (II-xii):

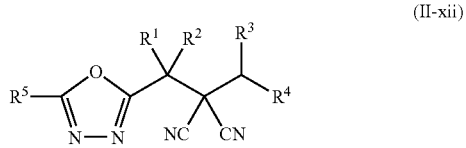

(II-xii)

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen C2-C6 alkylcarbonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-xii) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-xii) in which $R^1$ and $R^2$ are hydrogen, $R^3$ is hydrogen, $R^4$ is C1-C5 alkyl optionally substituted with one or more halogen or C2-C5 alkenyl optionally substituted with one or more halogen, and $R^5$ is C1-C5 alkyl optionally substituted with one or more halogen;

a malononitrile compound of the formula (II-xii) in which $R^1$ and $R^2$ are hydrogen, $R^3$ is hydrogen, $R^4$ is 2,2,2-trifluoroethyl, and $R^5$ is C1-C5 alkyl optionally substituted with one or more halogen;

a malononitrile compound represented by the formula (II-xiii):

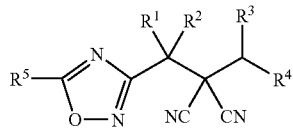

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, $R^5$ represents halogen, cyano, nitro, formyl, $SF_5$, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen C2-C6 alkylcarbonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-xiii) in which $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen C1-C5 alkylsulfonyl optionally substituted with one or more halogen, a group represented by $C(OR^{19})R^{20}R^{21}$ or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen;

a malononitrile compound of the formula (II-xiii) in which $R^1$ and $R^2$ are hydrogen, $R^3$ is hydrogen, $R^4$ is C1-C5 alkyl optionally substituted with one or more halogen or C2-C5 alkenyl optionally substituted with one or more halogen, and $R^5$ is C1-C5 alkyl optionally substituted with one or more halogen;

a malononitrile compound of the formula (II-xiii) in which $R^1$ and $R^2$ are hydrogen, $R^3$ is hydrogen, $R^4$ is 2,2,2-trifluoroethyl, and $R^5$ is C1-C5 alkyl optionally substituted with one or more halogen.

Then, a process of producing the present compound will be shown.

Hereinafter, Het represents a moiety other than $R^{100}$ in the formula (I). Therefore, for example, the present compound represented by the formula (I) is expressed as follows:

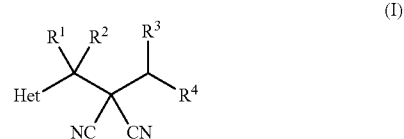

(I)

The present compound can be prepared, for example, according to the following Process 1 and Process 2.

(Process 1)

Method comprising a reaction of the compound (a) and the compound (b):

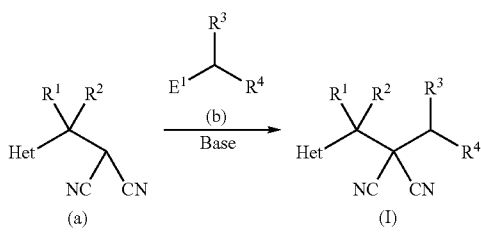

wherein $R^1$ represents C1-C5 alkyl optionally substituted with one or more halogen, C2-C5 alkenyl optionally substituted with one or more halogen, C2-C5 alkynyl optionally substituted with one or more halogen, or hydrogen, $R^2$ represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, $R^3$ and $R^4$ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or $R^3$ and $R^4$ are taken together to represent C2-C6 alkanediyl optionally substituted with one or more halogen or C4-C6 alkenediyl optionally substituted with one or more halogen, and $E^1$ represents a leaving group (e.g. chlorine, bromine, iodine, methanesulfonyloxy, trifluoromethanesulfonyloxy or toluenesulfonyloxy).

The reaction is usually performed in a solvent in the presence of a base.

A solvent used in the reaction includes acid amide such as N,N-dimethylformamide, ether such as diethyl ether or tetrahydrofuran, organic sulfur such as dimethyl sulfoxide or sulfolane, halogenated hydrocarbon such as 1,2-dichloroethane or chlorobenzene, aromatic hydrocarbon such as toluene or xylene, and a mixture thereof.

A base used in the reaction includes an inorganic base such as sodium hydride, sodium carbonate or potassium carbonate, an alkali metal alkoxide such as potassium-t-butoxide, and an organic base such as 4-dimethylaminopyridine, 1,4-diazabicyclo[2.2.2]octane or 1,8-diazabicyclo[5.4.0]-7-undecene.

The amount of a base used in the reaction is usually 1 to 10 moles per 1 mole of the compound (a).

The amount of the compound (b) used in the reaction is usually 1 to 10 moles per 1 mole of the compound (a).

The reaction temperature is usually in the range of −20 to 100° C. The reaction time is usually in the range of 1 to 24 hours.

After completion of the reaction, the present compound represented by the formula (I) can be isolated by subjecting the reaction mixture to post-treatment, for example, by addition of the reaction mixture into water followed by extraction with an organic solvent and then concentration of the extract. The isolated present compound represented by the formula (I) may be purified by chromatography, recrystallization or the like, if necessary.

(Process 2)

Method comprising a reaction of the compound (c) and the compound (d):

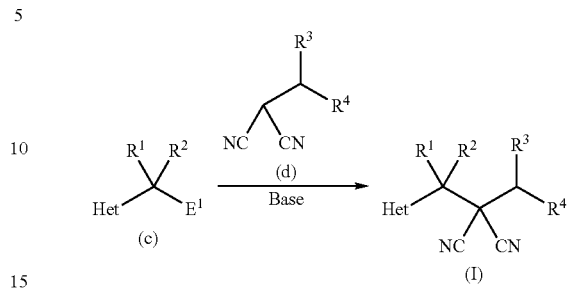

wherein $E^1$, $R^1$, $R^2$, $R^3$ and $R^4$ are as defined above.

The reaction is usually performed in a solvent in the presence of a base.

A solvent used in the reaction includes acid amide such as N,N-dimethylformamide, ether such as diethyl ether or tetrahydrofuran, organic sulfur such as dimethyl sulfoxide or sulfolane, halogenated hydrocarbon such as 1,2-dichloroethane or chlorobenzene, aromatic hydrocarbon such as toluene or xylene, and a mixture thereof.

A base used in the reaction includes an inorganic base such as sodium hydride, sodium carbonate or potassium carbonate, an alkali metal alkoxide such as potassium-t-butoxide, and an organic base such as 4-dimethylaminopyridine, 1,4-diazabicyclo[2.2.2]octane or 1,8-diazabicyclo[5.4.0]-7-undecene.

The amount of a base used in the reaction is usually 1 to 10 moles per 1 mole of the compound (c).

The amount of the compound (d) used in the reaction is usually 1 to 10 moles per 1 mole of the compound (c).

The reaction temperature is usually in the range of −20 to 100° C. The reaction time is usually in the range of 1 to 24 hours.

After completion of the reaction, the present compound represented by the formula (I) can be isolated by subjecting the reaction mixture to post-treatment, for example, by addition of the reaction mixture into water followed by extraction with an organic solvent and then concentration of the extract. The isolated present compound represented by the formula (I) may be purified by chromatography, recrystallization or the like, if necessary.

Then, a reference process of producing an intermediate for production of the present compound will be shown.

(Reference Process 1)

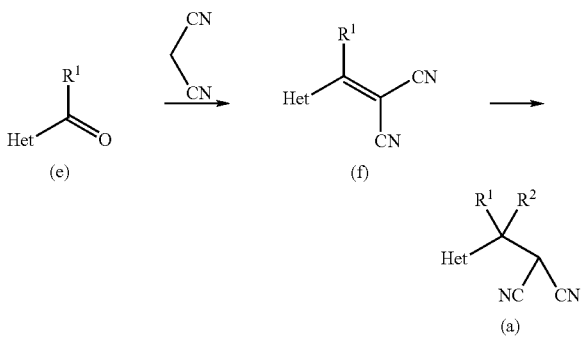

wherein $R^1$ and $R^2$ are as defined above.

(First Step)

The compound (f) can be prepared by reacting the compound (e) with malononitrile.

The reaction is usually performed in a solvent. A solvent used in the reaction includes acid amide such as N,N-dimethylformamide, ether such as diethyl ether or tetrahydrofuran, halogenated hydrocarbon such as chloroform, 1,2-dichloroethane or chlorobenzene, aromatic hydrocarbon such as toluene or xylene, alcohol such as methanol, ethanol or isopropanol and a mixture thereof.

The reaction may be performed in the presence of a base, if necessary. A base used in the reaction includes tetrabutylammonium hydroxide.

The amount of a base used in the reaction is usually 0.01 to 0.5 moles per 1 mole of the compound (e).

The amount of malononitrile used in the reaction is usually 1 to 10 moles per 1 mole of the compound (e).

The reaction temperature is usually in the range of −20 to 200° C. The reaction time is usually in the range of 1 to 24 hours.

The reaction may be performed while water produced by the reaction is removed from the reaction system, if necessary.

After completion of the reaction, the compound (f) can be isolated by subjecting the reaction mixture to post-treatment, for example, by addition of the reaction mixture into water followed by extraction with an organic solvent and then concentration of the extract. The isolated compound (f) may be purified by chromatography, recrystallization or the like, if necessary.

(Second Process)

(1) In a case that $R^2$ is C1-C5 alkyl optionally substituted with halogen, C2-C5 alkenyl optionally substituted with halogen, or alkenyl optionally substituted with halogen;

The compound (a) can be prepared by reacting the compound (f) with an organometallic compound.

The reaction is usually performed in a solvent.

A solvent used in the reaction includes ether such as diethyl ether or tetrahydrofuran, aromatic hydrocarbon such as toluene or xylene, and a mixture thereof.

An organometallic compound used in the reaction includes an organic magnesium compound such as methylmagnesium iodide, ethylmagnesium bromide, isopropylmagnesium bromide, vinylmagnesium bromide, ethylmagnesium bromide or dimethylmagnesium, an organic lithium compound such as methyllithium, an organic zinc compound such as diethylzinc, and an organic copper compound such as trifluoromethylcopper.

The amount of an organometallic compound used in the reaction is usually 1 to 10 moles per 1 mole of the compound (f).

The reaction may be performed in the presence of a copper salt, if necessary. A copper salt used in the reaction includes copper(I) iodide and copper(I) bromide. The amount of a copper salt used in the reaction is usually 0.05 to 1 mole per 1 mole of the compound (f).

The reaction temperature is usually in the range of −20 to 100° C. The reaction time is usually in the range of 1 to 24 hours.

After completion of the reaction, the compound (a) can be isolated by subjecting the reaction mixture to post-treatment, for example, by addition of the reaction mixture into water followed by extraction with an organic solvent and then concentration of the extract. The isolated compound (a) may be purified by chromatography, recrystallization or the like, if necessary.

(2) In a case that $R^2$ is hydrogen;

The compound (a) can be prepared by subjecting the compound (f) to a reducing reaction.

The reducing reaction is usually performed in a solvent.

A solvent used in the reaction includes ether such as diethyl ether or tetrahydrofuran, aromatic hydrocarbon such as toluene or xylene, alcohol such as methanol, ethanol or propanol, water, and a mixture thereof.

A reducing agent used in the reaction includes sodium borohydride.

The amount of a reducing agent used in the reaction is usually 0.25 to 2 moles per 1 mole of the compound (f).

The reaction temperature is usually in the range of 0 to 50° C. The reaction time is usually in the range of a second to 24 hours.

After completion of the reaction, the compound (a) can be isolated by subjecting the reaction mixture to post-treatment, for example, by addition of the reaction mixture into water followed by extraction with an organic solvent and then concentration of the extract. The isolated compound (a) may be purified by chromatography, recrystallization or the like, if necessary.

(3) In a case that $R^2$ is cyano;

The compound (a) can be prepared by reacting the compound (f) with a cyanide salt.

The reaction is usually performed in a solvent.

A solvent used in the reaction includes ether such as diethyl ether or tetrahydrofuran, aromatic hydrocarbon such as toluene or xylene, and a mixture thereof.

A cyanide salt used in the reaction includes tetrabutylammonium cyanide.

The amount of cyanide used in the reaction is usually 1 to 10 moles per 1 mole of the compound (f).

The reaction temperature is usually in the range of −20 to 100° C. The reaction time is usually in the range of 1 to 24 hours.

After completion of the reaction, the compound (a) can be isolated by subjecting the reaction mixture to post-treatment, for example, by addition of the reaction mixture into water followed by extraction with an organic solvent and then concentration of the extract. The isolated compound (a) may be purified by chromatography, recrystallization or the like, if necessary.

(Reference Process 2)

The compound (d) can be prepared, for example, by reacting the compound (b) with malononitrile.

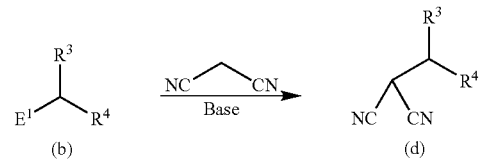

The reaction is usually performed in a solvent in the presence of a base.

A solvent used in the reaction includes acid amide such as N,N-dimethylformamide, ether such as diethyl ether or tetrahydrofuran, organic sulfur such as dimethyl sulfoxide or sulfolane, halogenated hydrocarbon such as 1,2-dichloroethane or chlorobenzene, aromatic hydrocarbon such as toluene or xylene, and a mixture thereof.

A base used in the reaction includes an inorganic base such as sodium hydride, sodium carbonate or potassium carbonate, an alkali metal alkoxide such as potassium-t-butoxide, and an organic base such as 4-dimethylaminopyridine, 1,4-diazabicyclo[2.2.2]octane or 1,8-diazabicyclo[5.4.0]-7-undecene.

The amount of a base used in the reaction is usually 1 to 10 moles per 1 mole of the compound (b).

The amount of malononitrile used in the reaction is usually 1 to 10 moles per 1 mole of the compound (b).

The reaction temperature is usually in the range of −20 to 100° C. The reaction time is usually in the range of 1 to 24 hours.

After completion of the reaction, the compound (d) can be isolated by subjecting the reaction mixture to post-treatment, for example, by addition of the reaction mixture into water followed by extraction with an organic solvent and then concentration of the extract. The isolated compound (d) may be purified by chromatography, recrystallization or the like, if necessary.

(Reference Process 3)

The compound (d) may be also prepared by the following method:

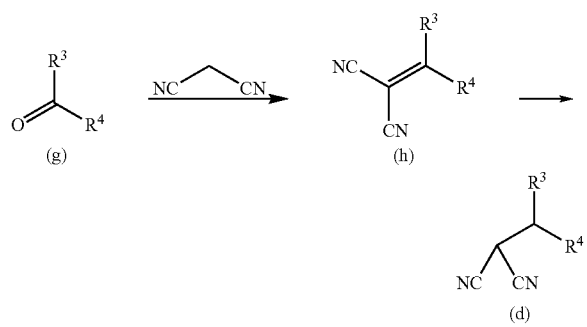

wherein $R^3$ and $R^4$ are as defined above.

(First Step)

The compound (h) can be prepared by reacting the compound (g) with malononitrile.

The reaction is usually performed in a solvent. A solvent used in the reaction includes acid amide such as N,N-dimethylformamide, ether such as diethyl ether or tetrahydrofuran, halogenated hydrocarbon such as chloroform, 1,2-dichloroethane or chlorobenzene, aromatic hydrocarbon such as toluene or xylene, alcohol such as methanol, ethanol or isopropanl, and a mixture thereof.

The reaction may be performed in the presence of a base, if necessary. A base used in the reaction includes tetrabutylammonium hydroxide.

The amount of a base used in the reaction is usually 0.01 to 0.5 moles per 1 mole of the compound (g).

The amount of malononitrile used in the reaction is usually 1 to 10 moles per 1 mole of the compound (g).

The reaction temperature is usually in the range of −20 to 200° C. The reaction time is usually in the range of 1 to 24 hours.

The reaction may be also performed while water produced by the reaction is removed form the reaction system, if necessary.

After completion of the reaction, the compound (h) can be isolated by subjecting the reaction mixture to post-treatment, for example, by addition of the reaction mixture into water followed by extraction with an organic solvent and then concentration of the extract. The isolated compound (h) may be purified by chromatography, recrystallization or the like, if necessary.

(Second Step)

The compound (d) can be also prepared by reacting the compound (h) with a reducing agent.

The reaction is usually performed in a solvent.

A solvent used in the reaction includes alcohol such as methanol, ethanol, isopropyl alcohol or t-butyl alcohol, ether such as diethyl ether or tetrahydrofuran, halogenated hydrocarbon such as 1,2-dichloroethane or chlorobenzene, aromatic hydrocarbon such as toluene or xylene, and a mixture thereof.

A reducing agent used in the reaction includes sodium borohydride, lithium borohydride and diisopropylaluminum hydride.

The amount of a reducing agent used in the reaction, depending on the kind of the reducing agent, is usually 0.25 to 5 moles per 1 mole of the compound (h).

The reaction temperature is usually in the range of −20 to 100° C. The reaction time is usually in the range of 1 to 24 hours.

After completion of the reaction, the compound (d) can be isolated by subjecting the reaction mixture to post-treatment, for example, by addition of the reaction mixture into water followed by extraction with an organic solvent and then concentration of the extract. The isolated compound (d) may be purified by chromatography, recrystallization or the like, if necessary.

(Reference Process 4)

The compound (c) can be prepared from the compound (i), for example, according to the following scheme:

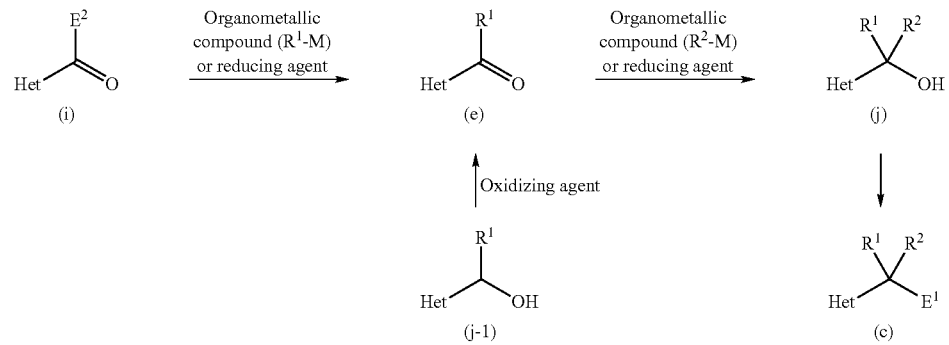

wherein $E^1$, $R^1$ and $R^2$ are as defined above, and $E^2$ represents a leaving group (e.g. chlorine, methoxy, ethoxy, 1-imidazolyl, 1-pyrazolyl, dimethylamino, 1-piperidyl, or N-methyl-N-methoxyamino.

That is, the compound (e) can be prepared by reacting the compound (i) with an organometallic compound represented by $R^1$-M (e.g. an organic magnesium compound such as methylmagnesium iodide, ethylmagnesium bromide, isopropylmagnesium bromide, vinylmagnesium bromide, ethynylmagnesium bromide or dimethylmagnesium, an organic lithium compound such as methyllithium, an organic zinc compound such as diethylzinc, or an organic copper compound such as trifluoromethylcopper) or a reducing agent (e.g. lithium aluminum hydride or diisobutylaluminum hydride).

The compound (j) can be prepared by reacting the compound (i) with an organometallic compound represented by $R^1$-M (e.g. an organic magnesium compound such as methylmagnesium iodide, ethylmagnesium bromide, isopropylmagnesium bromide, vinylmagnesium bromide, ethynylmagnesium bromide or dimethylmagnesium, an organic lithium compound such as methyllithium, an organic zinc compound such as diethylzinc, or an organic copper compound such as trifluoromethylcopper) or a reducing agent (e.g. lithium aluminum hydride or diisobutylaluminum hydride).

In addition, the compound (c) can be prepared by halogenating (e.g. reacting with an acid halogenating agent such as thionyl chloride or phosphorus oxychloride) or sulfonating (e.g. reacting with trifluoromethanesulfonic anhydride, methanesulfonyl chloride or toluenesulfonic acid chloride in the presence of a base) the compound (j).

The compound (e) can be also prepared by reacting the compound (j) wherein $R^2$ is hydrogen, i.e. the compound (j-1), with an oxidizing agent (e.g. chromate, dimethylsulfoxide/oxalyl chloride, or manganese dioxide).

(Reference Process 5)

Among the compound (i), the compound (i-1) can be prepared, for example, according to a method described in Journal of Chemical Society, Perkin Trans., 14, 1716, 2001, by a route shown in the following scheme:

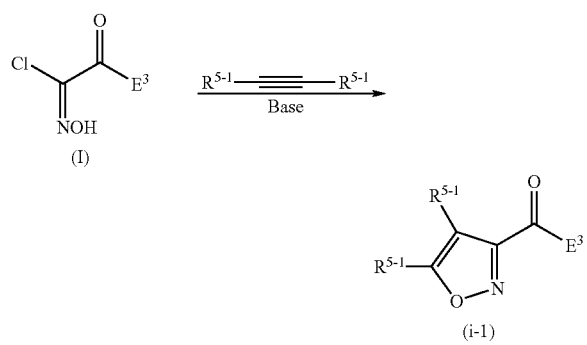

(i-1)

wherein $R^{5-1}$ independently represents C1-C5 alkyl optionally substituted with halogen, C3-C6 cycloalkyl optionally substituted with halogen, C1-C5 alkylsulfinyl optionally substituted with halogen, C1-C5 alkylsulfonyl optionally substituted with halogen, C2-C6 alkylcarbonyl optionally substituted with halogen, C2-C5 alkoxycarbonyl optionally substituted with halogen, cyano, nitro or hydrogen, and $E^3$ represents methoxy or ethoxy.

(Reference Process 6)

Among the compound (j), the compound (j-2) can be prepared, for example, according to a route shown in the following scheme:

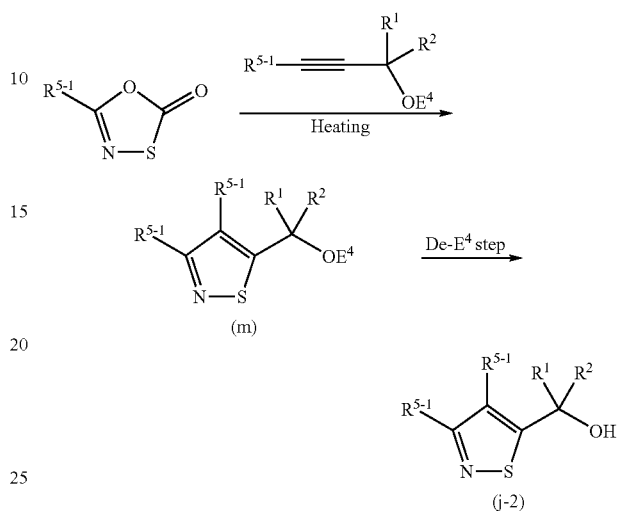

[wherein $R^1$, $R^2$ and $R^5$-1 are as defined above, and $E^4$ represents a protecting group (e.g. a tetrahydropyran-2-yl group etc.).

(Reference Process 7)

Among the compound (i), the compounds (i-2), (i-3) and (i-4) can be prepared, for example, according to a route shown in the following scheme:

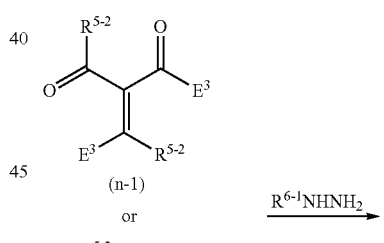

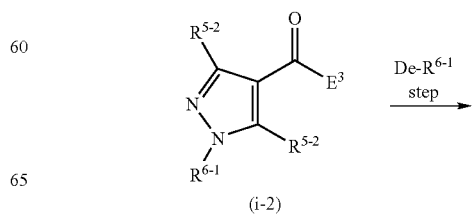

-continued

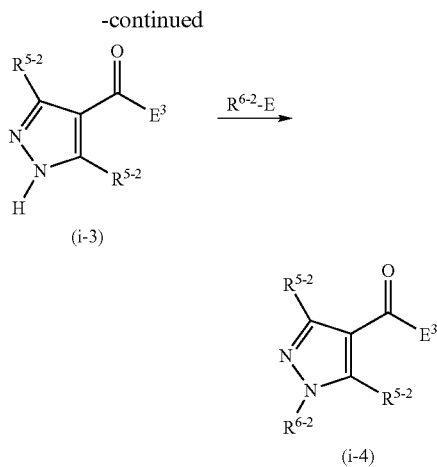

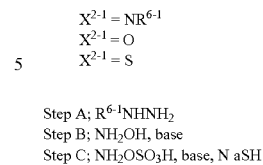

Step A; $R^{6-1}NHNH_2$
Step B; $NH_2OH$, base
Step C; $NH_2OSO_3H$, base, N aSH wherein $E^4$ and $R^{6-1}$ are as defined above, $X^{2-1}$ represents oxygen, sulfur or $NR^{6-1}$, $R^{5-3}$ represents C1-C5 alkyl optionally substituted with halogen or C3-C6 cycloalkyl optionally substituted with halogen, and $R^{5-4}$ represents halogen or hydrogen.

(Reference Process 9)

Among the compound (e), the compound (e-1) can be prepared according to a method, for example, described in Chem. Heterocycl. Compd. (Engl. Transl.), 28, 53, 1992, for example, by a route shown in the following scheme:

wherein $E^1$ and $E^3$ are as defined above, $R^{6-1}$ represents C1-C5 alkyl optionally substituted with halogen, C3-C6 alkyl optionally substituted with halogen, C2-C5 alkenyl optionally substituted with halogen, or alkynyl optionally substituted with halogen, $R^{5-2}$ independently represents C1-C5 alkyl optionally substituted with halogen, C3-C6 cycloalkyl optionally substituted with halogen, or hydrogen, and $R^{6-2}$ represents C1-C5 alkyl optionally substituted with halogen, C2-C5 alkenyl optionally substituted with halogen, C2-C5 alkynyl optionally substituted with halogen, C3-C6 cycloalkyl optionally substituted with halogen, (C1-C5 alkyloxy optionally substituted with halogen) C1-C3 alkyl, C1-C5 alkylsulfinyl optionally substituted with halogen, C1-C5 alkylsulfonyl optionally substituted with halogen, C2-C6 alkylcarbonyl optionally substituted with halogen, C2-C5 alkoxycarbonyl optionally substituted with halogen, a group represented by $C(=X^5)NR^{12}R^{13}$ (wherein $X^5$, $R^{12}$ and $R^{13}$ are as defined above) or a group represented by $(CH_2)_m Q$ (wherein m and Q are defined above).

(Reference Process 8)

Among the compound (j), the compound (j-3) can be prepared, for example, according to a route shown in the following scheme:

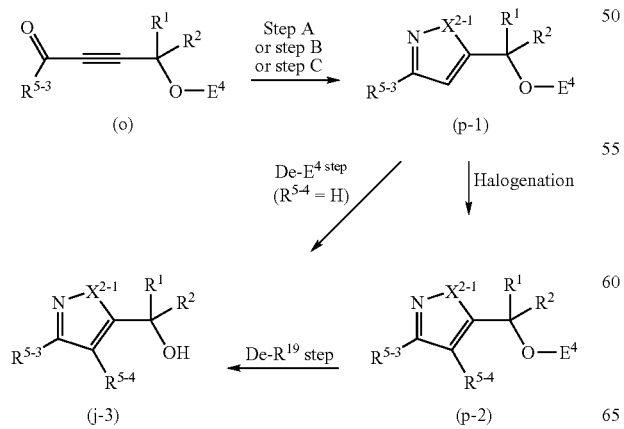

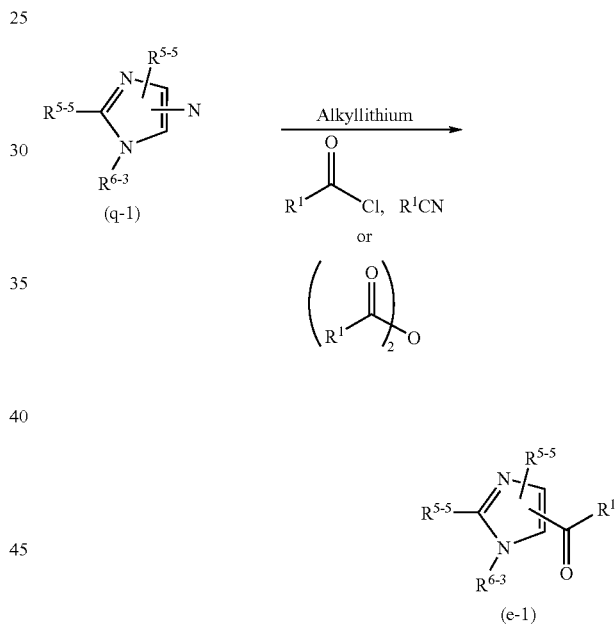

wherein $R^1$ is as defined above, $R^{5-5}$ represents C1-C5 alkyl optionally substituted with halogen, C3-C6 cycloalkyl optionally substituted with halogen, halogen or hydrogen, and $R^{6-3}$ represents C1-C5 alkyl optionally substituted with halogen, C3-C6 cycloalkyl optionally substituted with halogen, C2-C5 alkenyl optionally substituted with halogen or C2-C5 alkynyl optionally substituted with halogen.

(Reference Process 10)

Among the compound (e), the compound (e-2) can be prepared according to a method described in, for example, Heterocycles, 23, 1759, (1985), for example, by a route shown in the following scheme:

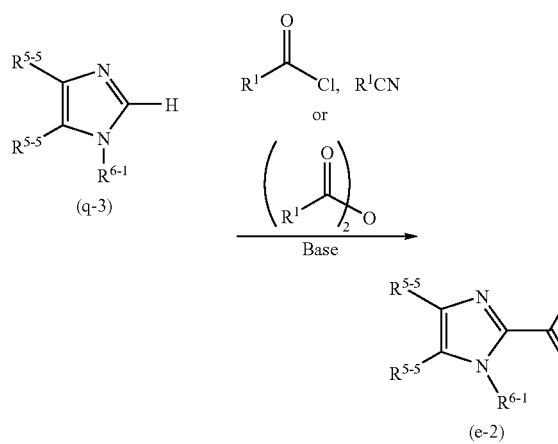

wherein $R^1$, $R^{5-5}$ and $R^{6-1}$ are as defined above.

(Reference Process 11)

Among the compound (i), the compound (i-5) can be prepared according to a method described in, for example, JP-A 2001-58979, for example, by a route shown in the following scheme:

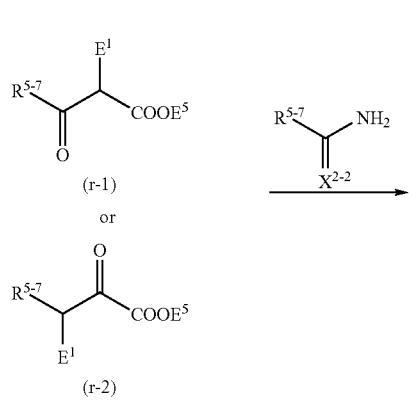

wherein $E^1$ is as defined above, $R^{5-7}$ represents C1-C5 alkyl optionally substituted with halogen or C3-C6 cycloalkyl optionally substituted with halogen, $X^{2-2}$ represents oxygen, sulfur or $NR^{6-4}$, $R^{6-4}$ represents C1-C5 alkyl optionally substituted with halogen, C3-C6 cycloalkyl optionally substituted with halogen, C2-C5 alkenyl optionally substituted with halogen, or C2-C5 alkynyl optionally substituted with halogen, and $E^5$ represents methyl or ethyl.

(Reference Process 12)

Among the compound (c), the compounds (c-1) and (c-2) can be prepared, for example, according to a route shown in the following scheme:

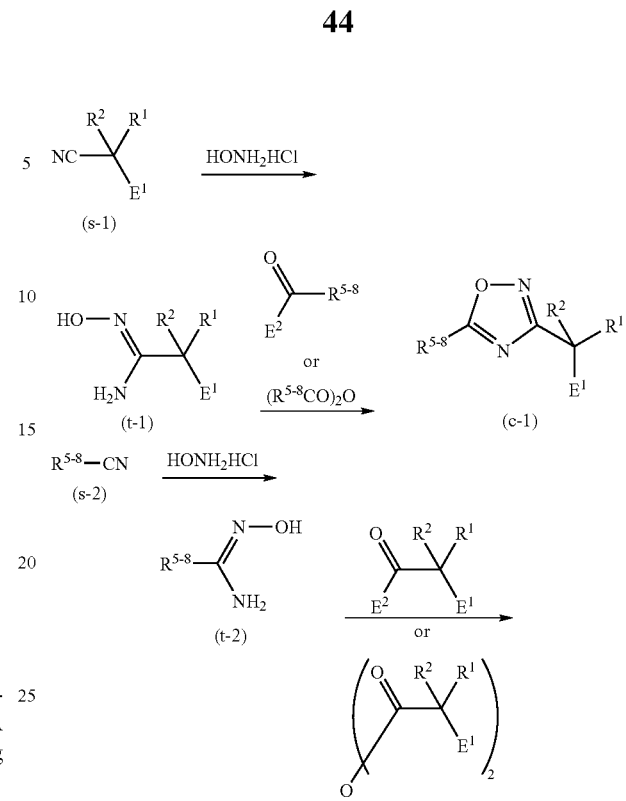

wherein $E^1$, $E^2$, $R^1$ and $R^2$ are as defined above, and $R^{5-8}$ represents C1-C5 alkyl optionally substituted with halogen, C3-C6 cycloalkyl optionally substituted with halogen, C2-C5 alkenyl optionally substituted with halogen, or C2-C5 alkynyl.

(Reference Process 13)

Among the compound (i), the compounds (i-6) and (i-7) can be prepared, for example, according to a route shown in the following scheme:

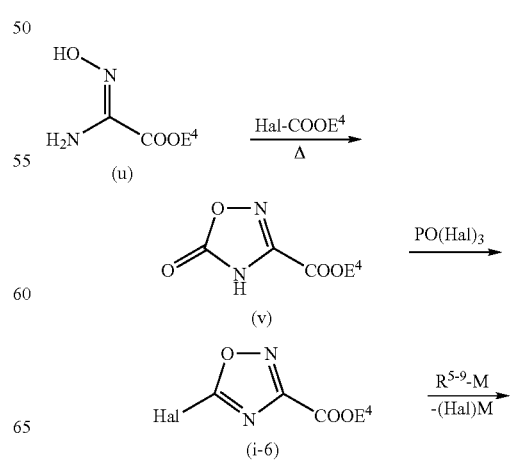

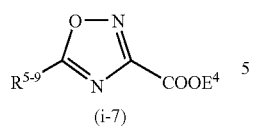

(i-7)

wherein $E^4$ is as defined above, $R^{5-9}$ represents C1-C5 alkyloxy optionally substituted with halogen, C2-C5 alkenyloxy optionally substituted with halogen, C2-C5 alkynyloxy optionally substituted with halogen, C1-C5 alkylthio optionally substituted with halogen, and Hal independently represents halogen such as chlorine or bromine.

(Reference Process 14)

Among the compound (i), the compound (i-9) can be prepared, for example, according to a route shown in the following scheme:

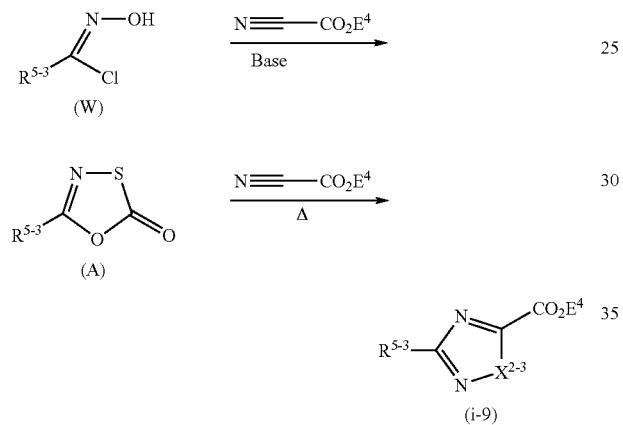

wherein $E^4$ and $R^{5-3}$ are as defined above, and $X^{2-3}$ represents oxygen or sulfur.

(Reference Process 15)

Among the compound (c), the compound (c-3) can be prepared according to a method described in, for example, JP-A 55-27042, for example, by a route shown in the following scheme:

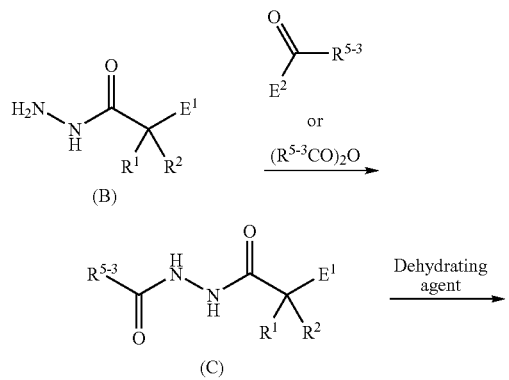

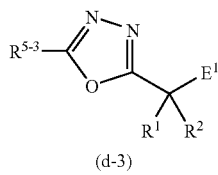

(d-3)

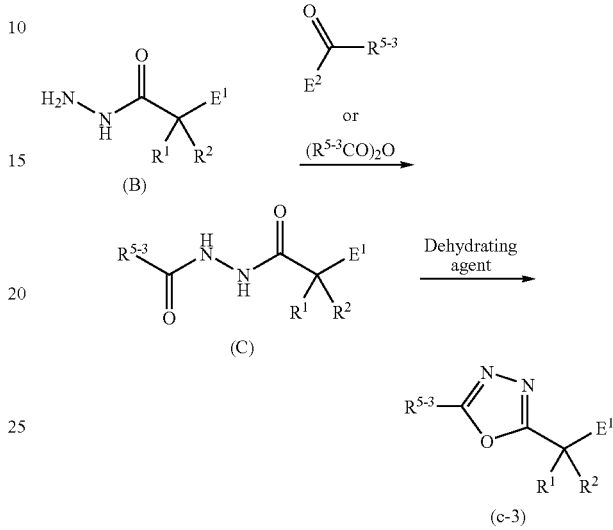

(c-3)

wherein $R^1$, $R^2$, $E^1$, $E^2$ and $R^{5-3}$ are as defined above.

(Reference Process 16)

The compounds (c), (e), (i) and (j) in which $X^1$ is nitrogen, $X^2$, $X^3$ and $X^4$ each are $CR^5$ and Z represents $NR^6$, which are pyrazole, can be synthesized according to a method described in Houben-Weyl, Methoden der Organischen Chemi, Hetarene III, Teil. 3, p. 399-710.

(Reference Process 17)

The compounds (c), (e), (i) and (j) in which $X^1$ is nitrogen atom, each of $X^2$, $X^3$ and $X^4$ is $CR^6$ and Z represents an oxygen atom, which are isoxazole, can be synthesized according to a method described in Houben-Weyl, Methoden der Organischen Chemi, Hetarene III, Teil. 1, p. 45-204.

(Reference Process 18)

The compounds (c), (e), (i) and (j) in which $X^1$ is nitrogen, $X^2$, $X^3$ and $X^4$ each are $CR^5$ and Z represents sulfur, which are isothiazole, can be synthesized according to a method described in Houben-Weyl, Methoden der Organischen Chemi, Hetarene III, Teil. 1, p. 668-788.

(Reference Process 19)

The compounds (c), (e), (i) and (j) in which $X^2$ is nitrogen, $X^1$, $X^3$ and $X^4$ each are $CR^5$ and Z represents $NR^6$, which are imidazole, can be synthesized according to a method described in Houben-Weyl, Methoden der Organischen Chemi, Hetarene III, Teil. 3, p. 1-192.

(Reference Process 20)

The compound (c), (e), (i) and (j) in which $X^2$ is nitrogen, $X^1$, $X^3$ and $X^4$ each are $CR^5$ and Z represents oxygen, which are 1,3-oxazole, can be synthesized according to a method described in Houben-Weyl, Methoden der Organischen Chemi, Hetarene III, Teil. 1, p. 891-1012.

(Reference Process 21)

The compounds (c), (e), (i) and (j) in which $X^2$ is nitrogen, $X^1$, $X^3$ and $X^4$ each are $CR^5$ and Z represents sulfur, which are 1,3-thiazole, can be synthesized according to a method described in Houben-Weyl, Methoden der Organischen Chemi, Hetarene III, Teil. 3, p. 1-361.

(Reference Process 22)

The compounds (c), (e), (i) and (j) in which $X^1$ and $X^3$ are nitrogen, $X^2$ and $X^4$ each are $CR^5$ and Z represents oxygen, which are 1,2,4-oxadiazole, can be synthesized according to a method described in Houben-Weyl, Methoden der Organischen Chemi, Hetarene III, Teil. 3, p. 409-518.

(Reference Process 23)

The compounds (c), (e), (i) and (j) in which $X^2$ and $X^3$ are nitrogen, $X^1$ and $X^4$ each are $CR^5$ and Z represents oxygen, which are 1,3,4-oxadiazole, can be synthesized according to a method described in Houben-Weyl, Methoden der Organischen Chemi, Hetarene III, Teil. 3, p. 526-630.

(Reference Process 24)

The compounds (c), (e), (i) and (j) in which $X^1$ and $X^3$ are nitrogen, $X^2$ and $X^4$ each are $CR^5$ and Z represents sulfur, which are 1,2,4-thiadiazole, can be synthesized according to a method described in Houben-Weyl, Methoden der Organischen Chemi, Hetarene III, Teil. 4, p. 105-148.

(Reference Process 25)

The compounds (c), (e), (i) and (j) in which $X^1$ and $X^4$ are nitrogen, $X^2$ and $X^3$ each are $CR^5$ and Z represents sulfur, which are 1,2,5-thiadiazole, can be synthesized according to a method described in Houben-Weyl, Methoden der Organischen Chemi, Hetarene III, Teil. 4, p. 152-168.

(Reference Process 26)

The compounds (c), (e), (i) and (j) in which $X^2$ and $X^3$ are nitrogen, $X^1$ and $X^4$ each are $CR^5$ and Z represents sulfur, which are 1,3,4-thiadiazole, can be synthesized according to a method described in Houben-Weyl, Methoden der Organischen Chemi, Hetarene III, Teil. 4, p. 189-298.

(Reference Process 27)

The compounds (c), (e), (i) and (j) in which $X^1$ and $X^2$ are nitrogen, $X^3$ and $X^4$ each are $CR^5$ and Z represents $NR^6$, which are 1,2,3-triazole, can be synthesized according to a method described in Houben-Weyl, Methoden der Organischen Chemi, Hetarene III, Teil. 4, p. 305-389.

(Reference Process 28)

The compounds (c), (e), (i) and (j) in which $X^1$ and $X^3$ are nitrogen, $X^2$ and $X^4$ each are $CR^5$ and Z represents $NR^6$, which are 1,2,4-triazole, can be synthesized according to a method described in Houben-Weyl, Methoden der Organischen Chemi, Hetarene III, Teil. 4, p. 479-586.

Pests against which the present compound has controlling effect include harmful arthropods such as insects and mites, and harmful nematodes. More specifically, examples thereof are listed below.

Hemiptera:

Delphacidae such as *Laodelphax striatellus, Nilaparvata lugens, Sogatella furcifera* and the like, Deltocephalidae such as *Nephotettix cincticeps, Nephotettix virescens* and the like, Aphididae such as *Aphis gossypii, Myzus persicae* and the like, Pentatomidae and Alydidae, such as *Nezara antennata, Riptortus clavetus, Plautia stali, Halyomorpha mista, Eysarcoris lewisi, Eysarcoris parvus*, and the like, Aleyrodidae such as *Trialeurodes vaporariorum, Bemisia argentifolii* and the like, Diaspididae, Coccidae and Margarodidae, such as *Aonidiella aurantii, Comstockaspis perniciosa, Unaspis citri, Ceroplastes rubens, Icerya purchasi* and the like, Tingidae, Psyllidae, and the like;

Lepidoptera:

Pyralidae such as *Chilo suppressalis, Cnaphalocrocis medinalis, Notarcha derogata, Plodia interpunctella* and the like, Noctuidae such as *Spodoptera litura, Pseudaletia separata, Trichoplusia* spp., *Heliothis* spp., *Helicoverpa* spp. and the like, Pieridae such as *Pieris rapae* and the like, Tortricidae such as *Adoxophyes* spp., *Grapholita molesta, Cydia pomonella* and the like, Carposinidae such as *Carposina niponensis* and the like, Lyonetiidae such as *Lyonetia* spp. and the like, Lymantriidae such as *Lymantria* spp., *Euproctis* spp. and the like, Yponomeutidae such as *Plutella xylostella* and the like, Gelechiidae such as *Pectinophora gossypiella* and the like, Arctiidae such as *Hyphantria cunea* and the like, Tineidae such as *Tinea translucens, Tineola bisselliella* and the like;

Diptera:

Culicidae such as *Culex pipiens pallens, Culex tritaeniorhynchus, Culex quinquefasciatus* and the like, Aedes spp. such as *Aedes aegypti, Aedes albopictus* and the like,

*Anopheles* spp. such as *Anopheles sinensis* and the like,

Chironomidae,

Muscidae such as *Musca domestica, Muscina stabulans* and the like,

Calliphoridae,

Sarcophagidae,

Fanniidae,

Anthomyiidae such as *Delia platura, Delia antiqua* and the like,

Tephritidae,

Drosophilidae,

Psychodidae,

Simuliidae,

Tabanidae,

*Stomoxys* spp.,

Agromyzidae, and the like;

Coleoptera:

Corn rootworms such as *Diabrotica virgifera virgifera, Diabrotica undecimpunctata howardi* and the like, Scarabaeidae such as *Anomala cuprea, Anomala rufocuprea* and the like, Rhynchophoridae, Curculionidae and Bruchidae, such as *Sitophilus zeamais, Lissorhoptrus oryzophilus, Callosobruchus chienensis* and the like, Tenebrionidae such as *Tenebrio molitor, Tribolium castaneum* and the like, Chrysomelidae such as *Oulema oryzae, Aulacophora femoralis, Phyllotreta striolata, Leptinotarsa decemlineata* and the like, Anobiidae,

*Epilachna* spp. such as *Epilachna vigintioctopunctata* and the like,

Lyctidae,

Bostrychidae,

Cerambycidae,

*Paederus fuscipes*, and the like;

Blattaria: *Blattella germanica, Periplaneta fuliginosa, Periplaneta americana, Periplaneta brunnea, Blatta orientalis* and the like;

Thysanoptera: *Thrips palmi, Thrips tabaci, Frankliniella occidentalis, Frankliniella intonsa* and the like;

Hymenoptera:

Formicidae, Vespidae, Bethylidae,

Tenthredinidae such as *Athalia japonica*, and the like;

Orthoptera:

Gryllotalpidae, Acrididae, and the like;

Aphaniptera: *Ctenocephalides felis, Ctenocephalides canis, Pulex irritans, Xenopsylla cheopis*, and the like;

Anoplura: *Pediculus humanus corporis, Phthirus pubis, Haematopinus eurysternus, Dalmalinia ovis*, and the like;

Isoptera: *Reticulitermes speratus, Coptotermes formosanus*, and the like;

Acarina:

Tetranychidae such as *Tetranychus urticae, Tetranychus kanzawai, Panonychus citri, Panonychus ulmi, Oligonychus* spp. and the like, Eriophyidae such as *Aculops pelekassi, Aculus schlechtendali*, and the like, Tarsonemidae such as *Polyphagotarsonemus latus*, and the like, Tenuipalpidae, Tuckerellidae, Ixodidae such as *Haemaphysalis longicornis, Haemaphysalis flava, Dermacentor variabilis, Ixodes ovatus, Ixodes persulcatus, Boophilus microplus*, and the like, Acaridae such as *Tyrophagus putrescentiae*, and the like, Epidermoptidae such as *Dermatophagoides farinae, Dermatophagoides ptrenyssnus*, and the like, Cheyletidae such as *Cheyletus eruditus, Cheyletus malaccensis, Cheyletus moorei*, and the like, Dermanyssidae, and the like;

Araneae: *Chiracanthium japonicum, Latrodectus hasseltii*, and the like;

Chilopoda: *Thereuonema hilgendorfi, Scolopendra subspinipes*, and the like;

Diplopoda: *Oxidus gracilis, Nedyopus tambanus*, and the like;

Isopoda: *Armadillidium vulgare*, and the like;

Gastropoda: *Limax marginatus, Limax flavus*, and the like;

Nematoda: *Pratylenchus coffeae, Pratylenchus fallax, Heterodera glycines, Globodera rostochiensis, Meloidogyne hapla, Meloidogyne incognita*, and the like.

Although the pesticidal composition of the present invention may be the present compound itself, it is usually formulated into a preparation by mixing with a solid carrier, a liquid carrier and/or a gaseous carrier and, further, if necessary, adding a surfactant and other adjuvants for formulation. That is, the pesticidal composition of the present invention usually contains the present compound and further contains an inert carrier. Such a preparation includes an emulsion, an oil, a shampoo preparation, a flowable preparation, a powder, a wettable agent, a granule, a paste, a microcapsule, a foam, an aerosol, a carbon dioxide gas preparation, a tablet, and a resin preparation. These preparations may be used in the form of a poison bait, a pesticide coil, an electric pesticide mat, a smoking preparation, a fumigant, or a sheet.

A preparation of the pesticidal composition of the present invention contains usually 0.1 to 95% by weight of the present compound.

A solid carrier used for formulation includes finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.) or chemical fertilizers (e.g., ammonium sulfate, ammonium phosphate, ammonium nitrate, ammonium chloride, urea, etc.).

A liquid carrier includes aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), acid amides (e.g., N,N-dimethylformamide, N,N-dimethylacetamide, etc.), vegetable oil (e.g., soybean oil, cottonseed oil, etc.), vegetable essential oils (e.g., orange oil, hyssop oil, lemon oil, etc.), and water.

A gaseous carrier includes butane gas, chlorofluoro carbon gas, liquefied petroleum gas (LPG), dimethyl ether, and carbonic acid gas.

A surfactant includes alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

Other adjuvants for formulation include binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

A base material for a resin preparation includes polyvinyl chloride and polyurethane. A plasticizer such as phthalic acid ester (e.g., dimethyl phthalate, dioctyl phthalate, etc.), adipic acid ester or stearic acid may be added to these base materials, if necessary.

The resin preparation can be obtained by kneading the present compound into the base material by using a conventional kneader, followed by molding such as injection molding, extrusion molding or press molding. The resulting resin preparation may be formed into the shape of a plate, a film, a tape, a net, a string or the like via a further step of molding, cutting, or the like, if necessary. These resin preparations may be made into an animal collar, an animal ear tag, a sheet preparation, a lead, or a horticultural post.

A base material of a poison bait includes cereal powder, vegetable oil, sugar and crystalline cellulose. An antioxidant such as dibutylhydroxytoluene or nordihydroguaiaretic acid, a preservative such as dehydroacetic acid, an agent for preventing children or pets from erroneously eating such as hot pepper powder, and a pest-attractive perfume such as cheese perfume, onion perfume or peanut oil may be added to the base material, if necessary.

The pesticidal composition of the present invention is used by applying it to pests directly and/or habitats of pests (e.g., plants, animals, soil, etc.).

When the pesticidal composition of the present invention is used for controlling pests in agriculture and forestry, the application amount is usually 1 to 100,000 g/ha, preferably 10 to 1,000 g/ha of the active ingredient. When the pesticidal composition of the present invention is the form of an emulsion, a wettable agent, a flowable agent, or a microcapsule, it is usually used as a dilution with water containing 1 to 10,000 ppm of the active ingredient. When the pesticidal composition of the present invention is the form of powder or a granule, it is usually used as it is. These preparations may be sprayed as they are on plants to be protected from pests. In addition, soil can be treated with these preparations to control pests living in the soil. Seedbeds before planting or planting holes or plant feet on planting can be also treated with these preparations. Further, a sheet preparation of the pesticidal composition of the present invention may be applied by winding it around plants, locating it near plants, laying it on the soil surface at the plant feet, or the like.

When the pesticidal composition of the present invention is used for a control of pests of epidemic, the application amount is usually 0.001 to 100 mg/m$^3$ of the active ingredient for application to space, and 0.001 to 100 mg/m$^2$ of the active ingredient for application to a plane. The pesticidal composition in the form of an emulsion, wettable agent or a flowable agent is usually applied as a dilution with water containing 0.01 to 10,000 ppm of the active ingredient. The pesticidal composition in the form of an oil, an aerosol, a smoking preparation or a poison bait is usually applied as it is.

When the pesticidal composition of the present invention is used for controlling parasites living outside of a livestock such as a cow, a horse, a pig, a sheep, a goat or a chicken, or a small animal such as a dog, a cat, a rat or a mouse, it can be used for said animal by a known method in the veterinary filed. Specifically, when systemic control is intended, the pesticidal composition is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil or an aqueous liquid, washing an animal with the pesticidal composition in the form of a shampoo preparation, and attachment of a collar or a ear tag made of the pesticidal composition in the form of a resin preparation to an animal. When administered to an animal, the amount of the present compound is usually in the range of 0.01 to 1,000 mg per 1 kg body weight of the animal.

The pesticidal composition of the present invention may be used in admixture or combination with other insecticides, nematocides, acaricides, germicides, herbicides, plant growth regulators, synergists, fertilizers, soil conditioners, animal feed, and the like.

The active ingredient of such insecticide or acaricide includes pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin, and tefluthrin; organic phosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion; carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron, and triazuron; juvenile hormone-like substances such as pyriproxyfen, methoprene, hydroprene, and fenoxycarb; neonicotinoid compounds such as acetamiprid, nitenpyram, thiacloprid, thiamethoxam and dinotefuran; N-phenylpyrazole compounds such as acetoprole and ethiprole; benzoylhydrazine compounds such as tebufenozide, chromafenozide, methoxyfenozide and halofenozide; diafenthiuron; pymetrozine; flonicamid; triazamate; buprofezin; spinosad; emamectin benzoate; chlorfenapyr; indoxacarb MP; pyridalyl; cyromazine; fenpyroximate; tebufenpyrad; tolfenpyrad; pyridaben; pyrimidifen; fluacrypyrim; etoxazole; fenazaquin; acequinocyl; hexythiazox; clofentezine; fenbutatin oxide; dicofol, propargite; abamectin; milbemectin; amitraz; cartap; bensultap; thiocyclam; endosulfan; spirodiclofen; spiromesifen; and azadirachtin.

The active ingredient of such germicide includes strobilurin compounds such as azoxystrobin; organic phosphorus compounds such as tolclofos-methyl; azole compounds such as triflumizole, pefurazoate and difenoconazole; fthalide; flutolanil; validamycin; probenazole; diclomezine; pencycuron; dazomet; kasugamycin; IBP; pyroquilon; oxolinic acid; tricyclazole; ferimzone; mepronil; EDDP; isoprothiolane; carpropamid; diclocymet; furametpyr; fludioxonil; procymidone; and diethofencarb.

EXAMPLES

The present invention will be explained in more detail by the following Production Examples, Formulation Examples and Experimental Examples, but the present invention is not limited to them.

First, Production Examples of the present compound will be described.

Production Example 1

1.32 g of 3-t-butyl-5-(chloromethyl)-1H-pyrazole hydrochloride and 1.13 g of (3,3,3-trifluoropropyl)malononitrile were dissolved in 21 ml of N,N-dimethylformamide, and 1.93 g of potassium carbonate was then added under ice-cooling. The mixture was stirred at room temperature for 3 hours. After water was added, the reaction mixture was extracted with methyl-t-butyl ether. The organic layer was washed with water, dried over anhydrous magnesium sulfate, filtered, and then concentrated under reduced pressure. The residue was recrystallized from hexane-ethyl acetate to obtain 1.35 g of a compound represented by the following formula:

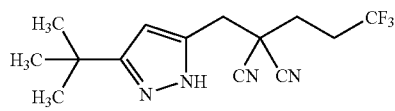

(hereinafter, referred to as the present compound (1)).

$^1$H-NMR (CDCl$_3$, TMS, δ (ppm)): 1.32 (9H, s), 2.18-2.27 (2H, m), 2.44-2.59 (2H, m), 3.34 (2H, s), 6.16 (1H, s), 10.19 (1H, br. s)

Production Example 2

2.52 g of 5-(chloromethyl)-3-t-butyl-1-methyl-1H-pyrazole hydrochloride and 1.83 g of (3,3,3-trifluoropropyl)malononitrile were dissolved in 25 ml of N,N-dimethylformamide, and 3.12 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered, and then concentrated under reduced pressure. The residue was recrystallized from hexane-ethyl acetate to obtain 0.44 g of a compound represented by the following formula:

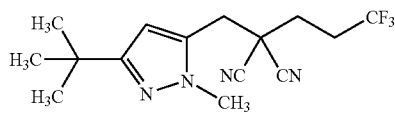

(hereinafter, referred to as the present compound (2)).

$^1$H-NMR (CDCl$_3$, TMS, δ (ppm)): 1.30 (9H, s), 2.25-2.29 (2H, m), 2.49-2.61 (2H, m), 3.34 (2H, s), 3.85 (3H, s), 6.23 (1H, s)

Production Example 3

2.13 g of 3-t-butyl-5-(chloromethyl)-1-(2,2,2-trifluoroethyl)-1H-pyrazole hydrochloride and 1.18 g of (3,3,3-trifluoropropyl)malononitrile were dissolved in 21 ml of N,N-dimethylformamide, and 2.02 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered, and then concentrated under reduced pressure. The residue was subjected to silica gel column chromatography to obtain 1.49 g of a compound represented by the following formula:

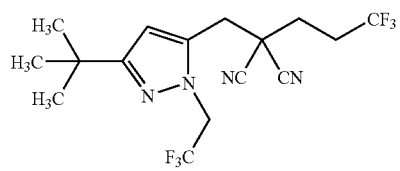

(hereinafter, referred to as the present compound (3)).

$^1$H-NMR (CDCl$_3$, TMS, δ (ppm)): 1.39 (9H, s), 2.26-2.29 (2H, m), 2.45-2.56 (2H, m), 3.29 (2H, s), 4.77 (2H, q), 6.17 (1H, s)

Production Example 4

1.12 g of 3-t-butyl-5-(chloromethyl)isoxazole and 1.30 g of (3,3,3-trifluoropropyl)malononitrile were dissolved in 24 ml of N,N-dimethylformamide, and 2.21 g of potassium carbonate was then added under ice-cooling. The mixture was stirred at room temperature for 3 hours. After water was added, the reaction mixture was extracted with methyl-t-butyl ether. The organic layer was washed with water, dried over anhydrous magnesium sulfate, filtered, and then concentrated under reduced pressure. The residue was subjected to silica gel column chromatography and then recrystallized from hexane-ethyl acetate to obtain 0.55 g of a compound represented by the following formula:

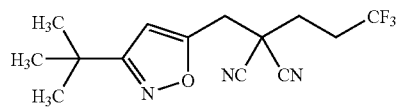

(hereinafter, referred to as the present compound (4)).

$^1$H-NMR (CDCl$_3$, TMS, δ (ppm)): 1.35 (9H, s), 2.26-2.29 (2H, m), 2.48-2.60 (2H, m), 3.48 (2H, s), 6.35 (1H, s)

Production Example 5

1.36 g of 3-t-butyl-5-(chloromethyl)isothiazole and 1.37 g of (3,3,3-trifluoropropyl)malononitrile were dissolved in 27 ml of N,N-dimethylformamide, and 2.35 g of potassium carbonate was then added under ice-cooling. The mixture was stirred at room temperature for 5 hours. After water was added, the reaction mixture was extracted with methyl-t-butyl ether. The organic layer was washed with water, dried over anhydrous magnesium sulfate, filtered, and then concentrated under reduced pressure. The residue was subjected to silica gel column chromatography and then recrystallized from hexane-ethyl acetate to obtain 0.89 g of a compound represented by the following formula:

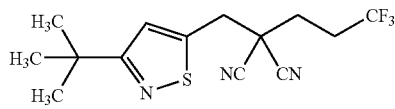

(hereinafter, referred to as the present compound (5)).
$^1$H-NMR (CDCl$_3$, TMS, δ (ppm)): 1.34 (9H, s), 2.26-2.30 (2H, m), 2.49-2.61 (2H, m), 3.38 (2H, s), 6.11 (1H, s)

Production Example 6

0.69 g of 5-t-butyl-3-(chloromethyl)isoxazole and 0.65 g of (3,3,3-trifluoropropyl)malononitrile were dissolved in 12 ml of N,N-dimethylformamide, and 1.11 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered, and then concentrated under reduced pressure. The residue was subjected to silica gel column chromatography and then recrystallized from hexane-ethyl acetate to obtain 0.36 g of a compound represented by the following formula:

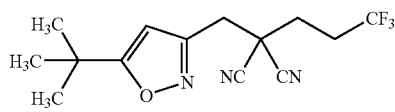

(hereinafter, referred to as the present compound (6)).
$^1$H-NMR (CDCl$_3$, TMS, δ (ppm)): 1.37 (9H, s), 2.25-2.29 (2H, m), 2.49-2.60 (2H, m), 3.38 (2H, s), 6.10 (1H, s)

Production Example 7

0.91 g of 1-t-butyl-4-(chloromethyl)-1H-pyrazole hydrochloride and 0.81 g of (3,3,3-trifluoropropyl)malononitrile were dissolved in 10 ml of N,N-dimethylformamide, and 1.38 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography and then recrystallized from hexane-ethyl acetate to obtain 0.34 g of a compound represented by the following formula:

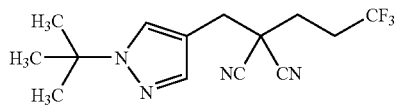

(hereinafter, referred to as the present compound (7)).

$^1$H-NMR (CDCl$_3$, TMS; δ (ppm)): 1.60 (9H, s), 2.17-2.21 (2H, m), 2.48-2.57 (2H, m), 3.20 (2H, s), 7.55 (1H, s), 7.61 (1H, s)

Production Example 8

2.39 g of 1-benzyl-4-(chloromethyl)-1H-pyrazole hydrochloride and 1.59 g of (3,3,3-trifluoropropyl)malononitrile were dissolved in 30 ml of N,N-dimethylformamide, and 2.76 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography and then recrystallized with hexane-ethyl acetate to obtain 1.94 g of a compound represented by the following formula:

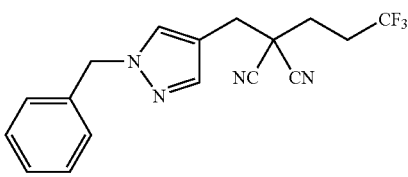

(hereinafter, referred to as the present compound (8)).
$^1$H-NMR (CDCl$_3$, TMS, δ (ppm)): 2.15-2.91 (2H, m), 2.44-2.56 (2H, m), 3.18 (2H, s), 5.32 (2H, s), 7.21-7.23 (2H, m), 7.30-7.38 (3H, m), 7.48 (1H, s), 7.57 (1H, s).

Production Example 9

1.04 g of 2-t-butyl-4-(chloromethyl)-1,3-oxazole and 0.97 g of (3,3,3-trifluoropropyl)malononitrile were dissolved in 24 ml of N,N-dimethylformamide, and 1.66 g of potassium carbonate was then added under ice-cooling. The mixture was stirred at room temperature for 3 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.64 g of a compound represented by the following formula:

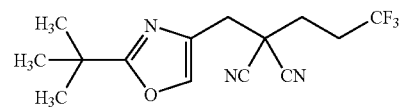

(hereinafter, referred to as the present compound (9)).
$^1$H-NMR (CDCl$_3$, TMS, δ (ppm)): 1.32 (9H, s), 2.31-2.35 (2H, m), 2.51-2.60 (2H, m), 3.25 (2H, s), 7.64 (1H, s)

Production Example 10

1.02 g of 4-(chloromethyl)-1,3-thiazole hydrochloride and 0.97 g of (3,3,3-trifluoropropyl)malononitrile were dissolved in 18 ml of N,N-dimethylformamide, and 1.66 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.93 g of a compound represented by the following formula:

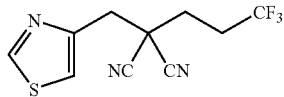

(hereinafter, referred to as the present compound (10)).
$^1$H-NMR (CDCl$_3$, TMS, δ (ppm)): 2.29-2.34 (2H, m), 2.52-2.63 (2H, m), 3.56 (2H, s), 7.45 (1H, s), 8.86 (1H, s)

Production Example 11

0.48 g of 4-(chloromethyl)-2-methyl-1,3-thiazole and 0.42 g of (3,3,3-trifluoropropyl)malononitrile were dissolved in 10 ml of N,N-dimethylformamide, and 0.74 g of potassium carbonate was then added under stirring and ice-cooling. The mixture was further stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.14 g of a compound represented by the following formula:

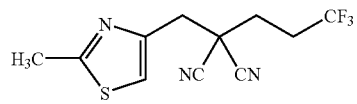

(hereinafter, referred to as the present compound (11)).
$^1$H-NMR (CDCl$_3$, TMS, δ (ppm)): 2.29-2.33 (2H, m), 2.50-2.62 (2H, m), 2.72 (3H, s), 3.44 (2H, s), 7.21 (1H, s)

Production Example 12

0.48 g of 2-t-butyl-4-(chloromethyl)-1,3-thiazole and 0.45 g of (3,3,3-trifluoropropyl)malononitrile were dissolved in 10 ml of N,N-dimethylformamide, and 0.39 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered, and then concentrated under reduced pressure. The residue was subjected to silica gel column chromatography to obtain 0.54 g of a compound represented by the following formula:

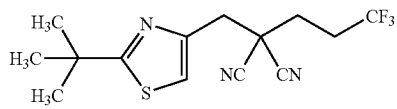

(hereinafter, referred to as the present compound (12)).
$^1$H-NMR (CDCl$_3$, TMS, δ (ppm)): 1.42 (9H, s), 2.30-2.34 (2H, m), 2.52-2.64 (2H, m), 3.44 (2H, s), 7.18 (1H, s)

Production Example 13

0.56 g of 2-chloro-4-(chloromethyl)-1,3-thiazole and 0.48 g of (3,3,3-trifluoropropyl)malononitrile were dissolved in 20 ml of N,N-dimethylformamide, and 0.88 g of potassium carbonate was then added under ice-cooling. The mixture was further stirred at room temperature for 5 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.63 g of a compound represented by the following formula:

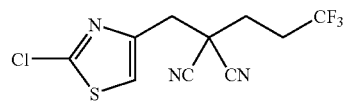

(hereinafter, referred to as the present compound (13)).
$^1$H-NMR (CDCl$_3$, TMS, δ (ppm)): 2.28-2.35 (2H, m), 2.50-2.63 (2H, m), 3.42 (2H, s), 7.31 (1H, s)

Production Example 14

In a similar manner to Production Example 13, 0.08 g of a compound represented by the following formula:

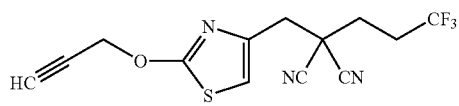

(hereinafter, referred to as the present compound (14)) was obtained using 0.3 g of 4-(chloromethyl)-2-(propargyloxy)-1,3-thiazole, 0.29 g of (3,3,3-trifluoropropyl)malononitrile, 10 ml of N,N-dimethylformamide and 0.54 g of potassium carbonate.
$^1$H-NMR (CDCl$_3$, TMS, δ (ppm)): 2.31-2.38 (2H, m), 2.55 (1H, s), 2.46-2.61 (2H, m), 3.43 (2H, s), 5.01 (2H, s), 6.75 (1H, s)

Production Example 15

0.66 g of 5-(chloromethyl)-2-methyl-1,3-thiazole hydrochloride and 0.60 g of (3,3,3-trifluoropropyl)malononitrile were dissolved in 15 ml of N,N-dimethylformamide, and 1.02 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.52 g of a compound represented by the following formula:

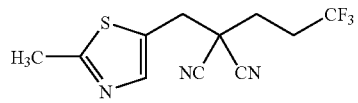

(hereinafter, referred to as the present compound (15)).

¹H-NMR (CDCl₃, TMS, δ (ppm)): 2.29-2.33 (2H, m), 2.50-2.60 (2H, m), 2.74 (3H, s), 3.50 (2H, s), 7.62 (1H, s)

Production Example 16

0.58 g of 5-(chloromethyl)-2-ethyl-1,3-thiazole hydrochloride and 0.49 g of (3,3,3-trifluoropropyl)malononitrile were dissolved in 12 ml of N,N-dimethylformamide, and 0.83 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.45 g of a compound represented by the following formula:

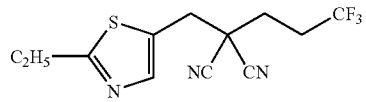

(hereinafter, referred to as the present compound (16)).
¹H-NMR (CDCl₃, TMS, δ (ppm)): 1.41 (3H, t), 2.22-2.26 (2H, m), 2.49-2.61 (2H, m), 3.05 (2H, q), 3.52 (2H, s), 7.64 (1H, s)

Production Example 17

1.41 g of 2-t-butyl-5-(chloromethyl)-1,3-thiazole hydrochloride and 0.81 g of (3,3,3-trifluoropropyl)malononitrile were dissolved in 15 ml of N,N-dimethylformamide, and 1.38 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.86 g of a compound represented by the following formula:

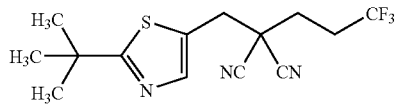

(hereinafter, referred to as the present compound (17)).
¹H-NMR (CDCl₃, TMS, δ (ppm)): 1.46 (9H, s), 2.22-2.27 (2H, m), 2.49-2.61 (2H, m), 3.52 (2H, s), 7.64 (1H, s)

Production Example 18

0.50 g of 2-chloro-5-(chloromethyl)-1,3-thiazole and 0.49 g of (3,3,3-trifluoropropyl)malononitrile were dissolved in 10 ml of N,N-dimethylformamide, and 0.83 g of potassium carbonate was then added under ice-cooling. The mixture was stirred at room temperature overnight. After aqueous saturated sodium chloride was added, the reaction mixture was extracted with methyl-t-butyl ether. The organic layer was washed with aqueous saturated sodium chloride, dried over anhydrous sodium sulfate and then concentrated under reduced pressure. The residue was recrystallized from hexane-methyl-t-butyl ether to obtain 0.53 g of a compound represented by the following formula:

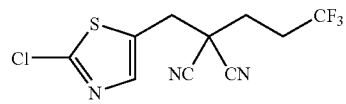

(hereinafter, referred to as the present compound (18)).
¹H-NMR (CDCl₃, TMS, δ (ppm)): 2.20-2.30 (2H, m), 2.50-2.63 (2H, m), 3.49 (2H, s), 7.60 (1H, s)

Production Example 19

Under a nitrogen atmosphere, 0.75 g of {[2-(propargyloxy)-1,3-thiazol-5-yl]methyl}malononitrile and 0.82 g of 1,1,1-trifluoro-3-iodopropane were dissolved in 20 ml of N,N-dimethylformamide, and 0.60 g of potassium carbonate was then added at room temperature. The mixture was stirred at room temperature for 5 hours. After aqueous saturated sodium chloride was added, the reaction mixture was extracted with methyl-t-butyl ether. The organic layer was washed with aqueous saturated sodium chloride, dried over anhydrous sodium sulfate and then concentrated under reduced pressure. The residue was recrystallized from hexane/methyl-t-butyl ether to obtain 0.80 g of a compound represented by the following formula:

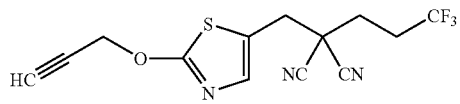

(hereafter, referred to as the present compound (19)).
¹H-NMR (CDCl₃, TMS, δ (ppm)): 2.20-2.30 (2H, m), 2.50-2.65 (2H, m), 2.60 (1H, s), 3.40 (2H, s), 5.07 (2H, s), 7.16 (1H, s)

Production Example 20

In a similar manner to Production Example 13, 0.17 g of a compound represented by the following formula:

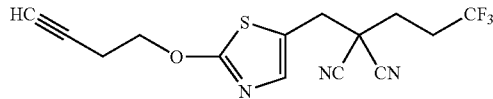

(hereinafter, referred to as the present compound (20)) was obtained using 0.21 g of 2-(3-butynyl-1-oxy)-5-(chloromethyl)-1,3-thiazole, 0.26 g of (3,3,3-trifluoropropyl)malononitrile, 10 ml of N,N-dimethylformamide and 0.35 g of potassium carbonate.
¹H-NMR (CDCl₃, TMS, δ (ppm)): 2.05 (1H, s), 2.20-2.28 (2H, m), 2.48-2.60 (2H, m), 2.70-2.76 (2H, m), 3.38 (2H, s), 4.53 (2H, t), 7.12 (1H, s)

Production Example 21

0.76 g of 3-t-butyl-5-(chloromethyl)-1,2,4-thiadiazole hydrochloride and 0.71 g of (3,3,3-trifluoropropyl)malononitrile were dissolved in 15 ml of N,N-dimethylformamide, and 1.20 g of potassium carbonate was then added under ice-cooling. The mixture was stirred at room temperature for 10 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.66 g of a compound represented by the following formula:

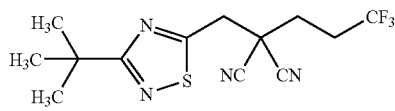

(hereinafter, referred to as the present compound (21)).
$^1$H-NMR (CDCl$_3$, TMS, δ (ppm)): 1.45 (9H, s), 2.44-2.48 (2H, m), 2.55-2.64 (2H, m), 3.79 (2H, s)

Production Example 22

0.87 g of 2-t-butyl-5-(chloromethyl)-1,3,4-oxadiazole and 0.89 g of (3,3,3-trifluoropropyl)malononitrile were dissolved in 15 ml of N,N-dimethylformamide, and 1.38 g of potassium carbonate was then added under ice-cooling. The mixture was stirred at room temperature for 10 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.88 g of a compound represented by the following formula:

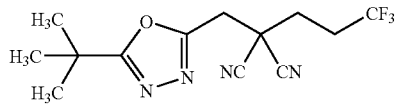

(hereinafter, referred to as the present compound (22)).
$^1$H-NMR (CDCl$_3$, TMS, δ (ppm)): 1.45 (9H, s), 2.39-2.46 (2H, m), 2.51-2.63 (2H, m), 3.62 (2H, s)

Production Example 23

0.57 g of 3-(chloromethyl)-5-ethyl-1,2,4-oxadiazole and 0.65 g of (3,3,3-trifluoropropyl)malononitrile were dissolved in 20 ml of N,N-dimethylformamide, and 0.62 g of potassium carbonate was then added under ice-cooling. The mixture was stirred at room temperature for 4 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.78 g of a compound represented by the following formula:

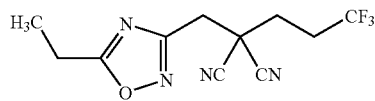

(hereinafter, referred to as the present compound (23)).
$^1$H-NMR (CDCl$_3$, TMS, δ(ppm): 1.44 (3H, t), 2.40-2.49 (2H, m), 2.50-2.63 (2H, m), 2.97 (2H, q), 3.50 (2H, s)

Production Example 24

1.50 g of 5-t-butyl-3-(chloromethyl)-1,2,4-oxadiazole and 1.40 g of (3,3,3-trifluoropropyl)malononitrile were dissolved in 50 ml of N,N-dimethylformamide, and 2.40 g of potassium carbonate was then added under ice-cooling. The mixture was stirred at room temperature for 4 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.88 g of a compound represented by the following formula:

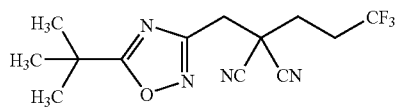

(hereafter, referred to as the present compound (24)).
$^1$H-NMR (CDCl$_3$, TMS, δ (ppm)): 1.44 (9H, s), 2.40-2.45 (2H, m), 2.50-2.65 (2H, m), 3.47 (2H, s)

Production Example 25

0.97 g of 5-(1-methylcyclopropyl)-3-(chloromethyl)-1,2,4-oxadiazole and 0.64 g of (3,3,3-trifluoropropyl)malononitrile were dissolved in 20 ml of N,N-dimethylformamide, and 0.86 g of potassium carbonate was then added under ice-cooling. The mixture was stirred at room temperature for 4 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.33 g of a compound represented by the flowing formula:

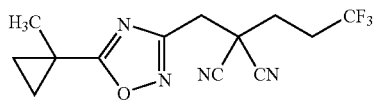

(hereinafter, referred to as the present compound (25)).
$^1$H-NMR (CDCl$_3$, TMS, δ (ppm)): 1.09 (2H, m), 1.45 (2H, m), 1.57 (3H, s), 2.30-2.45 (2H, m), 2.45-2.63 (2H, m), 3.42 (2H, s)

Production Example 26

0.21 g of 5-(2,2-dimethylpropyl)-3-(chloromethyl)-1,2,4-oxadiazole and 0.19 g of (3,3,3-trifluoropropyl)malononitrile were dissolved in 10 ml of N,N-dimethylformamide, and 0.17 g of potassium carbonate was then added under ice-cooling. The mixture was stirred at room temperature for 4 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.18 g of a compound represented by the following the formula:

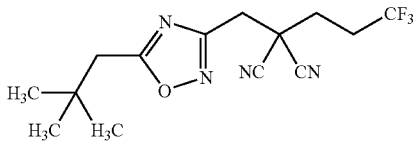

(hereinafter, referred to as the present compound (26)).
$^1$H-NMR (CDCl$_3$, TMS, δ (ppm)): 0.98 (9H, s), 2.29-2.38 (2H, m), 2.42-2.55 (2H, m), 2.77 (2H, s), 3.42 (2H, s)

Production Example 27

0.71 g of 1-bromo-3,3,3-trifluoropropane and 0.77 g of [1-(1-t-butyl-1H-pyrazol-4-yl)ethyl]malononitrile were dissolved in 4 ml of N,N-dimethylformamide, and 0.55 g of potassium carbonate and 0.66 g of potassium iodide were then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.49 g of a compound represented by the following formula:

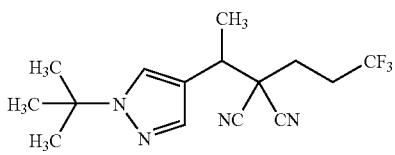

(hereinafter, referred to as the present compound (27)).
$^1$H-NMR (CDCl$_3$, TMS, δ(ppm): 1.61 (9H, s), 1.65 (3H, d), 2.04-2.09 (2H, m), 2.42-2.53 (2H, m), 3.25 (1H, q), 7.51 (1H, s), 7.55 (1H, s)

Production Example 28

1.52 g of 2-(chloromethyl)-8-methylimidazo[1,2-a]pyridine and 1.36 g of (3,3,3-trifluoropropyl)malononitrile were dissolved in 20 ml of N,N-dimethylformamide, and 1.16 g of potassium carbonate was then added under ice-cooling. The mixture was stirred at room temperature for 7 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography and then recrystallized form hexane-ethyl acetate to obtain 1.50 g of a compound represented by the following formula:

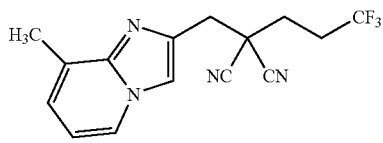

(hereinafter, referred to as the present compound (28)).
$^1$H-NMR (CDCl$_3$, TMS, δ (ppm)): 2.38-2.42 (2H, m), 2.54-2.66 (2H, m), 2.57 (3H, s), 3.53 (2H, s), 6.73 (1H, t), 7.00 (1H, dd), 7.66 (1H, s), 7.97 (1H, d)

Production Example 29

1.67 g of 2-(chloromethyl)-5-methylimidazo[1,2-a]pyridine and 1.49 g of (3,3,3-trifluoropropyl)malononitrile were dissolved in 25 ml of N,N-dimethylformamide, and 2.54 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography and then recrystallized from hexane-ethyl acetate to obtain 1.92 g of a compound represented by the following formula:

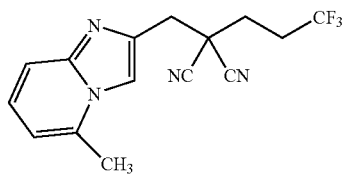

(hereinafter, referred to as the present compound (29)).
$^1$H-NMR (CDCl$_3$, TMS, δ (ppm)): 2.37-2.41 (2H, m), 2.51-2.63 (2H, m), 2.57 (3H, s), 3.63 (2H, s), 6.67 (1H, dd), 7.19 (1H, dd), 7.48 (1H, d), 7.56 (1H, s)

Production Example 30

2.15 g of 4-(chloromethyl)-1-cyclohexyl-1H-pyrazole hydrochloride and 1.50 g of (3,3,3-trifluoropropyl)malononitrile were dissolved in 20 ml of N,N-dimethylformamide, and 2.63 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 1.98 g of a compound represented by the following formula:

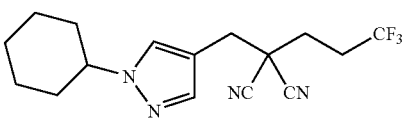

(hereinafter, referred to as the present compound (30)).
$^1$H-NMR (CDCl$_3$, TMS, δ (ppm)): 1.24-1.28 (2H, m), 1.31-1.45 (2H, m), 1.70-1.76 (2H, m), 1.88-1.92 (1H, m), 2.15-2.20 (3H, m), 2.34-2.37 (1H, m), 2.46-2.54 (3H, m), 3.19 (2H, s), 4.09-4.13 (1H, m), 7.51 (1H, s), 7.52 (1H, s)

Production Example 31

0.73 g of [(1-propargyl-1H-pyrazol-4-yl)methyl]malononitrile and 1.39 g of 1-iodo-3,3,3-trifluoropropane were dissolved in 4 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography and then recrystallized from hexane-ethyl acetate to obtain 0.45 g of a compound represented by the following formula:

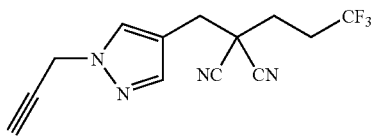

(hereinafter, referred to as the present compound (31)).
$^{1}$H-NMR (CDCl$_3$, TMS, δ (ppm)): 2.17-2.22 (2H, m), 2.47-2.58 (3H, m), 3.21 (2H, s), 4.97 (2H, d), 7.58 (1H, s), 7.75 (1H, s)

Production Example 32

0.14 g of 2-methylallyl chloride and 0.30 g of 2-(1-t-butyl-1H-pyrazol-4-ylmethyl)malononitrile were dissolved in 1 ml of N,N-dimethylformamide, and 0.22 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.21 g of a compound represented by the following formula:

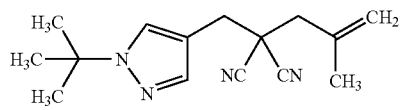

(hereinafter, referred to as the present compound (32)).
$^{1}$H-NMR (CDCl$_3$, TMS, δ (ppm)): 1.58 (9H, s), 1.59 (3H, s), 2.62 (2H, s), 3.15 (2H, s), 5.08 (1H, s), 5.17 (1H, s), 7.55 (1H, s), 7.61 (1H, s)

Production Example 33

0.26 g of 3-bromocyclohexene and 0.30 g of [(1-t-butyl-1H-pyrazol-4-yl)methyl]malononitrile were dissolved in 1 ml of N,N-dimethylformamide, and 0.22 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.11 g of a compound represented by the following formula:

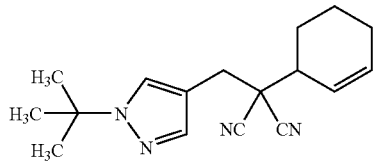

(hereinafter, referred to as the present compound (33)).
$^{1}$H-NMR (CDCl$_3$, TMS, δ (ppm)): 1.57-1.64 (3H, m), 1.59 (9H, s), 1.87-1.98 (1H, m), 2.04-2.15 (2H, m), 2.68 (1H, b. s.), 3.16 (2H, s), 5.74-5.76 (1H, m), 6.10-6.13 (1H, m), 7.54 (1H, s), 7.65 (1H, s)

Production Example 34

1.42 g of 4-(chloromethyl)-5-(1H-pyrrol-1-yl)-1-t-butyl-1H-pyrazole and 0.97 g of (3,3,3-trifluoropropyl)malononitrile were dissolved in 12 ml of N,N-dimethylformamide, and 0.83 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 2.20 g of a compound represented by the following formula:

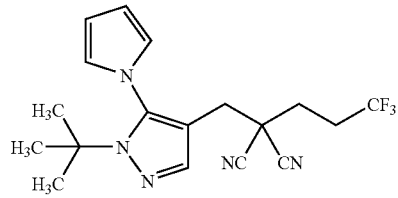

(hereinafter, referred to as the present compound (34)).
$^{1}$H-NMR (CDCl$_3$, TMS, δ (ppm)): 1.43 (9H, s), 2.04-2.11 (2H, m), 2.38-2.49 (2H, m), 2.79 (2H, s), 6.35 (2H, t), 6.73 (2H, t), 7.73 (1H, s)

Production Example 35

0.47 g of 3-(bromomethyl)-5-trifluoromethylisoxazole and 0.32 g of (3,3,3-trifluoropropyl)malononitrile were dissolved in 4 ml of N,N-dimethylformamide, and 0.28 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.36 g of a compound represented by the following formula:

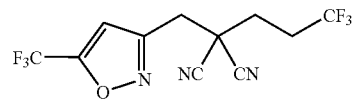

(hereinafter, referred to as the present compound (35)).
$^1$H-NMR (CDCl$_3$, TMS, δ (ppm)): 2.29-2.34 (2H, m), 2.51-2.63 (2H, m), 3.51 (2H, s), 6.91 (1H, s)

Production Example 36

1.14 g of 3-(1-bromoethyl)-5-trifluoromethylisoxazole and 0.76 g of (3,3,3-trifluoropropyl)malononitrile were dissolved in 8 ml of N,N-dimethylformamide, and 0.65 g of potassium carbonate was added to the stirred solution under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.41 g of a compound represented by the following formula:

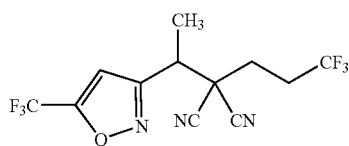

(hereinafter, referred to as the present compound (36)).
$^1$H-NMR (CDCl$_3$, TMS, δ (ppm)): 1.75 (3H, d), 2.12-2.20 (2H, m), 2.51-2.58 (2H, m), 3.64 (1H, q), 6.89 (1H, s)

Production Example 37

1.00 g of 3-(1-bromopropyl)-5-trifluoromethylisoxazole and 0.62 g of (3,3,3-trifluoropropyl)malononitrile were dissolved in 8 ml of N,N-dimethylformamide, and 0.53 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.31 g of a compound represented by the following formula:

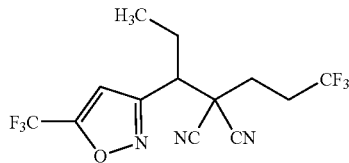

(hereinafter, referred to as the present compound (37)).
$^1$H-NMR (CDCl$_3$, TMS, δ (ppm)): 0.94 (3H, t), 1.99-2.19 (3H, m), 2.29-2.35 (1H, m), 2.43-2.61 (2H, m), 3.37 (1H, dd), 6.88 (1H, s)

Production Example 38

1.70 g of 3-(bromomethyl)-5-pentafluoroethylisoxazole and 1.20 g of (3,3,3-trifluoropropyl)malononitrile were dissolved in 15 ml of N,N-dimethylformamide, and 1.02 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 1.71 g of a compound represented by the following formula:

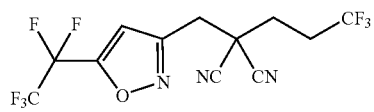

(hereinafter, referred to as the present compound (38)).
$^1$H-NMR (CDCl$_3$, TMS, δ (ppm)): 2.30-2.34 (2H, m), 2.52-2.63 (2H, m), 3.52 (2H, s), 6.96 (1H, s)

Production Example 39

0.46 g of 3-(chloromethyl)-5-(heptafluoropropyl)isoxazole and 0.26 g of (3,3,3-trifluoropropyl)malononitrile were dissolved in 2 ml of N,N-dimethylformamide, and 0.22 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.27 g of a compound represented by the following formula:

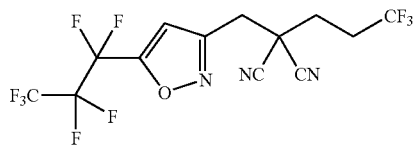

(hereinafter, referred to as the present compound (39)).
$^1$H-NMR (CDCl$_3$, TMS, δ (ppm)): 2.29-2.33 (2H, m), 2.51-2.63 (2H, m), 3.53 (2H, s), 6.96 (1H, s)

Production Example 40

0.44 g of (5-i-propyl-isoxazol-3-yl)methyl 4-toluenesulfonate and 0.24 g of (3,3,3-trifluoropropyl)malononitrile were dissolved in 3 ml of N,N-dimethylformamide, and 0.25 g of potassium iodide and 0.21 g of potassium carbonate were added. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.27 g of a compound represented by the following formula:

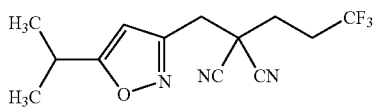

(hereinafter, referred to as the present compound (40)).

$^1$H-NMR (CDCl$_3$, TMS, δ (ppm)): 1.33 (6H, d), 2.25-2.29 (2H, m), 2.49-2.60 (2H, m), 3.08 (1H, m), 3.39 (2H, s), 6.13 (1H, s)

Production Example 41

0.39 g of 3-(1-chloroethyl)-5-i-propylisoxazole and 0.36 g of (3,3,3-trifluoropropyl)malononitrile were dissolved in 2 ml of N,N-dimethylformamide, and 0.30 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.31 g of a compound represented by the formula:

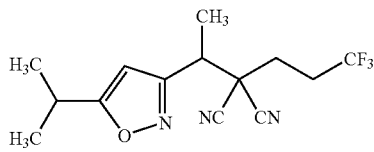

(hereinafter, referred to as the present compound (41)).

$^1$H-NMR (CDCl$_3$, TMS, δ (ppm)): 1.32 (6H, d), 1.60 (3H, d), 2.07-2.17 (2H, m), 2.42-2.62 (2H, m), 3.07 (1H, m), 3.49 (1H, q), 6.10 (1H, s)

Production Example 42

1.50 g of 3-(1-chloroethyl)-5-t-butylisoxazole and 0.76 g of (3,3,3-trifluoropropyl)malononitrile were dissolved in 5 ml of N,N-dimethylformamide, and 0.78 g of potassium iodide and 0.65 g of potassium carbonate were then added under ice-cooling. The mixture was further stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.75 g of a compound represented by the following formula:

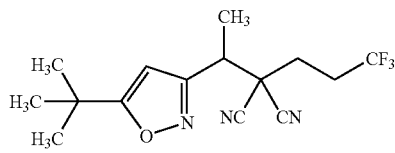

(hereinafter, referred to as the present compound (42)).

$^1$H-NMR (CDCl$_3$, TMS, δ (ppm)): 1.37 (9H, s), 1.60 (3H, d), 2.11-2.18 (2H, m), 2.44-2.64 (2H, m), 3.49 (1H, q), 6.08 (1H, s)

Production Example 43

4.34 g of 3-(1-bromomethyl)-5-(t-butyldimethylsilanyloxymethyl)isoxazole and 2.76 g of (3,3,3-trifluoropropyl)malononitrile were dissolved in 17 ml of N,N-dimethylformamide, and 2.35 g of potassium carbonate was added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 6.11 g of a compound represented by the following formula:

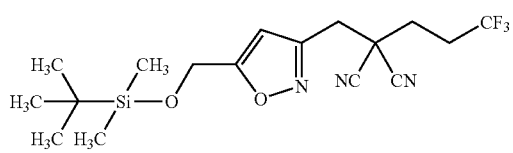

(hereinafter, referred to as the present compound (43)).

$^1$H-NMR (CDCl$_3$, TMS, δ (ppm)): 0.12 (6H, s), 0.94 (9H, s), 2.24-2.28 (2H, m), 2.48-2.60 (2H, m), 3.42 (2H, s), 4.81 (2H, s), 6.38 (1H, s)

Production Example 44

6.40 g of [(5-(t-butyldimethylsilanyloxymethyl)isoxazol-3-yl)methyl](3,3,3-trifluoropropyl)malononitrile was dissolved in 50 ml of tetrahydrofuran and 17 ml of a 1 M solution of tetrabutylammonium fluoride in tetrahydrofuran was added under ice-cooling. The mixture was stirred at room temperature for 4 hours. After aqueous saturated sodium hydrogen carbonate was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 2.97 g of a compound represented by the following formula:

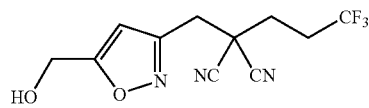

(hereinafter, referred to as the present compound (44)).

$^1$H-NMR (CDCl$_3$, TMS, δ (ppm)): 2.07 (1H, t), 2.26-2.30 (2H, m), 2.49-2.61 (2H, m), 3.43 (2H, s), 4.83 (2H, d), 6.46 (1H, d)

Production Example 45

0.27 g of the present compound (44) was dissolved in 1.5 ml of dichloromethane and stirred under ice-cooling. To the solution, 0.18 g of dimethylamino)sulfur trifluoride was added and then stirred at room temperature for 4 hours. After aqueous saturated sodium hydrogen carbonate was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.20 g of a compound represented by the following formula:

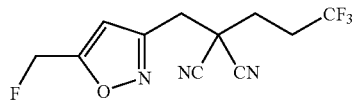

(hereinafter, referred to as the present compound (45)).
¹H-NMR (CDCl₃, TMS, δ (ppm)): 2.28-2.31 (2H, m), 2.50-2.61 (2H, m), 3.49 (2H, s), 5.42 (2H, d), 6.60 (1H, d)

Production Example 46

2.04 g of {[5-(hydroxymethyl)isoxazol-3-yl]methyl}(3,3,3-trifluoropropyl)malononitrile was dissolved in 75 ml of 1,4-dioxane, and 3.25 g of manganese dioxide was then added. The mixture was stirred and heated under reflux for 6 hours. The reaction mixture was cooled to room temperature and filtered through Celite®. The filtrate was concentrated under reduced pressure, and the residue was subjected to silica gel column chromatography to obtain 1.17 g of a compound represented by the following formula:

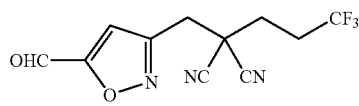

(hereinafter, referred to as the present compound (46)).
¹H-NMR (CDCl₃, TMS, δ (ppm)): 2.29-2.34 (2H, m), 2.51-2.63 (2H, m), 3.51 (2H, s), 7.16 (1H, s), 10.03 (1H, s)

Production Example 47

0.27 g of the present compound (46) was dissolved in 5 ml of dichloromethane and stirred under ice-cooling. To the solution, 0.33 g of (dimethylamino)sulfur trifluoride was added and then stirred at room temperature overnight. After aqueous saturated sodium hydrogen carbonate was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.14 g of a compound represented by the formula:

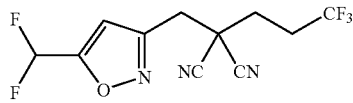

(hereinafter, referred to as the present compound (47)).
¹H-NMR (CDCl₃, TMS, δ (ppm)): 2.28-2.32 (2H, m), 2.51-2.60 (2H, m), 3.49 (2H, s), 6.66-6.93 (2H, m)

Production Example 48

3.60 g of {5-[1-(t-butyldimethylsilanyloxy)ethyl]isoxazol-3-yl}methyl 4-toluenesulfonate and 1.43 g of (3,3,3-trifluoropropyl)malononitrile were dissolved in 10 ml of N,N-dimethylformamide, and 1.46 g of potassium iodide and 1.22 g of potassium carbonate were then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 2.65 g of a compound represented by the following formula:

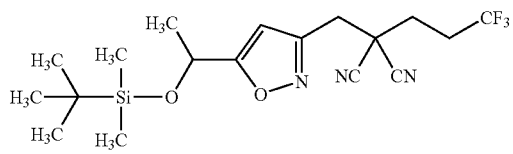

(hereinafter, referred to as the present compound (48)).
¹H-NMR (CDCl₃, TMS, δ (ppm)): 0.08 (3H, s), 0.11 (3H, s), 0.90 (9H, s), 1.54 (3H, d), 2.25-2.28 (2H, m), 2.52-2.60 (2H, m), 3.41 (2H, s), 4.97 (1H, q), 6.32 (1H, s)

Production Example 49

2.54 g of the present compound (48) was dissolved in 20 mlg of tetrahydrofuran, and 7 ml of a 1 M solution of tetrabutylammonium fluoride in tetrahydrofuran was added. The mixture was stirred at room temperature for 4 hours. After aqueous saturated sodium hydrogen carbonate was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 1.35 g of a compound represented by the following formula:

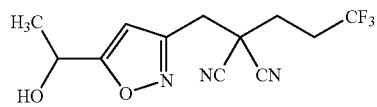

(hereinafter, referred to as the present compound (49)).
¹H-NMR (CDCl₃, TMS, δ (ppm)): 1.62 (3H, d), 2.26-2.30 (2H, m), 2.49-2.58 (2H, m), 3.42 (2H, s), 5.04 (1H, q), 6.40 (1H, s)

Production Example 50

0.32 g of the present compound (49) was dissolved in 5 ml of dichloromethane and stirred under ice-cooling. To the solution, 0.21 g of (dimethylamino)sulfur trifluoride was added and then stirred at room temperature for 4 hours. After aqueous saturated sodium hydrogen carbonate was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.21 g of a compound represented by the flowing formula:

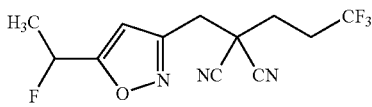

(hereinafter, referred to as the present compound (50)).
$^1$H-NMR (CDCl$_3$, TMS, δ (ppm)): 1.73-1.79 (3H, dd), 2.27-2.31 (2H, m), 2.50-2.61 (2H, m), 3.44 (2H, s), 5.66-5.83 (1H, m), 6.50 (1H, s)

Production Example 51

0.99 g of the present compound (49) was dissolved in 60 ml of 1,4-dioxane, and 2.96 g of manganese dioxide was then added. The mixture was stirred and heated under reflux for 5 hours. The reaction mixture was cooled to room temperature and then filtered through Celite®. The filtrate was concentrated under reduced pressure, and the residue was subjected to silica gel column chromatography to obtain 0.67 g of a compound represented by the following formula:

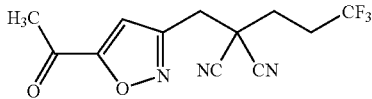

(hereinafter, referred to as the present compound (51)).
$^1$H-NMR (CDCl$_3$, TMS, δ (ppm)): 2.29-2.32 (2H, m), 2.54-2.63 (2H, m), 2.65 (3H, s), 3.50 (2H, s), 7.06 (1H, s)

Production Example 52

1.10 g of 3-(chloromethyl)-5-(1,1-difluoroethyl)isoxazole and 1.00 g of (3,3,3-trifluoropropyl)malononitrile were dissolved in 12 ml of N,N-dimethylformamide, and 0.84 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.98 g of a compound represented by the following formula:

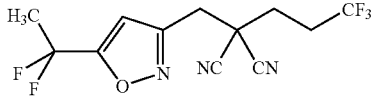

(hereinafter, referred to as the present compound (52)).
$^1$H-NMR (CDCl$_3$, TMS, δ (ppm)): 2.01 (3H, t), 2.22-2.33 (2H, m), 2.51-2.62 (2H, m), 3.44 (2H, s), 6.63 (1H, s)

Production Example 53

0.41 g of {[5-(1-methyl-1-hydroxyethyl)isoxazol-3-yl]methyl}malononitrile and 1.00 g of 1-iodo-3,3,3-trifluoropropane were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.46 g of a compound represented by the following formula:

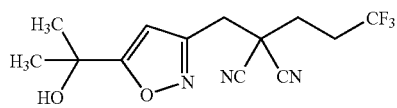

(hereinafter, referred to as the present compound (53)).
$^1$H-NMR (CDCl$_3$, TMS, δ (ppm)): 1.68 (6H, s), 2.27-2.31 (2H, m), 2.49-2.61 (2H, m), 3.41 (2H, s), 6.35 (1H, s)

Production Example 54

0.36 g of the present compound (53) was dissolved in 5 ml of dichloromethane, and 0.24 g of dimethylamino)sulfur trifluoride was added under ice-cooling. The mixture was stirred at room temperature for 4 hours. After aqueous saturated sodium hydrogen carbonate was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.27 g of a compound represented by the following formula:

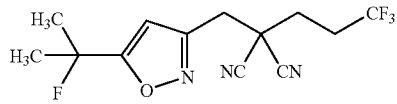

(hereinafter, referred to as the present compound (54)).
$^1$H-NMR (CDCl$_3$, TMS, δ (ppm)): 1.76 (6H, d), 2.28-2.32 (2H, m), 2.50-2.62 (2H, m), 3.43 (2H, s), 6.43 (1H, s)

Production Example 55

0.41 g of {[5-(1-methyl-1-hydroxyethyl)isoxazol-3-yl]methyl}malononitrile and 0.57 g of methyl iodide were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.31 g of a compound represented by the following formula:

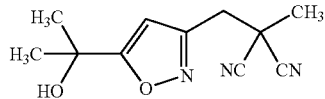

(hereinafter, referred to as the present compound (55)).
$^1$H-NMR (CDCl$_3$, TMS, δ (ppm)): 1.62 (6H, s), 1.87 (3H, s), 3.35 (2H, s), 6.35 (1H, s)

Production Example 56

0.41 g of {[5-(1-methyl-1-hydroxyethyl)isoxazol-3-yl]methyl}malononitrile and 0.66 g of ethyl iodide were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.32 g of a compound represented by the following formula:

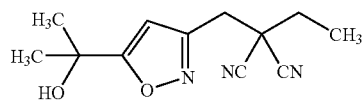

(hereinafter, referred to as the present compound (56)).

$^1$H-NMR (CDCl$_3$, TMS, δ (ppm)): 1.31 (3H, t), 1.65 (6H, s), 2.06 (2H, q), 3.34 (2H, s), 6.36 (1H, s)

Production Example 57

0.41 g of {[5-(1-methyl-1-hydroxyethyl)isoxazol-3-yl]methyl}malononitrile and 0.73 g of 1-iodopropane were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.30 g of a compound represented by the following formula:

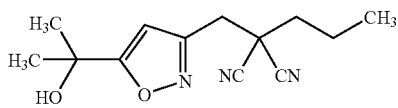

(hereinafter, referred to as the present compound (57)).

$^1$H-NMR (CDCl$_3$, TMS, δ (ppm)): 1.04 (3H, t), 1.63 (6H, s), 1.71-1.81 (2H, m), 1.94-1.19 (2H, m), 3.34 (2H, s), 6.36 (1H, s)

Production Example 58

0.41 g of {[5-(1-methyl-1-hydroxyethyl)isoxazol-3-yl]methyl}malononitrile and 0.81 g of 1-iodobutane were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.31 g of a compound represented by the following formula:

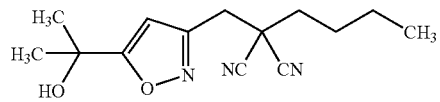

(hereinafter, referred to as the present compound (58)).

$^1$H-NMR (CDCl$_3$, TMS, δ (ppm)): $^1$H-NMR (CDCl$_3$, TMS, δ (ppm)): 0.94 (3H, t), 1.39-1.49 (2H, m), 1.63 (6H, s), 1.61-1.74 (2H, m), 1.89-1.99 (2H, m), 3.34 (2H, s), 6.36 (1H, s)

Production Example 59

0.41 g of {[5-(1-methyl-1-hydroxyethyl)isoxazol-3-yl]methyl}malononitrile and 0.88 g of 1-iodo-3-methylbutane were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.31 g of a compound represented by the following formula:

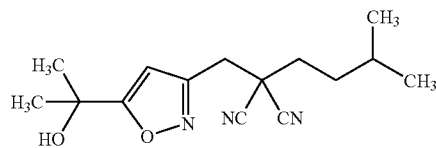

(hereinafter, referred to as the present compound (59)).

$^1$H-NMR (CDCl$_3$, TMS, δ (ppm)): 0.95 (6H, d), 1.53-1.69 (2H, m), 1.65 (6H, s), 1.90-1.94 (2H, m), 1.97-2.04 (2H, m), 3.34 (2H, s), 6.36 (1H, s)

Production Example 60

0.41 g of {[5-(1-methyl-1-hydroxyethyl)isoxazol-3-yl]methyl}malononitrile and 0.63 g of allyl chloride were dissolved in 6 ml of N,N-dimethylformamide, and 0.55 g of potassium carbonate was then added under ice-cooling. The mixture was stirred at room temperature overnight. After water was added, the reaction mixture was extracted with ethyl-t-butyl ether. The organic layer was washed with water, dried over anhydrous magnesium sulfate, filtered and then concentrated under reduced pressure. The residue was subjected to silica gel column chromatography to obtain 0.33 g of a compound represented by the following formula:

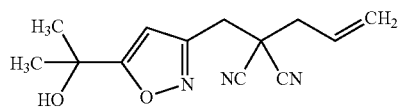

(hereinafter, referred to as the present compound (60)).

$^1$H-NMR (CDCl$_3$, TMS, δ (ppm)): 1.65 (6H, s), 2.68 (2H, d), 3.34 (2H, s), 5.39-5.51 (2H, m), 5.85-5.99 (1H, m), 6.36 (1H, s)

Production Example 61

0.41 g of {[5-(1-methyl-1-hydroxyethyl)isoxazol-3-yl]methyl}malononitrile and 0.63 g of 4-iodo-1-butene were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.43 g of (3-butenyl){[5-(1-methyl-1-hydroxyethyl)isoxazol-3-yl]methyl}malononitrile represented by the following formula:

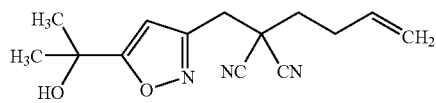

(hereinafter, referred to as the present compound (61)).

$^1$H-NMR (CDCl$_3$, TMS, δ (ppm)): 1.65 (6H, s), 2.02-2.18 (2H, m), 2.43-2.52 (2H, m), 3.36 (2H, s), 5.11-5.21 (2H, m), 5.78-5.85 (1H, m), 6.36 (1H, s)

Production Example 62

0.41 g of {1-[5-(1-methyl-1-hydroxyethyl)isoxazol-3-yl]ethyl}malononitrile and 1.00 g of 1-iodo-3,3,3-trifluoropropane were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain a compound represented by the following formula:

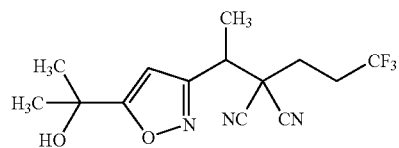

(hereinafter, referred to as the present compound (62)).

$^1$H-NMR (CDCl$_3$, TMS, δ (ppm)): 1.64 (3H, s), 1.66 (3H, s), 1.71 (3H, d), 2.08-2.20 (2H, m), 2.41-2.65 (2H, m), 3.41 (1H, q), 6.33 (1H, s)

Production Example 63

0.41 g of {1-[5-(1-methyl-1-hydroxyethyl)isoxazol-3-yl]ethyl}malononitrile and 0.82 g of allyl chloride were dissolved in 6 ml of N,N-dimethylformamide, and 0.55 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.44 g of a compound represented by the following formula:

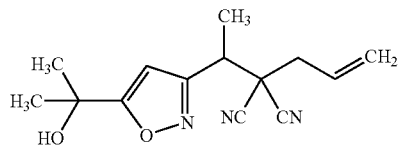

(hereinafter, referred to as the present compound (63)).

$^1$H-NMR (CDCl$_3$, TMS, δ (ppm)): 1.65 (6H, s), 1.67 (3H, d), 2.23 (1H, bs.), 2.55-2.57 (2H, m), 3.53 (1H, q), 5.39-5.46 (2H, m), 5.86-5.97 (1H, m), 6.34 (1H, s)

Production Example 64

0.40 g of {1-[5-(1-methyl-1-hydroxyethyl)isoxazol-3-yl]propyl}malononitrile and 0.43 g of 1-iodo-3,3,3-trifluoropropane were dissolved in 5 ml of N,N-dimethylformamide, and 0.25 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.37 g of a compound represented by the following formula:

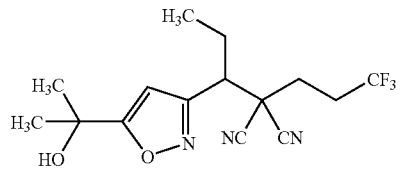

(hereinafter, referred to as the present compound (64)).

$^1$H-NMR (CDCl$_3$, TMS, δ (ppm)): 0.92 (3H, t), 1.66 (6H, s), 1.99-2.28 (4H, m), 2.42-2.60 (2H, m), 3.24-3.28 (1H, m), 6.32 (1H, s)

Production Example 65

0.40 g of {1-[5-(1-methyl-1-hydroxyethyl)isoxazol-3-yl]-2-methylpropyl}malononitrile and 0.40 g of 1-iodo-3,3,3-trifluoropropane were dissolved in 5 ml of N,N-dimethylformamide, and 0.25 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.33 g of a compound represented by the following formula:

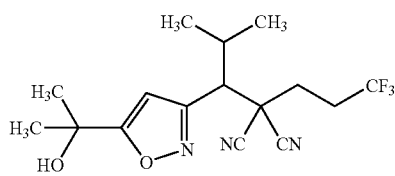

(hereinafter, referred to as the present compound (65)).

$^1$H-NMR (CDCl$_3$, TMS, δ (ppm)): 1.08 (3H, d), 1.18 (3H, d), 1.66 (6H, s), 1.93-2.11 (2H, m), 2.40-2.63 (3H, m), 3.21 (1H, d), 6.34 (1H, s)

Production Example 66

0.56 g of {1-[5-(1-methyl-1-hydroxyethyl)isoxazol-3-yl]-2-propenyl}malononitrile and 0.58 g of 1-iodo-3,3,3-trifluoropropane were dissolved in 5 ml of N,N-dimethylformamide, and 0.35 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.46 g of a compound represented by the following formula:

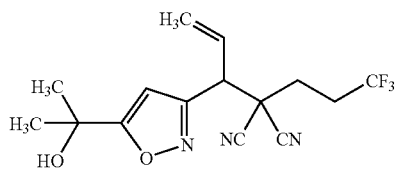

(hereinafter, referred to as the present compound (66)).

$^1$H-NMR (CDCl$_3$, TMS, δ (ppm)): 1.65 (6H, s), 2.14-2.32 (2H, m), 2.45-2.63 (2H, m), 3.98 (1H, d), 5.54-5.63 (2H, m), 6.07-6.15 (1H, m), 6.33 (1H, s)

Production Example 67

0.21 g of 3-(chloromethyl)-5-[1-methyl-1-(2-propynyloxy)ethyl]isoxazole and 0.16 g of (3,3,3-trifluoropropyl)malononitrile were dissolved in 2 ml of N,N-dimethylformamide, and 0.14 g of potassium carbonate and 0.17 g of potassium iodide were added under ice-cooling. The mixture was stirred at room temperature overnight.

After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.16 g of a compound represented by the following formula:

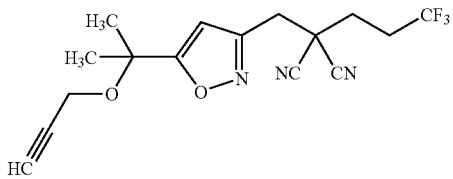

(hereinafter, referred to as the present compound (67)).

$^1$H-NMR (CDCl$_3$, TMS, δ (ppm)): 1.66 (6H, s), 2.28-2.31 (2H, m), 2.39 (1H, t), 2.50-2.61 (2H, m), 3.42 (2H, s), 4.05 (2H, d), 6.40 (1H, s)

Production Example 68

0.96 g of 5-(chloromethyl)-3-methoxyisoxazole and 1.05 g of (3,3,3-trifluoropropyl)malononitrile were dissolved in 13 ml of N,N-dimethylformamide, and 0.90 g of potassium carbonate was added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 1.05 g of a compound represented by the following formula:

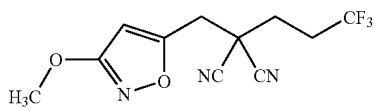

(hereinafter, referred to as the present compound (68)).

$^1$H-NMR (CDCl$_3$, TMS, δ (ppm)): 2.25-2.36 (2H, m), 2.48-2.60 (2H, m), 3.41 (2H, s), 3.96 (3H, s), 6.10 (1H, s)

Production Example 69

0.96 g of [(2-ethylthio-1-methylimidazol-5-yl)methyl]malononitrile and 0.91 g of 1-iodo-3,3,3-trifluoropropane were dissolved in 15 ml of N,N-dimethylformamide, and 0.60 g of potassium carbonate was then added under ice-cooling. The mixture was stirred at room temperature overnight. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 0.39 g of a compound represented by the flowing formula:

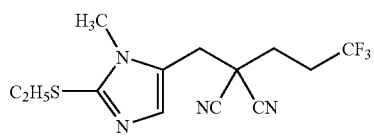

(hereinafter, referred to as the present compound (69)).

$^1$H-NMR (CDCl$_3$, TMS, δ (ppm)): 1.32 (3H, t), 2.25-2.30 (2H, m), 2.48-2.60 (2H, m), 3.10 (2H, q), 3.33 (2H, s), 3.62 (3H, s), 7.19 (1H, s)

Production Example 70

0.21 g of the present compound (69) was dissolved in 5 ml of chloroform, and 0.14 g of m-chloroperbenzoic acid was then added under ice-cooling. The mixture was stirred at room temperature overnight. After water was added, the reaction mixture was extracted with methyl-t-butyl ether. The organic layer was washed with water, dried over-anhydrous magnesium sulfate, filtered and then concentrated under reduced pressure. The residue was subjected to silica gel column chromatography to obtain 0.21 g of a compound represented by the following formula:

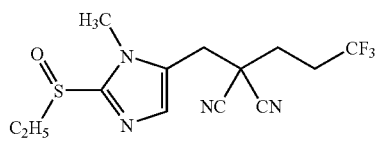

(hereinafter, referred to as the present compound (70)).

$^1$H-NMR (CDCl$_3$, TMS, δ (ppm)): 1.36-1.56 (3H, m), 2.30-2.35 (2H, m), 2.51-2.63 (2H, m), 3.37-3.57 (2H, m), 3.33 (2H, s), 4.00 (3H, s), 7.33 (1H, s)

Then, for production of an intermediate of the present compound, Reference Production Examples will be described.

Reference Production Example 1

3-t-Butyl-5-(chloromethyl)-1H-pyrazole hydrochloride

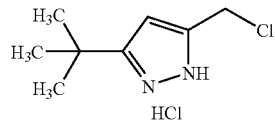

The above compound was prepared by a method described in J. Org. Chem., 67, 9200 (2002).

$^1$H-NMR (CDCl$_3$, TMS, δ (ppm)): 1.47 (9H, s), 4.78 (2H, s), 6.42 (1H, s)

Reference Production Example 2

3-t-Butyl-5-(chloromethyl)-1-methyl-1H-pyrazole Hydrochloride

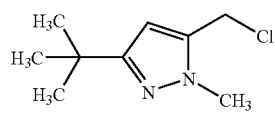

In a similar manner to Reference Production Example 1, the above compound was synthesized.

$^1$H-NMR (CDCl$_3$, TMS, δ (ppm)): 1.48 (9H, s), 4.33 (3H, s), 4.61 (2H, s), 6.37 (1H, s)

Reference Production Example 3

3-t-Butyl-5-(chloromethyl)-1-(2,2,2-trifluoromethyl)-1H-pyrazole hydrochloride

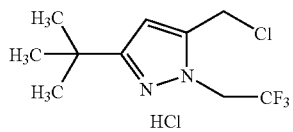

In a similar manner to Reference Production Example 1, the above compound was prepared.

$^1$H-NMR (CDCl$_3$, TMS, δ (ppm)): 1.38 (9H, s), 4.54 (2H, s), 4.74 (2H, q), 6.16 (1H, s)

Reference Production Example 4-1

(3-t-Butyl-isoxazol-5-yl)methanol

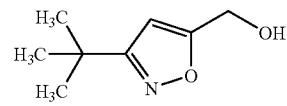

The above compound can be prepared from 2,2-dimethyl-6-(tetrahydro-2H-pyran-2-yloxy)-4-hexyn-3-one which is prepared by a method described in J. Org. Chem., 67, 9200 (2002), by the following method.

4.49 g of 2,2-dimethyl-6-(tetrahydro-2H-pyran-2-yloxy)-4-hexyn-3-one was dissolved in 20 ml of methanol, and 1.30 g of sodium methoxide and 1.53 g of hydroxylamine hydrochloride were added. The mixture was stirred at 70° C. for 2 hours. The reaction mixture was cooled to room temperature and then adjusted to pH 2 with concentrated hydrochloric acid. The mixture was stirred at room temperature for 18 hours. After aqueous saturated sodium hydrogen carbonate was added, the reaction mixture was extracted with ethyl acetate. The extract was washed with aqueous saturated sodium chloride, dried over anhydrous sodium sulfate and then concentrated under reduced pressure. The residue was subjected to silica gel column chromatography to obtain 1.12 g of (3-t-butyl-isoxazol-5-yl)methanol.

$^1$H-NMR (CDCl$_3$, TMS, δ (ppm)): 1.33 (9H, s), 4.74 (2H, s), 6.16 (1H, s)

Reference Production Example 4-2

3-t-Butyl-5-(chloromethyl)-isoxazole

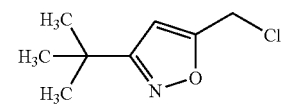

1.12 g of (3-t-butyl-isoxazol-5-yl)methanol was dissolved in 35 ml of dichloromethane, and 2.4 ml of thionyl chloride was added. The mixture was stirred at room temperature overnight. The reaction mixture was concentrated under reduced pressure. The residue was washed with hexane to obtain 1.12 g of 3-t-butyl-5-(chloromethyl)-isoxazole.

$^1$H-NMR (CDCl$_3$, TMS, δ (ppm)): 1.34 (9H, s), 4.58 (2H, s), 6.22 (1H, s)

Reference Production Example 5-1

(3-t-Butyl-isothiazol-5-yl)methanol

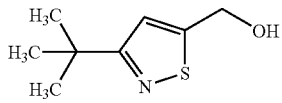

The above compound was prepared by a method described in Heterocycles, 27, 97, (1989).

$^1$H-NMR (CDCl$_3$, TMS, δ (ppm)): 1.34 (9H, s), 2.33 (1H, br. s), 4.72 (2H, s), 6.00 (1H, s)

Reference Production Example 5-2

3-t-Butyl-5-(chloromethyl)isothiazole

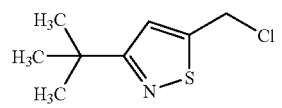

1.61 g of (3-t-butyl-isothiazol-5-yl)methanol was dissolved in 50 ml of dichloromethane, and 3.2 ml of thionyl chloride was added. The mixture was stirred at room temperature for 5 hours. The reaction mixture was concentrated under reduced pressure to obtain 1.12 g of 3-t-butyl-5-(chloromethyl)isothiazole. The crude product was subjected to the next step without purification.

$^1$H-NMR (CDCl$_3$, TMS, δ (ppm)): 1.36 (9H, s), 4.55 (2H, s), 6.05 (1H, s)

Reference Production Example 6-1

Ethyl 5-t-butyl-isoxazole-3-carboxylate

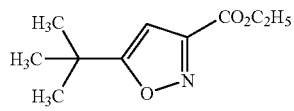

5.61 g of t-butylacetylene and 9.09 g of ethyl (2E)-chloro(hydroxyimino)acetate were dissolved in 70 ml of tetrahydrofuran, and 11.4 ml of triethylamine was then added dropwise at 0° C. over 30 minutes. The mixture was stirred at room temperature overnight. After aqueous saturated sodium chloride was added, the reaction mixture was separated into layers. The aqueous layer was extracted with methyl-t-butyl ether. The organic layers were combined, dried over anhydrous magnesium sulfate, filtered and then concentrated under reduced pressure. The residue was subjected to silica gel column chromatography to obtain 1.83 g of ethyl 5-t-butyl-isoxazole-3-carboxylate.

$^1$H-NMR (CDCl$_3$, TMS, δ (ppm)): 1.37 (9H, s), 1.39 (3H, t), 4.40 (2H, q), 6.37 (1H, s)

Reference Production Example 6-2

(5-t-Butyl-isoxazol-3-yl)methanol

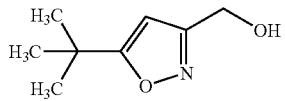

1.83 g of ethyl 5-t-butyl-isoxazole-5-carboxylate was dissolved in 18 ml of tetrahydrofuran, and 0.70 g of sodium borohydride in 10 ml of ethanol was then added. The mixture was stirred at room temperature for 10 hours. After 5 ml of water was added, the reaction mixture was concentrated to 5 ml under reduced pressure. The concentrated solution was extracted with methyl-t-butyl ether. The organic layer was dried over anhydrous sodium sulfate and then concentrated under reduced pressure to obtain 0.62 g of (5-t-butyl-isoxazol-3-yl)methanol.

$^1$H-NMR (CDCl$_3$, TMS, δ (ppm)): 1.35 (9H, s), 1.94 (1H, br. s), 4.72 (2H, d), 6.00 (1H, s)

Reference Production Example 6-3

5-t-Butyl-3-(chloromethyl)isoxazole

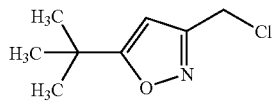

0.62 g of (5-t-butyl-isoxazol-3-yl)methanol was dissolved in 12 ml of dichloromethane, and 0.9 ml of thionyl chloride was added. The mixture was stirred at room temperature for 5 hours. The reaction mixture was concentrated under reduced pressure to obtain 0.69 g of 5-t-butyl-3-(chloromethyl)isoxazole.

$^1$H-NMR (CDCl$_3$, TMS, δ (ppm)): 1.34 (9H, s), 4.55 (2H, s), 6.05 (1H, s)

Reference Production Example 7-1

Methyl 1-t-butyl-1H-pyrazole-4-carboxylate

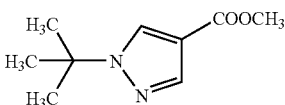

8.51 g of methyl 2-(dimethoxymethyl)-3-hydroxyacrylate sodium salt of was suspended in 80 ml of ethanol, and 8.09 g of t-butylhydrazine hydrochloride was then added. The mixture was stirred at 60° C. for 4 hours and then cooled to room temperature. After 50 ml of water was added, the reaction mixture was concentrated to 50 ml under reduced pressure.

The concentrated solution was extracted with ethyl acetate. The organic layer was washed with aqueous saturated sodium chloride, dried over anhydrous sodium sulfate and then concentrated under reduced pressure. The residue was recrystallized from hexane to obtain 5.26 g of methyl 1-t-butyl-pyrazole-4-carboxylate.

$^1$H-NMR (CDCl$_3$, TMS, δ (ppm)): 1.62 (9H, s), 3.83 (3H, s), 7.93 (1H, s), 8.02 (1H, s)

Reference Production Example 7-2

(1-t-Butyl-1H-pyrazol-4-yl)methanol

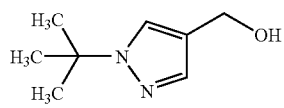

In a nitrogen atmosphere, 1.25 g of lithium aluminum hydride was suspended in 100 ml of tetrahydrofuran, and a solution of 5.01 g of methyl 1-t-butyl-1H-pyrazole-4-carboxylate in 50 ml of tetrahydrofuran was added dropwise at 0° C. over 30 minutes. Thereafter, the mixture was stirred at room temperature for 7 hours. The reaction mixture was cooled to 0° C. and 10 ml of a 1 mol/L aqueous potassium hydroxide solution was then added dropwise. Produced precipitates were filtered and washed with tetrahydrofuran. The filtrate was concentrated under reduced pressure. The residue was subjected to silica gel column chromatography to obtain 4.02 g of (1-t-butyl-1H-pyrazol-4-yl)methanol.

$^1$H-NMR (CDCl$_3$, TMS, δ (ppm)): 1.58 (9H, s), 4.59 (2H, d), 7.53 (1H, s), 7.54 (1H, s)

Reference Production Example 7-3

1-t-Butyl-4-(chloromethyl)-1H-pyrazole hydrochloride

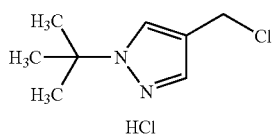

0.77 g of (1-t-butyl-1H-pyrazol-4-yl)methanol was dissolved in 25 ml of dichloromethane, and 1.7 ml of thionyl chloride was added. The mixture was stirred at room temperature for 5 hours. Thereafter, the reaction mixture was concentrated under reduced pressure to obtain 1.12 g of 1-t-butyl-4-(chloromethyl)-1H-pyrazole hydrochloride.

$^1$H-NMR (CDCl$_3$, TMS, δ (ppm)): 1.50 (9H, s), 4.69 (2H, s), 7.51 (1H, s), 7.94 (1H, s)

Reference Production Example 8-1

Methyl 1-benzyl-1H-pyrazole-4-carboxylate

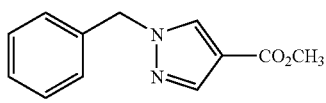

18.68 g of methyl 2-(dimethoxymethyl)-3-hydroxyacrylate sodium salt was added to 80 ml of ethanol, and 18.39 g of benzylhydrazine dihydrochloride was added. The mixture was stirred at 70° C. for 7 hours and then cooled to room temperature. After 100 ml of water was added, the mixture was concentrated to 100 ml under reduced pressure. The concentrated solution was extracted with ethyl acetate. The organic layer was washed with aqueous saturated sodium chloride, dried over anhydrous sodium sulfate and then concentrated under reduced pressure. The residue was subjected to silica gel column chromatography to obtain 7.39 g of methyl 1-benzyl-1H-pyrazole-4-carboxylate.

$^1$H-NMR (CDCl$_3$, TMS, δ (ppm)): 3.08 (3H, s), 5.30 (2H, s), 7.23-7.39 (5H, m), 7.85 (1H, s), 7.94 (1H, s)

Reference Production Example 8-2

(1-Benzyl-1H-pyrazol-4-yl)methanol

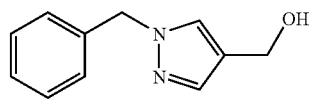

In a nitrogen atmosphere, 1.44 g of lithium aluminum hydride was added to 100 ml of tetrahydrofuran, and a solution of 7.39 g of methyl 1-benzyl-1H-pyrazole-4-carboxylate in 50 ml of tetrahydrofuran was added dropwise at 0° C. over 30 minutes. Thereafter, the mixture was stirred at room temperature for 5 hours. The reaction mixture was cooled to 0° C., and 15 ml of a 1 mol/L aqueous potassium hydroxide solution was added dropwise. Precipitates were filtered, washed with tetrahydrofuran and then concentrated under reduced pressure. The residue was subjected to silica gel column chromatography to obtain 6.32 g of (1-benzyl-1H-pyrazol-4-yl) methanol.

$^1$H-NMR (CDCl$_3$, TMS, δ (ppm)): 4.56 (2H, s), 5.27 (2H, s), 7.21-7.25 (2H, m), 7.28-7.37 (4H, m), 7.53 (1H, s)

Reference Production Example 8-3

1-Benzyl-4-(chloromethyl)-1H-pyrazole hydrochloride

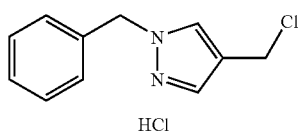

1.88 g of (1-benzyl-1H-pyrazol-4-yl)methanol was dissolved in 30 ml of dichloromethane, and 2.1 ml of thionyl chloride was added. The mixture was stirred at room temperature for 5 hours. The reaction mixture was concentrated under reduced pressure to obtain 2.39 g of 1-benzyl-4-(chloromethyl)-1H-pyrazole hydrochloride.

Reference Production Example 9

4-Chloromethyl-2-t-butyl-1,3-oxazole

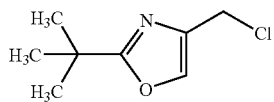

The above compound was prepared by a method described in International Patent Publication WO97/40009 pamphlet.
$^1$H-NMR (CDCl$_3$, TMS, δ (ppm)): 1.41 (9H, s), 4.50 (2H, s), 7.55 (1H, s)

Reference Production Example 10

4-(Chloromethyl)-2-methyl-1,3-thiazol

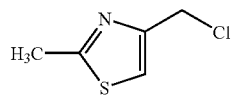

The above compound was prepared by a method described in German Patent Publication DE19848306.

Reference Production Example 11

4-(Chloromethyl)-2-t-butyl-1,3-oxazole

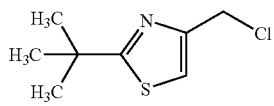

The above compound was prepared in a similar manner to a method described in German Patent Publication DE19848306.
$^1$H-NMR (CDCl$_3$, TMS, δ (ppm)): 1.44 (9H, s), 4.68 (2H, s), 7.16 (1H, s)

Reference Production Example 12-1

Ethyl 2-chloro-1,3-thiazole-4-carboxylate

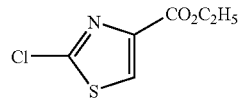

The above compound can be prepared from ethyl 2-amino-1,3-thiazole-4-carboxylate which is prepared by a method described in J. Heterocyclic. Chem., 26, 1643 (1989), by the following method.

15.0 g of ethyl 2-amino-1,3-thiazole-4-carboxylate was added to 400 ml of water, and 500 g of concentrated sulfuric acid, 29.2 g of copper sulfate and 23.0 g of sodium chloride were then added. The mixture was cooled to −10° C. Thereto a solution of 14.8 g of sodium nitrite in 55 ml of water was added dropwise while the internal temperature was kept at 0° C. or lower. After completion of the addition, the mixture was stirred at 0° C. for 30 minutes, heated to an internal temperature of room temperature, and then further stirred for 30 minutes. The reaction mixture was extracted with ethyl acetate. The organic layer was washed with 30% aqueous ammonia, dried over anhydrous sodium sulfate and then concentrated under reduced pressure. The resulting residue was subjected to silica gel column chromatography to obtain 9.0 g of ethyl 2-chloro-1,3-thiazole-4-carboxylate.
$^1$H-NMR (CDCl$_3$, TMS, δ (ppm)): 1.41 (3H, t), 4.42 (2H, q), 8.08 (1H, s)

Reference Production Example 12-2

Ethyl 2-(2-propynyloxy)-1,3-thiazole-4-carboxylate

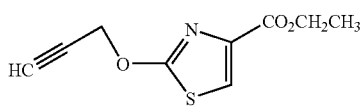

0.20 g of propargyl alcohol was dissolved in 20 ml of tetrahydrofuran, and 0.13 g of 60% sodium hydride was added at room temperature. The mixture was stirred at room temperature for 1 hour. After 0.50 g of ethyl 2-chloro-1,3-thiazole-4-carboxylate was added, the reaction mixture was stirred at room temperature for 3 hours. After aqueous saturated ammonium chloride was added, the reaction mixture was extracted with methyl-t-butyl ether. The organic layer was washed with aqueous saturated sodium chloride, dried over anhydrous sodium sulfate and then concentrated under reduced pressure. The residue was subjected to silica gel column chromatography to obtain 0.33 g of ethyl 2-(2-propynyloxy)-1,3-thiazole-4-carboxylate.
$^1$H-NMR (CDCl$_3$, TMS, δ (ppm)): 1.38 (3H, t), 2.61 (1H, s), 4.38 (2H, q), 5.14 (2H, s), 7.62 (1H, s)

Reference Production Example 12-3

[2-(2-Propynyloxy)-thiazol-4-yl]methanol

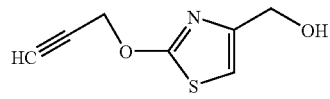

In a nitrogen atmosphere, 0.30 g of ethyl 2-(2-propynyloxy)-1,3-thiazole-4-carboxylate was dissolved in 10 ml of tetrahydrofuran, and 3.3 ml of a solution (1 mol/L) of diisobutylaluminum hydride in toluene was added dropwise at 0° C. The mixture was stirred at 0° C. for 1 hour. The reaction mixture was added to aqueous saturated sodium chloride and then extracted with ethyl acetate. The organic layer was dried over anhydrous sodium sulfate and then concentrated under reduced pressure to obtain 0.22 g of [2-(2-propynyloxy)-thiazol-4-yl]methanol.

¹H-NMR (CDCl₃, TMS, δ (ppm)): 2.06 (1H, br. s), 2.57 (1H, s), 4.57 (2H, d), 5.03 (2H, s), 6.59 (1H, s)

Reference Production Example 12-4

4-(Chloromethyl)-2-(2-propynyloxy)-thiazole

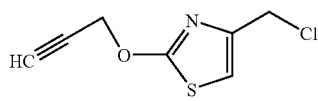

0.20 g of [2-(2-propynyloxy)-thiazol-4-yl]methanol was dissolved in 5 ml of chloroform, and 0.2 g of thionyl chloride was added. The mixture was heated to reflux for 1 hour. The reaction mixture was cooled to room temperature and then concentrated under reduced pressure to obtain 0.30 g of 4-(chloromethyl)-2-(2-propynyloxy)-thiazole.

Reference Production Example 13

5-(Chloromethyl)-2-methyl-1,3-thiadiazole hydrochloride

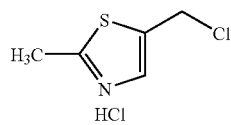

The above compound was prepared according to a method described in Japanese Patent Laid Open Publication No. 2001-58979.

¹H-NMR (CDCl₃, TMS, δ (ppm)): 3.15 (3H, s), 4.83 (2H, s), 8.05 (1H, s)

Reference Production Example 14

5-(Chloromethyl)-2-methyl-1,3-thiadiazole hydrochloride

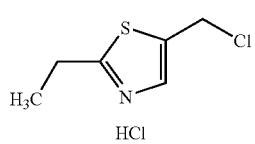

The above compound was prepared according to a method described in Japanese Patent Laid Open Publication No. 2001-58979.

¹H-NMR (CDCl₃, TMS, δ (ppm)): 1.54 (3H, t), 3.45 (2H, q), 4.81 (2H, s), 8.01 (1H, s)

Reference Production Example 15

5-(Chloromethyl)-2-t-butyl-1,3-thiadiazole hydrochloride

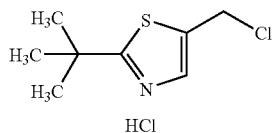

The above compound was prepared according to a method described in Japanese Patent Laid Open Publication No. 2001-58979.

¹H-NMR (CDCl₃, TMS, δ (ppm)): 1.64 (9H, s), 4.80 (2H, s), 6.61 (1H, br. s), 8.01 (1H, s)

Reference Production Example 16-1

2-Chloro-1,3-thiazole-5-carbaldehyde

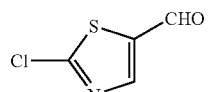

The above compound was prepared by a method described in J. Chem. Soc. Perkin Trans. 1, 329 (1990).

Reference Production Example 16-2

2-(2-Propynyloxy)-1,3-thiazole-5-carbaldehyde

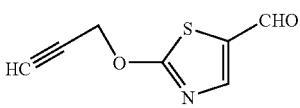

0.37 g of propargyl alcohol was dissolved in 100 ml of tetrahydrofuran, and 0.9 g of 60% sodium hydride was added in portions. The mixture was stirred at room temperature for 1 hour. Thereafter, 3.0 g of 2-chloro-1,3-thiazole-5-carbaldehyde was added to the reaction mixture and the mixture was stirred at room temperature for 3 hours. After aqueous saturated ammonium chloride was added, the reaction mixture was extracted with methyl-t-butyl ether. The organic layer was washed with aqueous saturated sodium chloride, dried over anhydrous sodium sulfate and then concentrated under reduced pressure. The residue was subjected to silica gel column chromatography to obtain 1.44 g of 2-(2-propynyloxy)-1,3-thiazole-5-carbaldehyde.

¹H-NMR (CDCl₃, TMS, δ (ppm)): 2.64 (1H, s), 5.13 (2H, s), 7.87 (1H, s), 9.84 (1H, s)

Reference Production Example 16-3

{[2-(2-Propynyloxy)-1,3-thiazol-5-yl]methyl}malononitrile

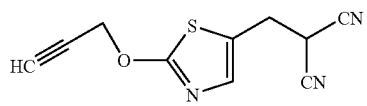

1.4 g of 2-(2-propynyloxy)-1,3-thiazole-5-carbaldehyde was dissolved in a mixture of 6 ml of water and 14 ml of ethanol, and 0.56 g of malononitrile was added dropwise. The mixture was stirred at room temperature for 3 hours. Thereafter, the reaction mixture was filtered, and the resulting cake was washed with 5 ml of ethanol two times and dried under reduced pressure to obtain 1.55 g of {[2-(2-propynyloxy)-1,3-thiazol-5-yl]methylidene}malononitrile.

Then, the resulting {[2-(2-propynyloxy)-1,3-thiazol-5-yl]methylidene}malononitrile was dissolved in 20 ml of ethanol, and a suspension of 0.09 g of sodium borohydride in 1 ml of ethanol was added dropwise. The mixture was stirred at room temperature for 1 hour. After 10 ml of 3% hydrochloric acid was added, the reaction mixture was extracted with ethyl acetate. The organic layer was washed with aqueous saturated sodium chloride, dried over anhydrous magnesium sulfate and then concentrated under reduced pressure to obtain 1.55 g of {[2-(2-propynyloxy)-1,3-thiazol-5-yl]methyl}.

$^1$H-NMR (CDCl$_3$, TMS, δ (ppm)): 2.61 (1H, s), 3.39 (2H, d), 3.94 (1H, t), 5.04 (2H, s), 7.13 (1H, s)

Reference Production Example 17-1

Methyl 3-t-butyl-1,2,4-thiadiazole-5-carboxylate

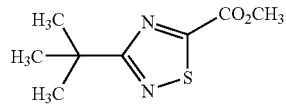

The above compound was prepared by a method described in International Patent Publication WO 01/055136 pamphlet.

$^1$H-NMR (CDCl$_3$, TMS, δ (ppm)): 1.51 (9H, s), 4.02 (3H, s)

Reference Production Example 17-2

(3-t-Butyl-1,2,4-thiadiazol-5-yl)methanol

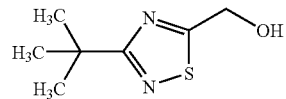

0.96 g of methyl 3-t-butyl-1,2,4-thiadiazole-5-carboxylate was dissolved in 48 ml of dichloromethane and then cooled to −78° C. under a nitrogen atmosphere. To the solution, 11 ml of a solution (1 mol/L) of diisobutylaluminum hydride in toluene was added and the mixture was stirred at 0° C. for 3 hours. After 10 ml of 1 mol/L hydrochloric acid was added, the reaction mixture was stirred for 10 minutes and 50 ml of aqueous saturated sodium hydrogen carbonate was then added. The reaction mixture was extracted with chloroform, dried over anhydrous sodium sulfate and then concentrated under reduced pressure. The residue was subjected to silica gel column chromatography to obtain 0.56 g of (3-t-butyl-1,2,4-thiadiazol-5-yl)methanol.

$^1$H-NMR (CDCl$_3$, TMS, δ (ppm)): 1.43 (9H, s), 5.09 (2H, s)

Reference Production Example 17-3

3-t-Butyl-5-(chloromethyl)-1,2,4-thiadiazole hydrochloride

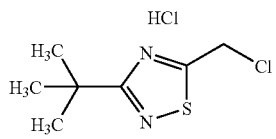

0.71 g of 3-t-butyl-5-hydroxymethyl-1,2,4-thiadiazole was dissolved in 20 ml of dichloromethane, and 1.4 ml of thionyl chloride was added. The mixture was stirred at room temperature for 4 hours. The reaction mixture was concentrated under reduced pressure to obtain 0.76 g of 3-t-butyl-5-(chloromethyl)-1,2,4-thiadiazole hydrochloride.

$^1$H-NMR (CDCl$_3$, TMS, δ (ppm)): 1.42 (9H, s), 4.91 (2H, s)

Reference Production Example 18-1

N'-(chloroacetyl)-2,2-dimethylpropanohydrazide

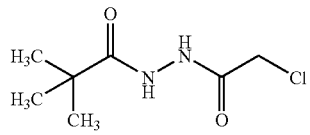

Under a nitrogen atmosphere, 2.86 g of 2,2-dimethylpropanohydrazide was dissolved in tetrahydrofuran, and 2.78 g of chloroacetyl chloride was then added at 0° C. The mixture was stirred at room temperature for 18 hours. After aqueous saturated sodium hydrogen carbonate was added, the reaction mixture was extracted with ethyl acetate. The organic layer was washed with aqueous saturated sodium chloride, dried over anhydrous sodium sulfate and then concentrated under reduced pressure to obtain 2.58 g of N'-(chloroacetyl)-2,2-dimethylpropanohydrazide.

$^1$H-NMR (CDCl$_3$, TMS, δ (ppm)): 1.27 (9H, s), 4.77 (2H, s), 8.58 (1H, br. s), 9.55 (1H, br. s)

Reference Production Example 18-2

2-t-Butyl-5-(chloromethyl)-1,3,4-oxadiazole

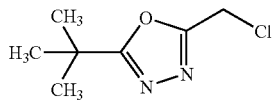

A mixture of 1.34 g of N'-(chloroacetyl)-2,2-dimethylpropanohydrazide and 6.6 g of polyphosphoric acid was stirred at 90° C. for 10 hours. The reaction mixture was cooled to room temperature. After 200 ml of water and then sodium bicarbonate were added, the reaction mixture was extracted with ethyl acetate. The organic layer was washed with water, dried over anhydrous sodium sulfate and then concentrated under reduced pressure to obtain 1.12 g of 2-t-butyl-5-(chloromethyl)-1,3,4-oxadiazole.

$^1$H-NMR (CDCl$_3$, TMS, δ (ppm)): 1.47 (9H, s), 4.68 (2H, s)

Reference Production Example 19-1

2-Chloro-N-hydroxyacetoamidine

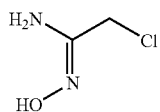

The above compound was prepared by a method described in U.S. patent specification U.S. Pat. No. 3,956,498.

$^1$H-NMR (CDCl$_3$, TMS, δ (ppm)): 4.05 (2H, s), 4.79 (2H, br. s)

Reference Production Example 19-2

3-(Chloromethyl)-5-t-butyl-1,2,4-oxadiazole

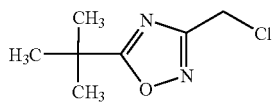

5.0 g of 2-chloro-N-hydroxyacetoamidine and 6.11 g of trimethylacetyl chloride were dissolved in 100 ml of N,N-dimethylformamide, and 5.6 g of triethylamine was then added dropwise under ice-cooling. After completion of the addition, the reaction mixture was stirred at 130° C. for 6 hours and then cooled to room temperature. After aqueous saturated sodium chloride, the reaction mixture was extracted with methyl-t-butyl ether. The organic layer was washed with aqueous saturated sodium chloride, dried over anhydrous sodium sulfate and then concentrated under reduced pressure. The residue was subjected to silica gel column chromatography to obtain 7.0 g of 3-(chloromethyl)-5-t-butyl-1,2,4-oxadiazole.

$^1$H-NMR (CDCl$_3$, TMS, δ (ppm)): 1.45 (9H, s), 4.56 (2H, s)

Reference Production Example 20

3-(Chloromethyl)-5-(1-methylcyclopropyl)-1,2,4-oxadiazole

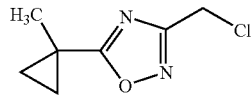

2.75 g of 2-chloro-N-hydroxyacetoamidine and 3.0 g of 1-methylcyclopropanecarbonyl chloride were dissolved in 50 ml of N,N-dimethylformamide, and 2.8 g of triethylamine was added dropwise under ice-cooling. After completion of the addition, the mixture was heated to 130° C., stirred for 6 hours and then cooled to room temperature. After aqueous saturated sodium chloride was added, the reaction mixture was extracted with methyl-t-butyl ether. The organic layer was washed with aqueous saturated sodium chloride, dried over anhydrous sodium sulfate and then concentrated under reduced pressure. The residue was subjected to silica gel column chromatography to obtain 0.97 g of 3-(chloromethyl)-5-(1-methylcyclopropyl)-1,2,4-oxadiazole.

$^1$H-NMR (CDCl$_3$, TMS, δ (ppm)): 1.01-1.06 (2H, m), 1.43-1.47 (2H, m), 1.58 (3H, s), 4.54 (2H, s)

Reference Production Example 21

3-(Chloromethyl)-5-ethyl-1,2,4-oxadiazole 2.0 g of 2-chloro-N-hydroxyacetoamidine and 1.80 g of propionyl chloride were dissolved in 50 ml of N,N-dimethylformamide, and 2.05 g of triethylamine was added dropwise under ice-cooling. The mixture was stirred at 130° C. for 5 hours and then cooled to room temperature. After aqueous saturated sodium chloride was added, the reaction mixture was extracted with methyl-t-butyl ether. The organic layer was washed with aqueous saturated sodium chloride, dried over anhydrous sodium sulfate and then concentrated under reduced pressure. The residue was subjected to silica gel column chromatography to obtain 0.62 g of 3-(chloromethyl)-5-ethyl-1,2,4-oxadiazole.

$^1$H-NMR (CDCl$_3$, TMS, δ (ppm)): 1.42 (3H, t), 2.92 (2H, q), 4.59 (2H, s)

Reference Production Example 22

3-(Chloromethyl)-5-(2,2-dimethylpropyl)-1,2,4-oxadiazole

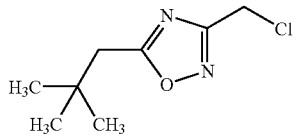

2.0 g of 2-chloro-N-hydroxyacetoamidine and 2.6 g of 3,3-dimethylbutyryl chloride were dissolved in 30 ml of N,N-dimethylformamide, and 2.05 g of triethylamine was added dropwise under ice-cooling. After completion of the addition, the mixture was stirred at 130° C. for 5 hours and then cooled to room temperature. After aqueous saturated sodium chloride was added, the reaction mixture was extracted with methyl-t-butyl ether. The organic layer was washed with aqueous saturated sodium chloride, dried over anhydrous sodium sulfate and then concentrated under reduced pressure. The residue was subjected to silica gel column chromatography to obtain 0.28 g of 3-(chloromethyl)-5-(2,2-dimethylpropyl)-1,2,4-oxadiazole.

$^1$H-NMR (CDCl$_3$, TMS, δ (ppm)): 1.05 (9H, s), 2.82 (2H, s), 4.60 (2H, s)

Reference Production Example 23

2-(Chloromethyl)-8-methylimidazo[1,2-a]pyridine

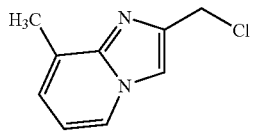

3.81 g of 1,3-dichloroacetone and 3.24 g of 2-amino-3-methylpyridine were dissolved in 30 ml of ethanol, and the solution was heated to reflux for 5 hours. The reaction mixture was cooled to room temperature and then concentrated under reduced pressure. To the residue, 50 ml of aqueous saturated sodium hydrogen carbonate was added and the mixture was extracted with ethyl acetate. The organic layer was dried over anhydrous sodium sulfate and then concentrated under reduced pressure. The residue was subjected to silica gel column chromatography and then recrystallized from hexane-methyl-t-butyl ether to obtain 1.52 g of 2-(chloromethyl)-8-methylimidazo[1,2-a]pyridine.

$^1$H-NMR (CDCl$_3$, TMS, δ(ppm)): 2.60 (3H, s), 4.80 (2H, s), 6.68 (1H, t), 6.96 (1H, dd), 7.61 (1H, s), 7.93 (1H, d)

Reference Production Example 24

2-(Chloromethyl)-5-methylimidazo[1,2-a]pyridine

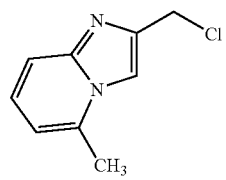

3.81 g of 1,3-dichloroacetone and 3.24 g of 2-amino-6-methylpyridine were dissolved in 30 ml of ethanol, and the solution was heated to reflux for 5 hours. The reaction mixture was cooled to room temperature and then concentrated under reduced pressure. After 50 ml of aqueous saturated sodium hydrogen carbonate was added, the residue was extracted with ethyl acetate. The organic layer was dried over anhydrous sodium sulfate and then concentrated under reduced pressure. The residue was subjected to silica gel column chromatography and then recrystallized from hexane-ethyl acetate to obtain 1.67 g of 2-(chloromethyl)-5-methylamindazo[1,2-a]pyridine.

$^1$H-NMR (CDCl$_3$, TMS, δ (ppm)): 2.58 (3H, s), 4.80 (2H, s), 6.62 (1H, dd), 7.15 (1H, dd), 7.47 (1H, d), 7.52 (1H, s)

Reference Production Example 25-1

Methyl 1-cyclohexyl-1H-pyrazole-4-carboxylate

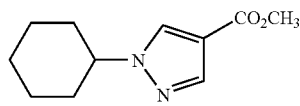

3.96 g of methyl 2-(dimethoxymethyl)-3-hydroxyacrylate sodium salt was suspended in 40 ml of ethanol, and 3.13 g of cyclohexylhydrazine hydrochloride was added. The mixture was stirred at 60° C. for 4 hours and then cooled to room temperature. After 50 ml of water was added, the reaction mixture was concentrated to 50 ml under reduced pressure. The concentrated solution was extracted with ethyl acetate. The organic layer was washed with aqueous saturated sodium chloride, dried over anhydrous sodium sulfate and then concentrated under reduced pressure. The residue was subjected to silica gel column chromatography to obtain 3.01 g of methyl 1-cyclohexyl-1H-pyrazole-4-carboxylate.

$^1$H-NMR (CDCl$_3$, TMS, δ (ppm)): 1.21-1.31 (1H, m), 1.37-1.48 (2H, m), 1.61-1.77 (4H, m), 1.89-1.92 (2H, s), 2.15-2.19 (2H, m), 3.82 (3H, s), 7.89 (1H, s), 7.91 (1H, s)

Reference Production Example 25-2

(1-Cyclohexyl-1H-pyrazol-4-yl)methanol

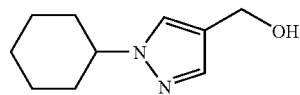

Under a nitrogen atmosphere, 0.57 g of lithium aluminum hydride was suspended in 100 ml of dry tetrahydrofuran, and a solution of 3.01 g of methyl 1-cyclohexyl-1H-pyrazole-4-carboxylate in 40 ml of tetrahydrofuran was added dropwise thereto over 15 minutes with stirring at 0° C. After completion of the addition, the mixture was stirred at room temperature for 7 hours and then cooled to 0° C. Thereto 10 ml of a 1 mol/L aqueous saturated sodium hydroxide solution was added dropwise. Produced precipitates were filtered and then washed with tetrahydrofuran. The filtrate was concentrated under reduced pressure. The residue was subjected to silica gel column chromatography to obtain 1.68 g of (cyclohexyl-1H-pyrazol-4-yl)methanol.

¹H-NMR (CDCl₃, TMS, δ (ppm)): 1.19-1.30 (1H, m), 1.36-1.75 (5H, m), 1.87-1.91 (2H, m), 2.13-2.16 (2H, m), 4.04-4.15 (1H, m), 4.58 (2H, s), 7.44 (1H, s), 7.49 (1H, s)

Reference Production Example 25-3

4-(Chloromethyl)-1-cyclohexyl-1H-pyrazole hydrochloride

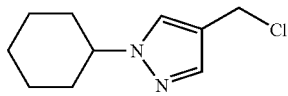

1.68 g of (1-cyclohexyl-1H-pyrazol-4-yl)methanol was dissolved in 20 ml of dichloromethane, and 2.0 ml of thionyl chloride was then added. The mixture was stirred at room temperature for 5 hours. The reaction mixture was concentrated under reduced pressure to obtain 2.15 g of 1-cyclohexyl-4-(chloromethyl)-1H-pyrazole hydrochloride.

¹H-NMR (CDCl₃, TMS, δ (ppm)): 1.24-1.36 (1H, m), 1.43-1.58 (2H, m), 1.73-1.83 (3H, m), 1.94-1.97 (2H, m), 2.33-2.37 (2H, m), 4.54 (2H, s), 4.71-4.79 (1H, m), 7.74 (1H, s), 7.91 (1H, s)

Reference Production Example 26

[(1-Propargyl-1H-pyrazol-4-yl)methyl]malononitrile

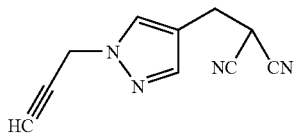

0.73 g of [(1-propargyl-1H-pyrazol-4-yl)methylidene]malononitrile was dissolved in 10 ml of tetrahydrofuran, and 0.19 g of sodium borohydride was then added under ice-cooling. The mixture was stirred for 4 hours under ice-cooling. The reaction mixture was added to 0.5 N hydrochloric acid and then extracted with ethyl acetate. The organic layer was dried over anhydrous magnesium sulfate, filtered and then concentrated under reduced pressure. The residue was subjected to silica gel column chromatography to obtain 0.32 g of [(1-prop-2-ynyl-1H-pyrazol-4-yl)methyl]malononitrile.

¹H-NMR (CDCl₃, TMS, δ (ppm)): 2.54 (1H, t), 3.21 (2H, d), 3.84 (1H, t), 4.95 (2H, d), 7.55 (1H, s), 7.72 (1H, s)

Reference Production Example 27

[(1-t-Butyl-1H-pyrazol-4-yl)methyl]malononitrile

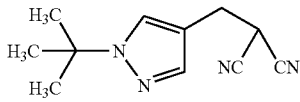

5.95 g of malononitrile was dissolved in 30 ml of N,N-dimethylformamide, and 12.44 g of potassium carbonate was then added under ice-cooling. Thereto a solution of 6.27 g of 1-t-butyl-4-(chloromethyl)-1H-pyrazole hydrochloride in 30 ml of N,N-dimethylformamide was added dropwise over 1 hour. After completion of the addition, the mixture was stirred at room temperature for 8 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography to obtain 4.12 g of [(1-t-butyl-1H-pyrazol-4-yl)methyl]malononitrile.

¹H-NMR (CDCl₃, TMS, δ (ppm)): 1.59 (9H, s), 3.20 (2H, d), 3.81 (1H, t), 7.53 (1H, s), 7.58 (1H, s)

Reference Production Example 28-1

Ethyl 5-(1H-pyrrol-1-yl)-1-t-butyl-1H-pyrazole-4-carboxylate

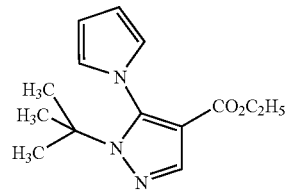

8.45 g of ethyl 5-amino-1-t-butyl-1H-pyrazole-4-carboxylate was dissolved in 60 ml of acetic acid, and 7.93 g of 2,5-dimethoxytetrahydrofuran was then added. The mixture was heated to reflux for 2 hours. The reaction mixture was concentrated under reduced pressure. After water was added, the residue was extracted with ethyl acetate. The organic layer was washed with water, dried over anhydrous magnesium sulfate, filtered and then concentrated under reduced pressure. The residue was subjected to silica gel column chromatography to obtain 8.95 g of ethyl 5-(1H-pyrrol-1-yl)-1-t-butyl-1H-pyrazole-4-carboxylate.

¹H-NMR (CDCl₃, TMS, δ (ppm)): 1.11 (3H, t), 1.46 (9H, s), 4.08 (2H, q), 6.33 (2H, t), 6.70 (2H, t), 77.93 (1H, s)

Reference Production Example 28-2

[5-(1H-pyrrol-1-yl)-1-t-butyl-1H-pyrazol-4-yl]methanol

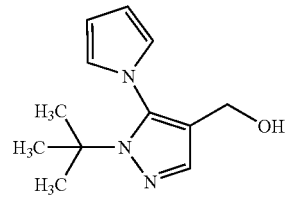

1.30 g of lithium aluminum hydride was suspended in 50 ml of tetrahydrofuran and thereto, under a nitrogen atmosphere, a solution of 8.95 g of ethyl 5-(1H-pyrrol-1-yl)-1-t-butyl-1H-pyrazole-4-carboxylate in 20 ml of tetrahydrofuran was added dropwise over 15 minutes under ice-cooling. The mixture was stirred for 8 hours under ice-cooling. After water was added, the reaction mixture was extracted with ethyl acetate. The organic layer was dried over anhydrous magnesium sulfate, filtered and then concentrated under reduced pressure. The residue was subjected to silica gel column chromatography to obtain 7.06 g of [5-(1H-pyrrol-1-yl)-1-t-butyl-1H-pyrazol-4-yl]methanol.

$^1$H-NMR (CDCl$_3$, TMS, δ (ppm)): 1.42 (9H, s), 4.24 (2H, s), 6.32 (2H, t), 6.73 (2H, t), 7.56 (1H, s)

Reference Production Example 28-3

4-(Chloromethyl)-5-(1H-pyrrol-1-yl)-1-t-butyl-1H-pyrazole

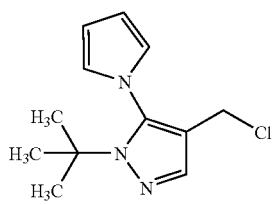

2.20 g of [5-(1H-pyrrol-1-yl)-1-t-butyl-1H-pyrazol-4-yl]methanol was dissolved in 20 ml of dichloromethane, and 0.73 ml of thionyl chloride was added. The mixture was stirred at room temperature for 1.5 hours and then concentrated under reduced pressure. After aqueous saturated sodium hydrogen carbonate was added, the residue was extracted with ethyl acetate. The organic layer was dried over anhydrous magnesium sulfate, filtered and then concentrated under reduced pressure. The residue was subjected to silica gel column chromatography to obtain 2.35 g of 4-(chloromethyl)-5-(1H-pyrrol-1-yl)-1-t-butyl-1H-pyrazole.

$^1$H-NMR (CDCl$_3$, TMS, δ (ppm)): 1.42 (9H, s), 4.18 (2H, s), 6.34 (2H, t), 6.73 (2H, t), 7.59 (1H, s)

Reference Production Example 29-1

(5-Trifluoromethyl-isoxazol-3-yl)methanol

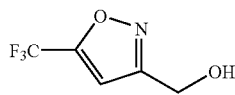

2.72 g of 4,4,5,5,5-pentafluoro-2-iodo-2-pentene-1-ol was dissolved in 7 ml of ethanol, and 3 ml of water, 0.69 g of hydroxylamine hydrochloride and 1.38 g of potassium carbonate were then added. The mixture was stirred and heated under reflux for 10 hours. The reaction mixture was concentrated under reduced pressure. After water was added, the residue was extracted with ethyl acetate. The organic layer was washed with water, dried over anhydrous magnesium sulfate, filtered and then concentrated under reduced pressure. The residue was subjected to silica gel column chromatography to obtain 0.57 g of (5-trifluoromethyl-isoxazol-3-yl)methanol.

$^1$H-NMR (CDCl$_3$, TMS, δ (ppm)): 4.84 (2H, s), 6.79 (1H, s)

Reference Example 29-2

3-(Bromomethyl)-5-trifluoromethylisoxazole

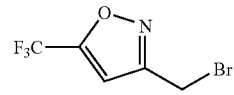

2.47 g of (5-trifluoromethyl-isoxazol-3-yl)methanol was dissolved in 80 ml of diethyl ether, and 6.56 g of triphenylphosphine and 8.9 g of carbon tetrabromide were then added. The mixture was stirred at room temperature for 1 hour. The reaction mixture was subjected to silica gel column chromatography to obtain 1.14 g of 3-(bromomethyl)-5-trifluoromethylisoxazole.

$^1$H-NMR (CDCl$_3$, TMS, δ (ppm)): 4.46 (2H, s), 6.87 (1H, s)

Reference Production Example 30-1

1-(5-Trifluoromethyl-isoxazol-3-yl)ethanol

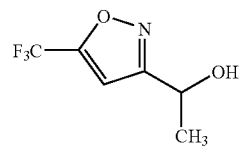

7.49 g of 5,5,6,6,6-pentafluoro-3-iodo-3-hexene-2-ol was dissolved in 70 ml of ethanol, and 30 ml of water, 3.34 g of hydroxylamine hydrochloride and 17.94 g of potassium carbonate were then added. The mixture was stirred and heated under reflux for 48 hours. The reaction mixture was concentrated under reduced pressure. After water was added, the residue was extracted with ethyl acetate. The organic layer was washed with water, dried over anhydrous magnesium sulfate, filtered and then concentrated under reduced pressure. The residue was subjected to silica gel column chromatography to obtain 1.53 g of 1-(5-trifluoromethyl-isoxazol-3-yl)ethanol.

$^1$H-NMR (CDCl$_3$, TMS, δ (ppm)): 1.59 (3H, d), 5.07 (1H, q), 6.77 (1H, s)

Reference Production Example 30-2

3-(1-Bromoethyl)-5-trifluoromethylisoxazole

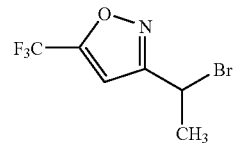

1-(5-Trifluoromethyl-isoxazol-3-yl)ethanol was dissolved in 35 ml of diethyl ether, and 2.93 g of triphenylphosphine and 3.71 g of carbon tetrabromide were then added. The mixture was stirred at room temperature for 1 hour. The reaction mixture was subjected to silica gel column chromatography to obtain 1.14 g of 3-(1-bromoethyl)-5-trifluoromethylisoxazole.

$^1$H-NMR (CDCl$_3$, TMS, δ (ppm)): 2.06 (3H, d), 5.17 (1H, q), 6.83 (1H, s)

Reference Production Example 31-1

9.01 g of 6,6,7,7,7-pentafluoro-4-iodo-4-heptene-3-ol was dissolved in 70 ml of ethanol, and 30 ml of water, 3.81 g of hydroxylamine hydrochloride and 7.51 g of potassium carbonate were then added. The mixture was stirred and heated under reflux for 24 hours. The reaction mixture was concentrated under reduced pressure. After water was added, the residue was extracted with ethyl acetate. The organic layer was washed with water, dried over anhydrous magnesium sulfate, filtered and then concentrated under reduced pressure. The residue was subjected to silica gel column chromatography to obtain 1.63 g of 1-(5-trifluoromethyl-isoxazol-3-yl)propanol.

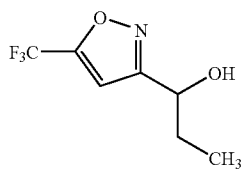

$^1$H-NMR (CDCl$_3$, TMS, δ (ppm)): 0.99 (3H, t), 1.84 (2H, m), 4.83 (1H, m), 6.75 (1H, s)

Reference Production Example 31-2

3-(1-Bromopropyl)-5-trifluoromethylisoxazole

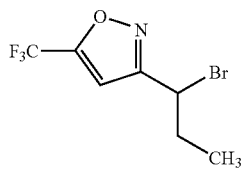

1.63 g of 1-(5-trifluoromethyl-isoxazol-3-yl)propanol was dissolved in 45 ml of diethyl ether, and 4.20 g of triphenylphosphine and 5.31 g of carbon tetrabromide were then added. The mixture was stirred at room temperature for 1 hour. The reaction mixture was subjected to silica gel column chromatography to obtain 1.00 g of 3-(1-bromopropyl)-5-trifluoromethylisoxazole.

$^1$H-NMR (CDCl$_3$, TMS, δ (ppm)): 1.24 (3H, t), 2.18-2.29 (2H, m), 4.94 (1H, t), 6.80 (1H, s)

Reference Production Example 32-1

8.9 g of 4,4,5,5,6,6,6-heptafluoro-2-iodo-2-hexene-1-ol was dissolved in 90 ml of ethanol, and 40 ml of water, 4.17 g of hydroxylamine hydrochloride and 20.70 g of potassium carbonate were then added. The mixture was stirred and heated under reflux for 20 hours. The reaction mixture was concentrated under reduced pressure. After water was added, the residue was extracted with ethyl acetate. The organic layer was washed with water, dried over anhydrous magnesium sulfate, filtered and then concentrated under reduced pressure. The residue was subjected to silica gel column chromatography to obtain 2.78 g of (5-pentafluoroethyl-isoxazol-3-yl)methanol.

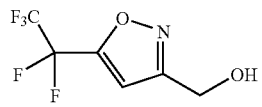

$^1$H-NMR (CDCl$_3$, TMS, δ (ppm)): 4.88 (2H, s), 6.85 (1H, s)

Reference Production Example 32-2

3-(Bromomethyl)-5-pentafluoroethylisoxazole

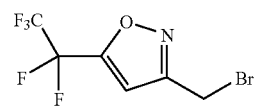

2.78 g of (5-pentafluoroethyl-isoxazol-3-yl)methanol was dissolved in 10 ml of diethyl ether, and 5.25 g of triphenylphosphine and 6.63 g of carbon tetrabromide were then added. The mixture was stirred at room temperature for 1 hour. The reaction mixture was subjected to silica gel column chromatography to obtain 1.83 g of 3-(bromomethyl)-5-pentafluoroethylisoxazole.

$^1$H-NMR (CDCl$_3$, TMS, δ (ppm)): 4.46 (2H, s), 6.87 (1H, s)

Reference Production Example 33-1

14.94 g of 4,4,5,5,6,6,7,7,7-nonafluoro-2-iodo-2-heptene-1-ol was dissolved in 150 ml of ethanol, and 70 ml of water, 5.17 g of hydroxylamine hydrochloride and 25.67 g of potassium carbonate were then added. The mixture was stirred and heated under reflux for 24 hours. The reaction mixture was concentrated under reduced pressure. After water was added, the residue was extracted with ethyl acetate. The organic layer was washed with water, dried over anhydrous magnesium sulfate, filtered and then concentrated under reduced pressure. The residue was subjected to silica gel column chromatography to obtain 3.53 g of (5-heptafluoropropyl-isoxazol-3-yl)methanol.

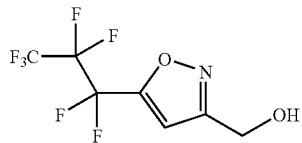

$^1$H-NMR (CDCl$_3$, TMS, δ (ppm)): 4.86 (2H, s), 6.85 (1H, s)

Reference Production Example 33-2

3-(Chloromethyl)-5-heptafluoropropylisoxazol

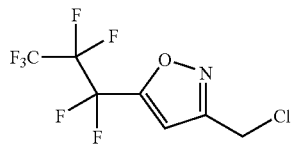

2.78 g of (5-heptafluoropropyl-isoxazol-3-yl)methanol was dissolved in 10 ml of diethyl ether, and 5.25 g of triphenylphosphine and 6.63 g of carbon tetrabromide were then added. The mixture was stirred at room temperature for 1 hour. The reaction mixture was subjected to silica gel column chromatography to obtain 1.83 g of 3-(chloromethyl)-5-(heptafluoropropyl)isoxazole.

$^1$H-NMR (CDCl$_3$, TMS, δ (ppm)): 4.66 (2H, s), 6.89 (1H, s)

Reference Production Example 34-1

(5-i-Propyl-isoxazol-3-yl)methanol

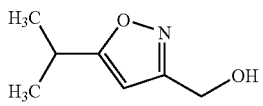

20.76 g of ethyl 5-i-propyl-isoxazole-3-carboxylate was dissolved in 200 ml of ethanol, and 4.20 g of sodium borohydride was then added. The mixture was stirred at room temperature for 10 hours. After 50 ml of water was added, the reaction mixture was concentrated to 50 ml under reduced pressure. The concentrated solution was extracted with ethyl acetate. The organic layer was dried over anhydrous magnesium sulfate, filtered and then concentrated under reduced pressure. The residue was subjected to silica gel column chromatography to obtain 15.13 g of (5-i-propyl-isoxazol-3-yl)methanol.

$^1$H-NMR (CDCl$_3$, TMS, δ (ppm)): 1.28 (6H, d), 3.04 (1H, m), 4.72 (2H, s), 6.01 (1H, s)

Reference Production Example 34-2

(5-i-Propyl-isoxazol-3-yl)methyl 4-toluenesulfonate

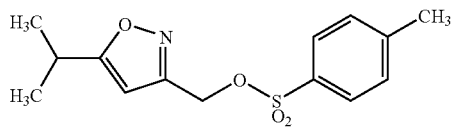

4.24 g of (5-i-propyl-isoxazol-3-yl)methanol was dissolved in 10 ml of pyridine, and 6.67 g of 4-toluenesulfonyl chloride was then added under ice-cooling. The mixture was stirred for 5 hours under ice-cooling. After water was added, the reaction mixture was extracted with ethyl acetate. The organic layer was washed with water, dried over anhydrous magnesium sulfate, filtered and then concentrated under reduced pressure. The residue was subjected to silica gel column chromatography to obtain 1.82 g of (5-i-propyl-isoxazol-3-yl)methyl 4-toluenesulfonate.

$^1$H-NMR (CDCl$_3$, TMS, δ (ppm)): 1.22 (3H, d), 1.60 (3H, d), 2.35 (3H, s), 2.93-3.01 (1H, m), 5.63 (2H, s), 6.54 (1H, s), 7.30 (2H, d), 7.74 (2H, d)

Reference Production Example 35-1

5-i-Propyl-isoxazole-3-carbaldehyde

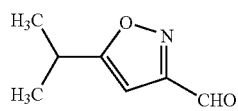

7.59 g of (5-i-propyl-isoxazol-3-yl)methanol was dissolved in 100 ml of 1,4-dioxane, and 21.74 g of manganese dioxide was then added. The mixture was stirred and heated under reflux for 10 hours. The reaction mixture was cooled to room temperature and then filtered through Celite®. The filtrate was concentrated under reduced pressure to obtain 6.72 g of 5-i-propyl-isoxazole-3-carbaldehyde.

Reference Production Example 35-2

1-(5-i-Propyl-isoxazol-3-yl)ethanol

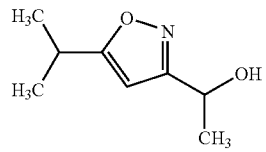

5.70 g of 5-i-propylisoxazole-3-carbaldehyde was dissolved in 82 ml of 1,4-dioxane, and 48 ml of a 0.93 M solution of methylmagnesium bromide in tetrahydrofuran was then added under ice-cooling. The mixture was stirred for 1 hour under ice-cooling. After water was added, the reaction mixture was extracted with ethyl acetate. The organic layer was washed with water, dried over anhydrous magnesium sulfate, filtered and then concentrated under reduced pressure. The residue was subjected to silica gel column chromatography to obtain 5.66 g of 1-(5-i-propyl-isoxazol-3-yl)ethanol.

$^1$H-NMR (CDCl$_3$, TMS, δ (ppm)): 1.29 (6H, d), 1.53 (3H, d), 3.02 (1H, m), 4.97 (1H, m), 5.98 (1H, s)

Reference Production Example 35-3

3-(1-Chloroethyl)-5-i-propylisoxazole

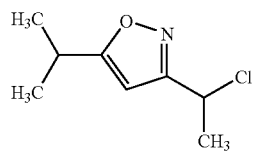

5.66 g of 1-(5-i-propyl-isoxazol-3-yl)ethanol was dissolved in 30 ml of pyridine, and 7.20 g of 4-toluenesulfonyl chloride was then added under ice-cooling. The mixture was stirred for 5 hours under ice-cooling. After water was added, the reaction mixture was extracted with ethyl acetate. The organic layer was washed with water, dried over anhydrous magnesium sulfate, filtered and then concentrated under reduced pressure. The residue was subjected to silica gel column chromatography to obtain 3.63 g of 3-(1-chloroethyl)-5-i-propylisoxazole.

$^1$H-NMR (CDCl$_3$, TMS, δ (ppm)): 1.31 (6H, d), 1.86 (3H, d), 3.04-3.10 (1H, m), 5.10 (1H, q), 6.06 (1H, s)

Reference Production Example 36-1

5-t-Butyl-isoxazole-3-carbaldehyde

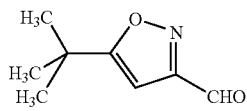

1.35 g of (5-t-butyl-isoxazol-3-yl)methanol was dissolved in 50 ml of 1,4-dioxane, and 6.42 g of manganese dioxide was then added. The mixture was stirred and heated under reflux for 10 hours. The reaction mixture was cooled to room temperature and then filtered through Celite®. The filtrate was concentrated under reduced pressure to obtain 1.29 g of 5-t-butyl-isoxazole-3-carbaldehyde.

$^1$H-NMR (CDCl$_3$, TMS, δ (ppm)): 1.39 (9H, s), 6.35 (1H, s), 10.12 (1H, s)

Reference Production Example 36-2

1-(5-t-Butyl-isoxazol-3-yl)ethanol

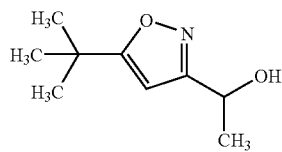

1.29 g of 5-t-butyl-isoxazole-3-carbaldehyde was dissolved in 10 ml of tetrahydrofuran, and 10 ml of a 0.93 M solution of methylmagnesium bromide in tetrahydrofuran was then added. The mixture was stirred for 1 hour under ice-cooling. After water was added, the reaction mixture was extracted with ethyl acetate. The organic layer was washed with water, dried over anhydrous magnesium sulfate, filtered and then concentrated under reduced pressure. The residue was subjected to silica gel column chromatography to obtain 1.18 g of 1-(5-t-butyl-isoxazol-3-yl)ethanol.

$^1$H-NMR (CDCl$_3$, TMS, δ (ppm)): 1.34 (9H, s), 1.54 (3H, d), 4.97 (1H, q), 5.96 (1H, s)

Reference Production Example 36-3

3-(1-Chloroethyl)-5-t-butylisoxazole

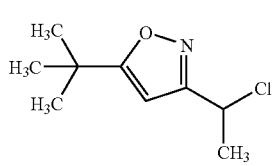

1.18 g of 1-(5-t-butyl-isoxazol-3-yl)ethanol was dissolved in 2 ml of pyridine, and 1.36 of 4-toluenesulfonyl chloride was then added under ice-cooling. The mixture was stirred for 5 hours under ice-cooling. After water was added, the reaction mixture was extracted with ethyl acetate. The organic layer was washed with water, dried over anhydrous magnesium sulfate, filtered and then concentrated under reduced pressure. The residue was subjected to silica gel column chromatography to obtain 1.60 g of 3-(1-chloroethyl)-5-t-butylisoxazole.

$^1$H-NMR (CDCl$_3$, TMS, δ (ppm)): 1.34 (9H, s), 1.54 (3H, d), 4.97 (1H, q), 5.96 (1H, s)

Reference Production Example 37-1

Ethyl 5-(hydroxymethyl)-isoxazole-3-carboxylate

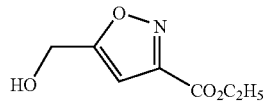

24.03 g of 2-propene-1-ol and 16.24 g of ethyl (2E)-chloro(hydroxyimino)acetate were dissolved in 100 ml of tetrahydrofuran, and 12.12 ml of triethylamine dissolved in 50 ml of tetrahydrofuran was then added dropwise at 0° C. over 30 minutes. The mixture was stirred at room temperature overnight. After aqueous saturated sodium chloride was added, the reaction mixture was separated into layers. The aqueous layer was extracted with ethyl acetate. The organic layers were combined, dried over aqueous magnesium sulfate, filtered and then concentrated under reduced pressure. The residue was subjected to silica gel column chromatography to obtain 14.22 g of ethyl 5-(hydroxymethyl)-isoxazole-3-carboxylate.

$^1$H-NMR (CDCl$_3$, TMS, δ (ppm)): 1.40 (3H, t), 2.22 (1H, b. s.), 4.42 (2H, q), 4.83 (2H, d), 6.68 (1H, s)

Reference Production Example 37-2

Ethyl 5-(t-butyldimethylsilanyloxymethyl)-isoxazole-5-carboxylate

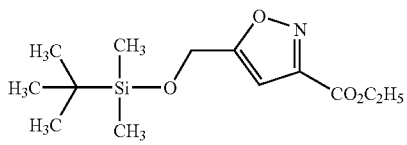

14.22 g of ethyl 5-(hydroxymethyl)-isoxazole-3-carboxylate was dissolved in 80 ml of N,N-dimethylformamide, and 6.13 g of imidazole and 13.57 g of t-butyldimethylsilyl chloride were then added. The mixture was stirred at room temperature for 10 hours. After water was added, the reaction mixture was extracted with methyl-t-butyl ether. The organic layer was washed with water, dried over anhydrous magnesium sulfate, filtered and then concentrated under reduced pressure to obtain 23.82 g of ethyl 5-(t-butyldimethylsilanyloxymethyl)-isoxazole-3-carboxylate.

$^1$H-NMR (CDCl$_3$, TMS, δ (ppm)): 0.12 (6H, s), 0.91 (9H, s), 1.52 (3H, t), 4.42 (2H, q), 4.81 (2H, s), 6.60 (1H, s)

Reference Production Example 37-3

[5-(t-Butyldimethylsilanyloxymethyl)isoxazol-3-yl]methanol

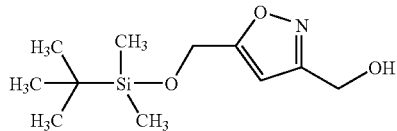

23.82 g of ethyl 5-(t-butyldimethylsilanyloxymethyl)-isoxazole-3-carboxylate was dissolved in 100 ml of ethanol, and 3.16 g of sodium borohydride was then added. The mixture was stirred at room temperature for 4 hours. After 50 ml of water was added, the reaction mixture was concentrated to 50 ml under reduced pressure. The concentrated solution was extracted with ethyl acetate. The organic layer was dried over anhydrous magnesium sulfate, filtered and then concentrated under reduced pressure. The residue was subjected to silica gel column chromatography to obtain 18.74 g of [5-(t-butyldimethylsilanyloxymethyl)isoxazol-3-yl]methanol.

$^1$H-NMR (CDCl$_3$, TMS, δ (ppm)): 0.12 (6H, s), 0.92 (9H, s), 4.62-4.68 (4H, m), 6.13 (1H, s)

Reference Production Example 37-4

3-(Chloromethyl)-5-(t-butyldimethylsilanyloxymethyl)isoxazole

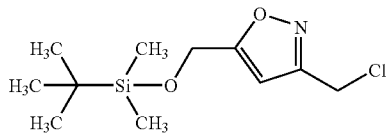

18.64 g of [5-(t-butyldimethylsilanyloxymethyl)isoxazol-3-yl]methanol was dissolved in 80 ml of pyridine, and 16.06 g of 4-toluenesulfonyl chloride was then added under ice-cooling. The mixture was stirred for 10 hours under ice-cooling. After water was added, the reaction mixture was extracted with ethyl acetate. The organic layer was washed with water, dried over anhydrous magnesium sulfate, filtered and then concentrated under reduced pressure. The residue was subjected to silica gel column chromatography to obtain 4.48 g of 5-(t-butyldimethylsilanyloxymethyl)-3-(chloromethyl)isoxazole.

$^1$H-NMR (CDCl$_3$, TMS, δ (ppm)): 0.12 (6H, s), 0.92 (9H, s), 4.58 (2H, s), 4.77 (2H, s), 6.30 (1H, s)

Reference Production Example 38-1

Ethyl 5-(1-hydroxyethyl)-isoxazole-3-carboxylate

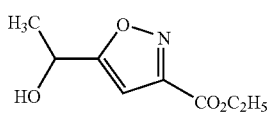

14.02 g of 1-butyn-2-ol and 7.58 g of ethyl (2E)-chloro(hydroxyimino)acetate were dissolved in 50 ml of tetrahydrofuran, and a solution of 6.06 g of triethylamine in 25 ml of tetrahydrofuran was then added dropwise at 0° C. over 30 minutes. The mixture was stirred at room temperature overnight. After aqueous saturated sodium chloride was added, the reaction mixture was separated into layers. The aqueous layer was extracted with ethyl acetate. The organic layers were combined, dried over anhydrous magnesium sulfate, filtered and then concentrated under reduced pressure. The residue was purified by silica gel column chromatography to obtain 5.67 g of ethyl 5-(1-hydroxyethyl)-isoxazole-3-carboxylate.

$^1$H-NMR (CDCl$_3$, TMS, δ (ppm)): 1.33 (3H, t), 1.57 (3H, d), 4.42 (2H, q), 5.04 (1H, q), 6.62 (1H, s)

Reference Production Example 38-2

Ethyl 5-[1-(t-butyldimethylsilanyloxy)ethyl]isoxazole-3-carboxylate

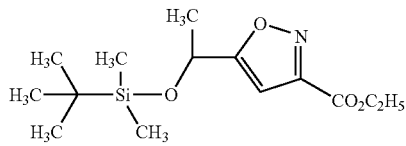

5.55 g of ethyl 5-(1-hydroxyethyl)-isoxazole-3-carboxylate was dissolved in 30 ml of N,N-dimethylformamide, and 2.38 g of imidazole and 5.28 g of t-butyldimethylsilyl chloride were then added. The mixture was stirred at room temperature for 10 hours. After water was added, the reaction mixture was extracted with methyl-t-butyl ether. The organic layer was washed with water, dried over anhydrous magnesium sulfate, filtered and then concentrated under reduced pressure to obtain 8.95 g of ethyl 5-[1-(t-butyldimethylsilanyloxy)ethyl]isoxazole-3-carboxylate.

$^1$H-NMR (CDCl$_3$, TMS, δ (ppm)): 0.08 (3H, s), 0.12 (3H, s), 0.92 (9H, s), 1.41 (3H, t), 1.54 (3H, d), 4.42 (2H, q), 4.99 (1H, q), 6.43 (1H, s)

Reference Production Example 38-3

{5-[1-(t-Butyldimethylsilanyloxy)ethyl]isoxazol-3-yl}methanol

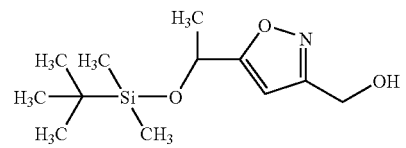

8.95 g of ethyl 5-[1-(t-butyldimethylsilanyloxy)ethyl]isoxazole-3-carboxylate was dissolved in 60 ml of ethanol, and 2.30 g of sodium borohydride was then added. The mixture was stirred at room temperature for 4 hours. After 30 ml of water was added, the reaction mixture was concentrated to 30 ml under reduced pressure. The concentrated solution was extracted with ethyl acetate. The organic layer was dried over anhydrous magnesium sulfate, filtered and then concentrated under reduced pressure. The residue was subjected to silica gel column chromatography to obtain 7.35 g of {5-[1-(t-butyldimethylsilanyloxy)ethyl]isoxazol-3-yl}methanol.

$^1$H-NMR (CDCl$_3$, TMS, δ (ppm)): 0.08 (3H, s), 0.12 (3H, s), 0.91 (9H, s), 1.48 (3H, d), 4.74 (2H, s), 4.95 (1H, q), 6.18 (1H, s)

Reference Production Example 38-4

{5-[1-(t-Butyldimethylsilanyloxy)ethyl]isoxazol-3-yl}methyl 4-methylbenzenesulfonate

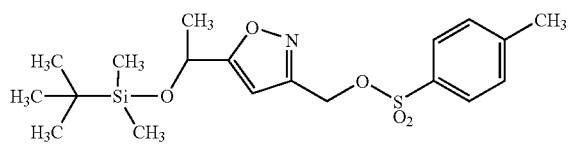

7.35 g of {5-[1-(t-butyldimethylsilanyloxy)ethyl]isoxazol-3-yl}methanol was dissolved in 50 ml of methyl-t-butyl ether, and 3.36 g of 1,4-diazabicyclo[2.2.2]octane and 5.72 g of 4-toluenesulfonyl chloride were then added under ice-cooling. The mixture was stirred for 10 hours under ice-cooling. After water was added, the reaction mixture was extracted with ethyl acetate. The organic layer was washed with water, dried over anhydrous magnesium sulfate, filtered and then concentrated under reduced pressure. The residue was subjected to silica gel column chromatography to obtain 3.60 g of {5-[1-(t-butyldimethylsilanyloxy)ethyl]isoxazol-3-yl}methyl 4-methylbenzenesulfonate.

$^1$H-NMR (CDCl$_3$, TMS, δ (ppm)): 0.05 (3H, s), 0.10 (3H, s), 0.90 (9H, s), 1.45 (3H, d), 2.45 (3H, s), 4.91 (1H, q), 5.09 (2H, s), 6.14 (1H, s), 7.34 (2H, d), 7.80 (2H, d)

Reference Production Example 39-1

Ethyl 5-acetylisoxazole-3-carboxylate

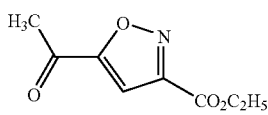

4.06 g of ethyl 5-(1-hydroxyethyl)-isoxazole-3-carboxylate was dissolved in 100 ml of 1,4-dioxane, and 15.20 g of manganese dioxide was then added. The mixture was stirred and heated under reflux for 5 hours. The reaction mixture was cooled to room temperature and then filtered through Celite®. The filtrate was concentrated under reduced pressure to obtain 3.57 g of ethyl 5-acetylisoxazole-3-carboxylate.

$^1$H-NMR (CDCl$_3$, TMS, δ (ppm)): 1.40 (3H, t), 2.67 (3H, s), 4.45 (2H, q), 7.27 (1H, s)

Reference Production Example 39-2

Ethyl 5-(1,1'-difluoroethyl)-isoxazole-3-carboxylate

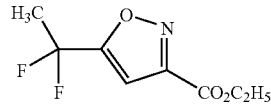

2.61 g of ethyl 5-acetylisoxazole-3-carboxylate was dissolved in 30 ml of dichloromethane, and 4.84 g of (dimethylamino)sulfate trifluoride was added under ice-cooling. The mixture was stirred at room temperature for 4 hours. After aqueous saturated sodium hydrogen carbonate was added, the reaction mixture was extracted with methyl-t-butyl ether. The organic layer was washed with water, dried over anhydrous magnesium sulfate, filtered and concentrated under reduced pressure. The residue was subjected to silica gel column chromatography to obtain 2.90 g of ethyl 5-(1,1-difluoroethyl)-isoxazole-3-carboxylate.

$^1$H-NMR (CDCl$_3$, TMS, δ (ppm)): 1.41 (3H, t), 2.01-2.06 (3H, m), 4.44 (2H, q), 6.91 (1H, s)

Reference Production Example 39-3

[5-(1,1-Difluoroethyl)-3-yl]methanol

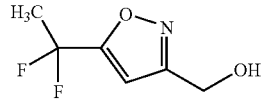

2.90 g of ethyl 5-(1,1-difluoroethyl)-isoxazole-3-carboxylate was dissolved in 30 ml of ethanol, and 1.02 g of sodium borohydride was then added. The mixture was stirred at room temperature for 4 hours. After 30 ml of water was added, the reaction mixture was concentrated to 30 ml under reduced pressure. The concentrated solution was extracted with ethyl acetate. The organic layer was dried over anhydrous magnesium sulfate, filtered and then concentrated under reduced pressure. The residue was subjected to silica gel column chromatography to obtain 2.00 g of [5-(1,1-difluoroethyl)-3-yl]methanol.

$^1$H-NMR (CDCl$_3$, TMS, δ (ppm)): 1.97 (3H, t), 4.79 (2H, s), 6.56 (1H, s)

Reference Production Example 39-4

3-(Chloromethyl)-5-(1,1-difluoroethyl)isoxazole

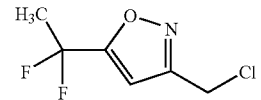

1.00 g of [5-(1,1-difluoroethyl)isoxazol-3-yl]methanol was dissolved in 10 ml of dichloromethane, and 0.8 ml of thionyl chloride was then added. The mixture was stirred at room temperature for 1 hour. The reaction mixture was concentrated under reduced pressure to obtain 1.11 g of 3-(chloromethyl)-5-(1,1-difluoroethyl)isoxazole.

$^1$H-NMR (CDCl$_3$, TMS, δ(ppm)): 1.99 (3H, t), 4.61 (2H, s), 6.61 (1H, s)

Reference Production Example 40-1

Ethyl 5-(1-hydroxy-1-methylethyl)isoxazole-3-carboxylate

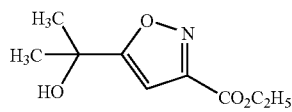

57.35 g of 2-methyl-1-butyn-2-ol and 25.83 g of ethyl (2E)-chloro(hydroxyimino)acetate were dissolved in 120 ml of tetrahydrofuran, and a solution of 17.25 g of triethylamine in 50 ml of tetrahydrofuran was then added dropwise at 0° C. over 1 hour. The mixture was stirred at room temperature overnight. After aqueous saturated sodium chloride was added, the reaction mixture was separated into layers. The aqueous layer was extracted with ethyl acetate, and the organic layers were combined, dried over anhydrous magnesium sulfate, filtered and then concentrated under reduced pressure. The residue was subjected to silica gel column chromatography to obtain 17.62 g of ethyl 5-(1-hydroxy-1-methylethyl)isoxazole-3-carboxylate.

$^1$H-NMR (CDCl$_3$, TMS, δ (ppm)): 1.39 (3H, t), 1.66 (6H, s), 4.41 (2H, q), 6.58 (1H, s)

Reference Production Example 40-2

[5-(1-Hydroxy-1-methylethyl)isoxazol-3-yl]methanol

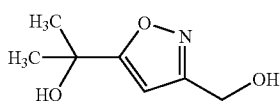

9.96 g of ethyl 5-(1-hydroxy-1-methylethyl)isoxazole-5-carboxylate was dissolved in 200 ml of ethanol, and 3.78 g of sodium borohydride was then added. The mixture was stirred at room temperature for 10 hours. After 50 ml of water was added, the reaction mixture was concentrated to 50 ml under reduced pressure. The concentrated solution was extracted with ethyl acetate. The organic layer was dried over anhydrous magnesium sulfate, filtered and then concentrated under reduced-pressure. The residue was subjected to silica gel column chromatography to obtain 6.17 g of [5-(1-hydroxy-1-methylethyl)isoxazol-3-yl]methanol.

$^1$H-NMR (CDCl$_3$, TMS, δ (ppm)): 1.63 (6H, s), 2.15 (1H, br. s), 4.74 (2H, d), 6.22 (1H, s)

Reference Production Example 40-3

5-(1-Hydroxy-1-methylethyl)isoxazol-3-carbaldehyde

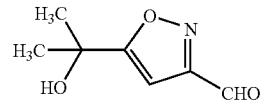

5.38 g of [5-(1-hydroxy-1-methylethyl)isoxazol-3-yl]methanol was dissolved in 100 ml of 1,4-dioxane, and 29.74 g of manganese dioxide was then added. The mixture was stirred and heated under reflux for 10 hours. The reaction mixture was cooled to room temperature and then filtered through Celite®. The filtrate was concentrated under reduced pressure to obtain 4.63 g of 5-(1-hydroxy-1-methylethyl)-isoxazole-3-carbaldehyde.

$^1$H-NMR (CDCl$_3$, TMS, δ (ppm)): 1.67 (6H, s), 6.56 (1H, s), 10.14 (1H, s)

Reference Production Example 40-4

{[5-(1-Hydroxy-1-methylethyl)isoxazol-3-yl]methylidene}malononitrile

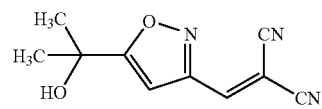

4.63 g of 5-(1-hydroxy-1-methylethyl)isoxazole-3-carbaldehyde was dissolved in 50 ml of ethanol, and 1.98 g of malononitrile was then added. The mixture was stirred at room temperature for 5 hours. The reaction mixture was concentrated under reduced pressure, and the residue was subjected to silica gel column chromatography to obtain 5.35 g of {[5-(1-hydroxy-1-methylethyl)-isoxazol-3-yl]methylidene}malononitrile.

$^1$H-NMR (CDCl$_3$, TMS, δ (ppm)): 1.68 (6H, s), 7.01 (1H, s), 7.92 (1H, s)

Reference Production Example 40-5

{[5-(1-Hydroxy-1-methylethyl)-isoxazol-3-yl]methyl}malononitrile

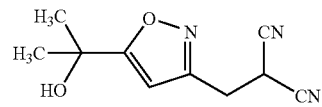

9.91 g of {[5-(1-hydroxy-1-methylethyl)-isoxazol-3-yl]methylidene}malononitrile was dissolved in 100 ml of tetrahydrofuran, and 3.78 g of sodium borohydride was then added under ice-cooling. The mixture was stirred for 8 hours under ice-cooling. The reaction mixture was added to 0.5 N hydrochloric acid over 30 minutes and then extracted with ethyl acetate. The extract was dried over anhydrous magnesium sulfate, filtered and then concentrated under reduced pressure. The residue was subjected to silica gel column chromatography to obtain 5.38 g of {[5-(1-hydroxy-1-methylethyl)-isoxazol-3-yl]methyl}malononitrile.

$^1$H-NMR (CDCl$_3$, TMS, δ (ppm)): 1.64 (6H, s), 3.40 (2H, d), 4.25 (1H, t), 6.25 (1H, s)

Reference Production Example 41

{1-[5-(1-Hydroxy-1-methylethyl)-isoxazol-3-yl]ethyl}malononitrile

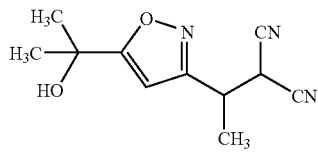

1.02 g of {[5-(1-hydroxy-1-methylethyl)-isoxazol-3-yl]methylidene}malononitrile was dissolved in 50 ml of 1,4-dioxane. Thereto, 0.05 g of copper(I) iodide was added and 9 ml of a 1.4 M solution of methylmagnesium bromide in tetrahydrofuran was then added under ice-cooling. The mixture was stirred for 1 hour under ice-cooling. The reaction mixture was added to 0.1 M hydrochloric acid and then extracted with ethyl acetate. The organic layer was dried over anhydrous magnesium sulfate, filtered and then concentrated under reduced pressure. The residue was subjected to silica gel column chromatography to obtain 0.53 g of {1-[5-(1-hydroxy-1-methylethyl)-isoxazol-3-yl]methyl}malononitrile.

$^1$H-NMR (CDCl$_3$, TMS, δ (ppm)): 1.61-1.68 (9H, m), 3.57-3.65 (1H, m), 4.27 (1H, d), 6.23 (1H, s)

Reference Production Example 42

{1-[5-(1-Hydroxy-1-methylethyl)-isoxazol-3-yl]propyl}malononitrile

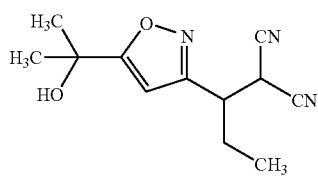

1.02 g of {[5-(1-hydroxy-1-methylethyl)-isoxazol-3-yl]methylidene}malononitrile was dissolved in 50 ml of 1,4-dioxane. Thereto, 0.05 g of copper(I) iodide was added and ml of a 3 M solution of ethylmagnesium bromide in tetrahydrofuran was then added under ice-cooling. The mixture was stirred for 1 hour under ice-cooling. The reaction mixture was added to 0.1 M hydrochloric acid and then extracted with ethyl acetate. The organic layer was dried over anhydrous magnesium sulfate, filtered and then concentrated under reduced pressure. The residue was subjected to silica gel column chromatography to obtain 0.40 g of {1-[5-(1-hydroxy-1-methylethyl)-isoxazol-3-yl]propyl}malononitrile.

$^1$H-NMR (CDCl$_3$, TMS, δ (ppm)): 1.24 (3H, t), 1.70 (6H, s), 1.96-2.13 (2H, m), 3.41-3.45 (1H, m), 4.11 (1H, d), 6.25 (1H, s)

Reference Production Example 43

{1-[5-(1-Hydroxy-1-methylethyl)-isoxazol-3-yl]-2-methylpropyl}malononitrile

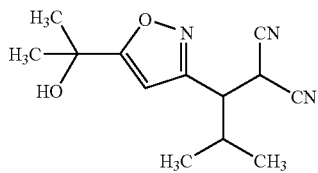

1.02 g of {[5-(1-hydroxy-1-methylethyl)-isoxazol-3-yl]methylidene}malononitrile was dissolved in 50 ml of 1,4-dioxane. Thereto, 0.05 g of copper(I) iodide was added and 15 ml of a 1 M solution of i-propylmagnesium bromide in tetrahydrofuran was then added under ice-cooling. The mixture was stirred for 1 hour under ice-cooling. The reaction mixture was added to 0.1 M hydrochloric acid and then extracted with ethyl acetate. The extract was dried over anhydrous magnesium sulfate, filtered and then concentrated under reduced pressure. The residue was subjected to silica gel column chromatography to obtain 0.40 g of {1-[5-(1-hydroxy-1-methylethyl)-isoxazol-3-yl]-2-methylpropyl}malononitrile.

$^1$H-NMR (CDCl$_3$, TMS, δ (ppm)): 0.91 (3H, d), 1.12 (3H, d), 1.65 (6H, s), 2.31-2.40 (1H, m), 3.27 (1H, t), 4.25 (1H, d), 6.23 (1H, s)

Reference Production Example 44

{1-[5-(1-Hydroxy-1-methylethyl)-isoxazol-3-yl]allyl}malononitrile

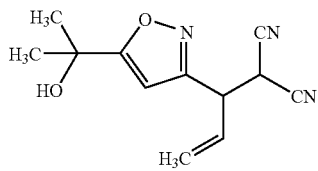

2.26 g of {[5-(1-hydroxy-1-methylethyl)-isoxazol-3-yl]methylidene}malononitrile was dissolved in 50 ml of 1,4-dioxane. Thereto, 0.08 g of copper(I) iodide was added and 18.6 ml of a 1.4 M solution of allylmagnesium chloride in tetrahydrofuran was then added under ice-cooling. The mixture was stirred for 1 hour under ice-cooling. The reaction mixture was added to 0.1 M hydrochloric acid and then extracted with ethyl acetate. The organic layer was dried over anhydrous magnesium sulfate, filtered and then concentrated under reduced pressure. The residue was subjected to silica gel column chromatography to obtain 0.56 g of {1-[5-(1-hydroxy-1-methylethyl)-isoxazol-3-yl]allyl}malononitrile.

$^1$H-NMR (CDCl$_3$, TMS, δ (ppm)): 1.64 (6H, s), 4.05-4.08 (1H, m), 4.40 (1H, d), 5.55-5.62 (2H, m), 5.97-6.06 (1H, m), 6.18 (1H, s)

Reference Production Example 45-1

Ethyl 5-[1-methyl-1-(2-propynyloxy)ethyl]isoxazol-3-carboxylate

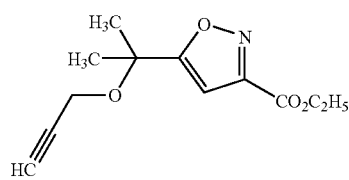

2.00 g of ethyl 5-(1-hydroxy-1-methylethyl)isoxazole-3-carboxylate was dissolved in 20 ml of tetrahydrofuran, and 0.44 g of sodium hydride and 1.32 g of 3-bromo-1-propyne were then added under ice-cooling. The mixture was stirred at room temperature for 5 hours. After water was added, the reaction mixture was extracted with methyl-t-butyl ether. The organic layer was washed with water, dried over anhydrous magnesium sulfate, filtered and then concentrated under reduced pressure. The residue was subjected to silica gel column chromatography and then recrystallized from hexane-ethyl acetate to obtain 0.25 g of ethyl 5-[1-methyl-1-(2-propynyloxy)ethyl]isoxazole-3-carboxylate.

$^1$H-NMR (CDCl$_3$, TMS, δ (ppm)): 1.41 (3H, t), 1.66 (6H, s), 2.39 (1H, t), 4.00 (2H, d), 4.42 (2H, q), 6.64 (1H, s)

Reference Production Example 45-2

{5-[1-Methyl-1-(2-propynyloxy)ethyl]isoxazol-3-yl}methanol

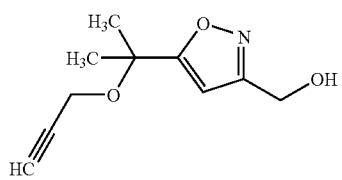

0.25 g of ethyl 5-[1-methyl-1-(2-propynyloxy)ethyl]isoxazole-3-carboxylate was dissolved in 2 ml of ethanol, and 0.1 g of sodium borohydride was then added. The mixture was stirred at room temperature for 5 hours. After 20 ml of water was added, the reaction mixture was extracted with ethyl acetate. The organic layer was dried over anhydrous magnesium sulfate, filtered and then concentrated under reduced pressure. The residue was subjected to silica gel column chromatography to obtain 0.20 g of {5-[1-methyl-1-(2-propynyloxy)ethyl]isoxazol-3-yl}methanol.

$^1$H-NMR (CDCl$_3$, TMS, δ (ppm)): 1.63 (6H, s), 2.39 (1H, t), 4.01 (2H, d), 4.76 (2H, s), 6.29 (1H, s)

Reference Production Example 45-3

3-(Chloromethyl)-5-[1-methyl-1-(2-propynyloxy)ethyl]isoxazole

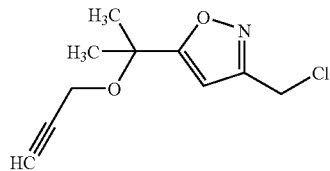

0.20 g of {5-[1-methyl-1-(2-propynyloxy)ethyl]isoxazol-3-yl}methanol was dissolved in 5 ml of dichloromethane, and 0.5 ml of thionyl chloride was then added. The mixture was stirred at room temperature for 3 hours. The reaction mixture was concentrated under reduced pressure to obtain 0.21 g of 3-(chloromethyl)-5-[1-methyl-1-(2-propynyloxy)ethyl]isoxazole.

$^1$H-NMR (CDCl$_3$, TMS, δ (ppm)): 1.64 (6H, s), 2.39 (1H, t), 4.02 (2H, d), 4.58 (2H, s), 6.33 (1H, s)

Reference Production Example 46-1

Methyl 3-methoxyisoxazole-5-carboxylate

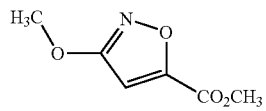

2.86 g of methyl 3-hydroxyisoxazole-5-carboxylate was dissolved in 10 ml of N,N-dimethylformamide, and 4.25 g of methyl iodide and 4.15 g of potassium carbonate were then added under ice-cooling. The mixture was stirred at room temperature overnight. The reaction mixture was added to 0.1 M hydrochloric acid and then extracted with ethyl acetate. The organic layer was dried over anhydrous magnesium sulfate, filtered and then concentrated under reduced pressure. The residue was subjected to silica gel column chromatography to obtain 2.23 g of methyl 3-methoxyisoxazole-5-carboxylate.

$^1$H-NMR (CDCl$_3$, TMS, δ (ppm)): 3.93 (3H, s), 4.05 (3H, s), 6.54 (1H, s)

Reference Production Example 46-2

(3-Methoxyisoxazol-5-yl)methanol

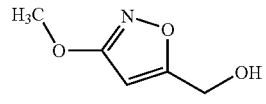

2.23 g of methyl 3-methoxyisoxazole-5-carboxylate was dissolved in 30 ml of ethanol, and 0.60 g of sodium borohydride was then added ice-cooling. The mixture was stirred for 8 hours under ice-cooling. After water was added under ice-cooling, the reaction mixture was concentrated under reduced pressure and then extracted with ethyl acetate. The organic layer was dried over anhydrous magnesium sulfate, filtered and then concentrated under reduced pressure. The residue was subjected to silica gel column chromatography to obtain 1.55 g of (3-methoxyisoxazol-5-yl)methanol.

$^1$H-NMR (CDCl$_3$, TMS, δ (ppm)): 3.96 (3H, s), 4.66 (2H, s), 5.88 (1H, s)

Reference Production Example 46-3

5-(Chloromethyl)-3-methoxyisoxazol

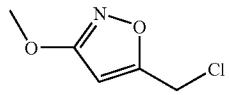

1.55 g of (3-methoxyisoxazol-5-yl)methanol was dissolved in 30 ml of dichloromethane, and 2 ml of thionyl chloride was then added. The mixture was stirred at room temperature for 1 hour. The reaction mixture was concentrated under reduced pressure to obtain 1.30 g of 5-(chloromethyl)-3-methoxyisoxazole.

$^1$H-NMR (CDCl$_3$, TMS, δ (ppm)): 3.98 (3H, s), 4.49 (2H, s), 5.97 (1H, s)

Reference Production Example 47-1

(2-Ethylthio-1-methylimidazol-5-yl)methanol

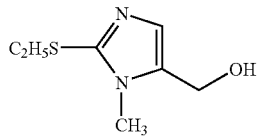

4.33 g of (1-methyl-2-mercaptoimidazol-5-yl)methanol was added to 90 ml of tetrahydrofuran. Thereto 3.70 g of potassium t-butoxide and 5.15 g of ethyl iodide were then added under ice-cooling. The mixture was stirred at room temperature for 1 hour. The reaction mixture was filtered and the filtrate was concentrated under reduced pressure. The residue was subjected to silica gel column chromatography to obtain 4.82 g of (2-ethylthio-1-methylimidazol-5-yl)methanol.

$^1$H-NMR (CDCl$_3$, TMS, δ (ppm)): 1.32 (3H, t), 3.06 (2H, d), 3.24 (2H, q), 3.64 (3H, s), 7.00 (1H, s)

Reference Production Example 47-2

2-Ethylthio-1-methylimidazole-5-carbaldehyde

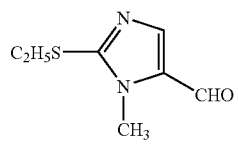

5.50 g of (2-ethylthio-1-methylimidazol-5-yl)methanol was dissolved in 100 ml of 1,4-dioxane, and 24.34 g of manganese dioxide was then added. The mixture was stirred and heated under reflux for 7 hours. The reaction mixture was cooled to room temperature and then filtered through Celite®. The filtrate was concentrated under reduced pressure to obtain 5.13 g of 2-ethylthio-1-methylimidazole-5-carbaldehyde.

$^1$H-NMR (CDCl$_3$, TMS, δ (ppm)): 1.41 (3H, t), 3.26 (2H, q), 3.83 (3H, s), 7.73 (1H, s), 9.58 (1H, s)

Reference Production Example 47-3

[(2-Ethylthio-1-methylimidazol-5-yl)methylidene]malononitrile

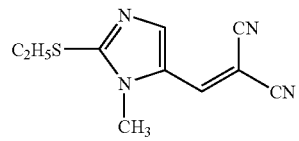

5.13 g of 2-ethylthio-1-methylimidazole-5-carbaldehyde was dissolved in 30 ml of ethanol, and 2.00 g of malononitrile was then added. The mixture was stirred at room temperature for 3 hours. The reaction mixture was concentrated under reduced pressure. The residue was subjected to silica gel column chromatography to obtain 2.51 g of [(2-ethylthio-1-methylimidazol-3-yl)methylidene]malononitrile.

$^1$H-NMR (CDCl$_3$, TMS, δ (ppm)): 1.38 (3H, t), 3.30 (2H, q), 3.56 (3H, s), 7.39 (1H, s), 8.46 (1H, s)

Reference Production Example 47-4

{(2-Ethylthio-1-methylimidazol-5-yl)methyl}malononitrile

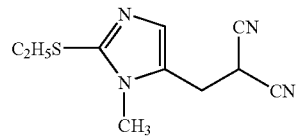

0.44 g of [(2-ethylthio-1-methylimidazol-5-yl)methylidene]malononitrile was dissolved in 10 ml of tetrahydrofuran, and 0.10 g of sodium borohydride was then added under ice-cooling. The mixture was stirred for 4 hours under ice-cooling. The reaction mixture was added to 0.5 N hydrochloric acid under ice-cooling and then extracted with ethyl acetate. The organic layer was dried over anhydrous magnesium sulfate, filtered and then concentrated under reduced pressure. The residue was subjected to silica gel column chromatography to obtain 0.32 g of [(2-ethylthio-1-methylimidazol-5-yl)methyl]malononitrile.

$^1$H-NMR (CDCl$_3$, TMS, δ (ppm)): 1.31 (3H, t), 3.06 (2H, q), 3.34 (2H, d), 3.59 (3H, s), 3.93 (1H, t), 7.14 (1H, s)

Then, Formulation Examples will be described. The term "part" represents a part by weight. In addition, the present compound will be designated by the aforementioned compound numbers.

Formulation Example 1

9 Parts of any one of the present compounds (1) to (70) is dissolved in 37.5 pats of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 2

5 Parts of SORPOL 5060 (registered trade name for TOHO Chemical Industry Co., LTD.) is added to 40 parts of any one of the present compounds (1) to (70) and mixed thoroughly. Then, 32 parts of CARPLEX #80 (registered trade name for Shionogi & Co., Ltd., synthetic anhydrous silicon oxide fine powder) and 23 parts of 300 mesh diatomaceous earth are added thereto and mixed with a juice mixer to obtain a wettable preparation.

Formulation Example 3

3 Parts of any one of the present compounds (1) to (70), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 4

4.5 Parts of any one of the present compounds (1) to (70), 1 part of synthetic hydrous silicon oxide fine powder, 1 part of Dorires B (manufactured by Sankyo) as a flocculant, and 7 parts of clay are mixed thoroughly with a mortar and then by stirring with a juice mixer. To the resultant mixture 86.5 parts of cut clay is added and mixed by stirring thoroughly to obtain a powder.

Formulation Example 5

10 Parts of any one of the present compounds (1) to (70), 35 parts of white carbon containing 50 parts of polyoxyethylene alkylether sulfate ammonium salt, and 55 parts of water are mixed and then finely-divided by a wet grinding method to obtain a preparation.

Formulation Example 6

0.5 Parts of any one of the present compounds (1) to (70) is dissolved in 10 parts of dichloromethane. This solution is mixed with 89.5 parts of Isopar M (isoparaffin: registered trade name for Exxon Chemical) to obtain an oil.

Formulation Example 7

0.1 Parts of any one of the present compounds (1) to (70) and 49.9 parts of NEO-THIOZOL (Chuo Kasei Co., Ltd.) are placed in an aerosol can. An aerosol valve is fitted to the can and the can is then charged with 25 parts of dimethyl ether and 25 parts of LPG. The can is shaken and an actuator is fitted to the can to obtain an oily aerosol.

Formulation Example 8

An aerosol container is charged with a mixture of 0.6 parts of any one of the present compounds (1) to (70), 0.01 part of BHT, 5 parts of xylene, 3.39 parts of a deodorized kerosene and 1 part of an emulsifying agent [Atmos 300 (registered trade name for Atmos Chemical Ltd.)] and 50 parts of distilled water. A valve part is attached to the container and the container is then charged with 40 parts of a propellant (LPG) through the valve under increased pressure to obtain an aqueous aerosol.

Then, it will be demonstrated by Experimental Examples that the present compound is effective as the active ingredient of a pesticidal composition. The present compound will be designated by the aforementioned compound numbers.

Experimental Example 1

Preparations of the present compounds (1), (2), (3), (4), (5), (6), (8), (9), (11), (12), (13), (15), (16), (17), (18), (19), (21), (22), (23), (24), (25), (26), (27), (29), (31), (32), (34), (35), (36), (37), (38), (39), (40), (41), (42), (43), (45), (47), (50), (52), (53), (54), (62), (64), (65), (67) and (68) obtained according to Formulation Example 5 were diluted so that the active ingredient concentration was 500 ppm to prepare experimental pesticidal solutions.

In a polyethylene cup, 50 g of molding Bonsoru 2 (manufactured by Sumitomo Chemical Co., Ltd.) was put and 10 to 15 seeds of rice were planted. The rice plants were grown until the second foliage leaf was developed and then cut into the same height of 5 cm. The experimental pesticidal solution prepared as described above was sprayed in an amount of 20 ml/cup on the rice plants. After the pesticidal solution sprayed onto the rice plants was dried, the rice plants were put into a plastic cup for preventing the escape of test pests. 30 first-instar larvae of *Nilaparvata lugens* were released into the plastic cup and the cup was sealed with a lid and then left in a greenhouse (25° C.). On the sixth day after release of *Nilaparvata lugens* larvae, the number of parasitic *Nilaparvata lugens* on the rice plants was examined.

As a result, in treatments with the present compounds (1), (2), (3), (4), (5), (6), (8), (9), (11), (12), (13), (15), (16), (17), (18), (19), (21), (22), (23), (24), (25), (26), (27), (29), (31), (32), (34), (35), (36), (37), (38), (39), (40), (41), (42), (43), (45), (47), (50), (52), (53), (54), (62), (64), (65), (67) and (68), the number of the parasitic pest was 3 or less.

Experimental Example 2

Preparations of the present compounds (1), (2), (4), (5), (6), (8), (11), (15), (17), (19), (24), (25), (27), (35), (36), (37), (38), (39), (40), (41), (42), (45), (47) (48), (49), (50), (52), (53), (54), (62), (65), (66), (67) and (70) obtained according to Formulation Example 5 were diluted with water so that the active ingredient concentration was 500 ppm to prepare experimental pesticidal solutions.

In a polyethylene cup cucumber was planted and grown until the first foliage leaf was developed. About 20 *Aphis gossypii* were made to parasitize the cucumber. One day after, the pesticidal solution was sprayed in an amount of 20 ml/cup on the cucumber. Sixth days after, the number of the *Aphis gossypii* was examined.

As a result, in treatments with the present compounds (1), (2), (4), (5), (6), (8), (11), (15), (17), (19), (24), (25), (27), (35), (36), (37), (38), (39), (40), (41), (42), (45), (47), (48), (49), (50), (52), (53), (54), (62), (65), (66), (67) and (70), the number of the parasitic pest six days after the treatments was 3 or less.

Experimental Example 3

Preparations of the present compounds (1), (2), (3), (4), (5), (6), (8), (9), (10), (11), (12), (13), (14), (15), (16), (17), (18), (19), (21), (22), (23), (24), (25), (26), (27), (31), (34), (35), (36), (37), (38), (39), (40), (42), (47), (50), (52), (54), (66), (67) and (68) obtained according to Formulation Example 5 were diluted with water so that the active ingredient concentration was 500 ppm to prepare experimental pesticidal solutions.

A filter paper having a diameter of 5.5 cm was spread on the bottom of a polyethylene cup having a diameter of 5.5 cm and 0.7 ml of the experimental pesticidal solution was added dropwise onto the filter paper. As a bait 30 mg of sucrose was uniformly placed on the filter paper. Into the polyethylene cup, 10 female *Musca domestics* imagoes were released and the cup was sealed with a lid. After 24 hours, the number of surviving *Musca domestics* was examined and the death rate of the pest was calculated.

As a result, in treatments with the present compounds (1), (2), (3), (4), (5), (6), (8), (9), (10), (11), (12), (13), (14), (15), (16), (17), (18), (19), (21), (22), (23), (24), (25), (26), (27), (31), (34), (35), (36), (37), (38), (39), (40), (42), (47), (50), (52), (54), (66), (67) and (68), the death rate of the pest was 90% or more.

Experimental Example 4

Preparations of the present compounds (2), (4), (5), (6), (8), (9), (11), (12), (13), (15), (17), (18), (19), (21), (24), (25), (26), (27), (35), (36), (37), (38), (40), (41), (42), (47), (50), (52), (54), (62), (64), (65), (66) and (68) obtained according to Formulation Example 5 were diluted with water so that the active ingredient concentration was 500 ppm to prepare experimental pesticidal solutions.

A filter paper having a diameter of 5.5 cm was spread on the bottom of a polyethylene cup having a diameter of 5.5 cm and 0.7 ml of the experimental pesticidal solution was added dropwise onto the filter paper. As a bait 30 mg of sucrose was uniformly placed on the filter paper. Into the polyethylene cup, two male *Blattalla gexmanica* images were released and the cup was sealed with a lid. After 6 days, the number of surviving *Blattalla germanica* was examined and the death rate of the pest was calculated.

As a result, in treatments with the present compounds (2), (4), (5), (6), (8), (9), (11), (12), (13), (15), (17), (18), (19), (21), (24), (25), (26), (27), (35), (36), (37), (38), (40), (41), (42), (47), (50), (52), (54), (62), (64), (65), (66) and (68), the death rate of the pest was 100%.

Experimental Example 5

Preparations of the present compounds (1), (2), (4), (5), (6), (8), (9), (11), (12), (13), (14), (15), (16), (17), (18), (19), (21), (22), (23), (24), (25), (26), (27), (31), (33), (34), (35), (36), (37), (38), (39), (40), (42), (43), (47), (48), (50), (52), (53), (54), (62), (64), (65), (66), (67), (68) and (70) obtained according to Formulation Example 5 were diluted with water so that the active ingredient concentration was 500 ppm to prepare experimental pesticidal solutions.

0.7 ml of the experimental pesticidal solution was added to 100 mL of ion-exchanged water (active ingredient concentration: 3.5 ppm). Into the solution, 20 last-instar larvae of *Culex pipiens pallens* were released. After one day, the surviving number was examined and the death rate of the pest was calculated.

As a result, in treatments with the present compounds (1), (2), (4), (5), (6), (8), (9), (11), (12), (13), (14), (15), (16), (17), (18), (19), (21), (22), (23), (24), (25), (26), (27), (31), (33), (34), (35), (36), (37), (38), (39), (40), (42), (43), (47), (48), (50), (52), (53), (54), (62), (64), (65), (66), (67), (68) and (70), the death rate of the pest was 95% or more.

INDUSTRIAL APPLICABILITY

The malononitrile compound represented by the formula (I) is useful as an active ingredient of a pesticidal composition.

The invention claimed is:

1. A malononitrile compound which is represented by any one of the formula (II-i) to (II-xiii):

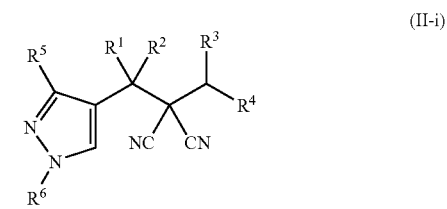

(II-i)

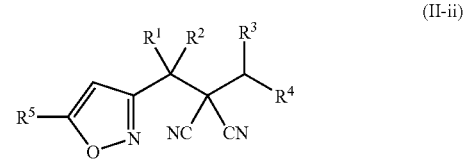

(II-ii)

(II-iii)

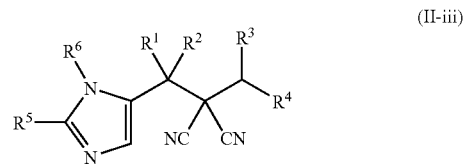

(II-iv)

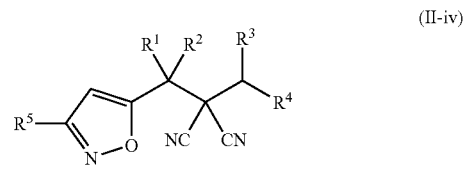

(II-v)

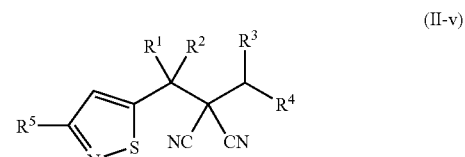

(II-vi)

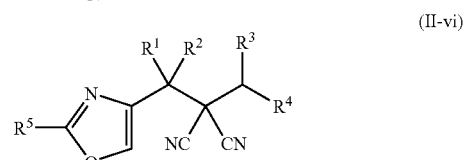

(II-vii)

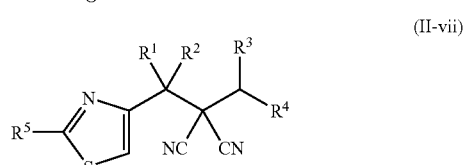

(II-viii)

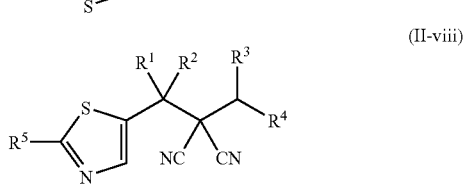

-continued

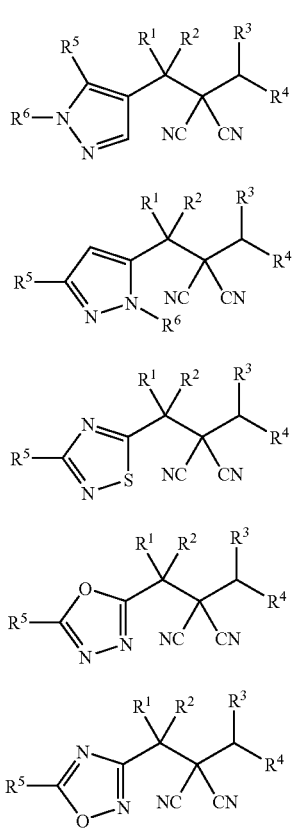

wherein R¹ represents C1-C5 alkyl optionally substituted with one or more halogen, C2-C5 alkenyl optionally substituted with one or more halogen, C2-C5 alkynyl optionally substituted with one or more halogen, or hydrogen, R² represents C1-C5 alkyl optionally substituted with one or more halogen, C1-C5 alkoxy optionally substituted with one or more halogen, C2-C5 alkenyl optionally substituted with one or more halogen, C2-C5 alkynyl optionally substituted with one or more halogen, cyano or hydrogen, R³ and R⁴ each represent C1-C5 alkyl optionally substituted with one or more halogen, C2-C5 alkenyl optionally substituted with one or more halogen, C2-C5 alkynyl optionally substituted with one or more halogen, C3-C5 cycloalkyl optionally substituted with one or more halogen, C4-C5 cycloalkenyl optionally substituted with one or more halogen, or hydrogen, or R³ and R⁴ are taken together to represent C2-C6 alkanediyl optionally substituted with one or more halogen or C4-C6 alkenediyl optionally substituted with one or more halogen, R⁵ represents halogen, cyano, nitro, formyl, SF₅, C1-C5 alkyl optionally substituted with one or more halogen, C2-C5 alkenyl optionally substituted with one or more halogen, C2-C5 alkynyl optionally substituted with one or more halogen, C3-C6 cycloalkyl optionally substituted with one or more halogen or one or more C1-C3 alkyl, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C3-C5 alkenylthio optionally substituted with one or more halogen, C3-C5 alkynylthio optionally substituted with one or more halogen, C1-C5 alkylsulfinyl optionally substituted with one or more halogen, C1-C5 alkylsulfonyl optionally substituted with one or more halogen, C2-C6 alkylcarbonyl optionally substituted with one or more halogen, a group represented by C(OR¹⁹)R²⁰R²¹, or hydrogen, R⁶ represents C1-C5 alkyl optionally substituted with one or more halogen, R¹⁹ represents C1-C5 alkyl optionally substituted with one or more halogen, C3-C5 alkynyl optionally substituted with one or more halogen, or hydrogen, and R²⁰ and R²¹ each represent C1-C5 alkyl optionally substituted with one or more halogen, or hydrogen.

2. The malononitrile compound according to claim 1, wherein R¹ is hydrogen,

R² is C1-C5 alkyl optionally substituted with one or more halogen, or hydrogen,

R³ and R⁴ each are C1-C5 alkyl optionally substituted with one or more halogen, C2-C5 alkenyl optionally substituted with one or more halogen, or hydrogen, R⁵ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by C(OR¹⁹)R²⁰R²¹, or hydrogen, R⁶ is C1-C5 alkyl optionally substituted with one or more halogen, R¹⁹ represents C1-C5 alkyl optionally substituted with one or more halogen, C3-C5 alkynyl optionally substituted with one or more halogen, or hydrogen, and R²⁰ and R²¹ each represent C1-C5 alkyl optionally substituted with one or more halogen, or hydrogen.

3. The malononitrile compound according to claim 1, which is represented by the formula (II-i):

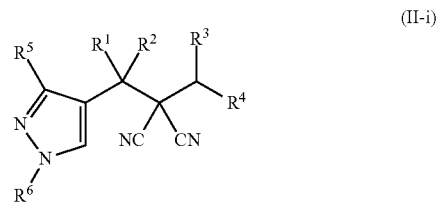

wherein R¹, R², R³, R⁴, R⁵ and R⁶ are as defined in claim 1.

4. The malononitrile compound according to claim 1, which is represented by the formula (II-ii):

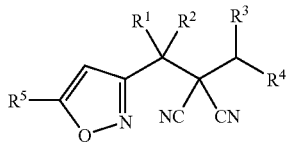

(II-ii)

wherein $R^1$, $R^2$, $R^3$, $R^4$ and $R^5$ are as defined in claim 1.

5. The malononitrile compound according to claim 1, which is represented by the formula (II-iii):

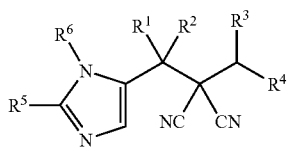

(II-iii)

wherein $R^1$, $R^2$, $R^3$, $R^4$, $R^5$ and $R^6$ are as defined in claim 1.

6. The malononitrile compound according to claim 1, which is represented by the formula (II-iv):

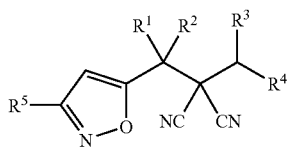

(II-iv)

wherein $R^1$, $R^2$, $R^3$, $R^4$ and $R^5$ are as defined in claim 1.

7. The malononitrile compound according to claim 1, which is represented by the formula (II-v):

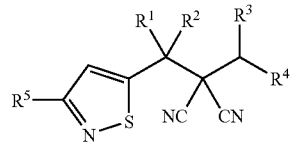

(II-v)

wherein $R^1$, $R^2$, $R^3$, $R^4$ and $R^5$ are as defined in claim 1.

8. The malononitrile compound according to claim 1, which is represented by the formula (II-vi):

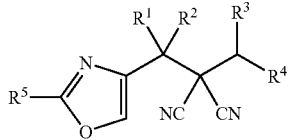

(II-vi)

wherein $R^1$, $R^2$, $R^3$, $R^4$ and $R^5$ are as defined in claim 1.

9. The malononitrile compound according to claim 1, which is represented by the formula (II-vii):

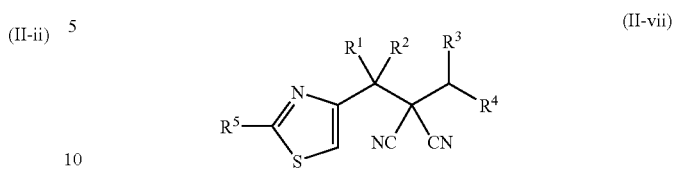

(II-vii)

wherein $R^1$, $R^2$, $R^3$, $R^4$ and $R^5$ are as defined in claim 1.

10. The malononitrile compound according to claim 1, which is represented by the formula (II-viii):

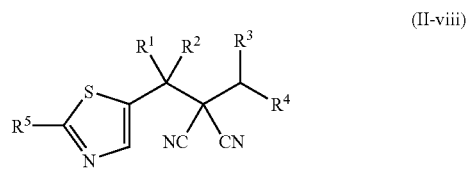

(II-viii)

wherein $R^1$, $R^2$, $R^3$, $R^4$ and $R^5$ are as defined in claim 1.

11. The malononitrile compound according to claim 1, which is represented by the formula (II-ix):

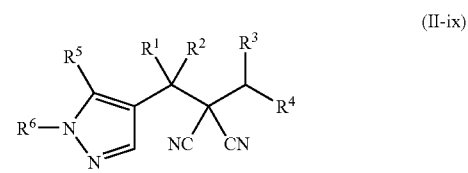

(II-ix)

wherein $R^1$, $R^2$, $R^3$, $R^4$, $R^5$ and $R^6$ are as defined in claim 1.

12. The malononitrile compound according to claim 3, wherein $R^1$ is hydrogen,
- $R^2$ is C1-C5 alkyl optionally substituted with one or more halogen, or hydrogen,
- $R^3$ and $R^4$ each are C1-C5 alkyl optionally substituted with one or more halogen, C2-C5 alkenyl optionally substituted with one or more halogen, or hydrogen,
- $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen,
- $R^6$ is C1-C5 alkyl optionally substituted with one or more halogen,
- $R^{19}$ represents C1-C5 alkyl optionally substituted with one or more halogen, C3-C5 alkynyl optionally substituted with one or more halogen, or hydrogen, and
- $R^{20}$ and $R^{21}$ each represent C1-C5 alkyl optionally substituted with one or more halogen, or hydrogen.

13. A pesticidal composition, which comprises an effective amount of the malononitrile compound according to claim 1 and an inert carrier.

14. A method for controlling an arthropod pest, which comprises applying an effective amount of the malononitrile compound according to claim 1 to said arthropod pest or a place where said arthropod pest inhabits.

15. The malononitrile compound according to claim 4, wherein $R^1$ is hydrogen,
- $R^2$ is C1-C5 alkyl optionally substituted with one or more halogen, or hydrogen,
- $R^3$ and $R^4$ each are C1-C5 alkyl optionally substituted with one or more halogen, C2-C5 alkenyl optionally substituted with one or more halogen, or hydrogen,
- $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen,
- $R^{19}$ represents C1-C5 alkyl optionally substituted with one or more halogen, C3-C5 alkynyl optionally substituted with one or more halogen, or hydrogen, and
- $R^{20}$ and $R^{21}$ each represent C1-C5 alkyl optionally substituted with one or more halogen, or hydrogen.

16. The malononitrile compound according to claim 5, wherein $R^1$ is hydrogen,
- $R^2$ is C1-C5 alkyl optionally substituted with one or more halogen, or hydrogen,
- $R^3$ and $R^4$ each are C1-C5 alkyl optionally substituted with one or more halogen, C2-C5 alkenyl optionally substituted with one or more halogen, or hydrogen,
- $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen,
- $R^6$ is C1-C5 alkyl optionally substituted with one or more halogen,
- $R^{19}$ represents C1-C5 alkyl optionally substituted with one or more halogen, C3-C5 alkynyl optionally substituted with one or more halogen, or hydrogen, and
- $R^{20}$ and $R^{21}$ each represent C1-C5 alkyl optionally substituted with one or more halogen, or hydrogen.

17. The malononitrile compound according to claim 6, wherein $R^1$ is hydrogen,
- $R^2$ is C1-C5 alkyl optionally substituted with one or more halogen, or hydrogen,
- $R^3$ and $R^4$ each are C1-C5 alkyl optionally substituted with one or more halogen, C2-C5 alkenyl optionally substituted with one or more halogen, or hydrogen,
- $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen,
- $R^{19}$ represents C1-C5 alkyl optionally substituted with one or more halogen, C3-C5 alkynyl optionally substituted with one or more halogen, or hydrogen, and
- $R^{20}$ and $R^{21}$ each represent C1-C5 alkyl optionally substituted with one or more halogen, or hydrogen.

18. The malononitrile compound according to claim 7, wherein $R^1$ is hydrogen,
- $R^2$ is C1-C5 alkyl optionally substituted with one or more halogen, or hydrogen,
- $R^3$ and $R^4$ each are C1-C5 alkyl optionally substituted with one or more halogen, C2-C5 alkenyl optionally substituted with one or more halogen, or hydrogen,
- $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen,
- $R^{19}$ represents C1-C5 alkyl optionally substituted with one or more halogen, C3-C5 alkynyl optionally substituted with one or more halogen, or hydrogen, and
- $R^{20}$ and $R^{21}$ each represent C1-C5 alkyl optionally substituted with one or more halogen, or hydrogen.

19. The malononitrile compound according to claim 8, wherein $R^1$ is hydrogen,
- $R^2$ is C1-C5 alkyl optionally substituted with one or more halogen, or hydrogen,
- $R^3$ and $R^4$ each are C1-C5 alkyl optionally substituted with one or more halogen, C2-C5 alkenyl optionally substituted with one or more halogen, or hydrogen,
- $R^5$ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen,
- $R^{19}$ represents C1-C5 alkyl optionally substituted with one or more halogen, C3-C5 alkynyl optionally substituted with one or more halogen, or hydrogen, and
- $R^{20}$ and $R^{21}$ each represent C1-C5 alkyl optionally substituted with one or more halogen, or hydrogen.

20. The malononitrile compound according to claim 9, wherein $R^1$ is hydrogen,
- $R^2$ is C1-C5 alkyl optionally substituted with one or more halogen, or hydrogen,
- $R^3$ and $R^4$ each are C1-C5 alkyl optionally substituted with one or more halogen, C2-C5 alkenyl optionally substituted with one or more halogen, or hydrogen, R⁵ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen.

21. The malononitrile compound according to claim 10, wherein $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, R⁵ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen.

22. The malononitrile compound according to claim 11, wherein $R^1$ is hydrogen, $R^2$ is C1-C5 alkyl optionally substituted with one or more halogen, or hydrogen, $R^3$ and $R^4$ each are C1-C5 alkyl optionally substituted with one or more halogen, C2-C5 alkenyl optionally substituted with one or more halogen, or hydrogen, R⁵ is halogen, C1-C5 alkyl optionally substituted with one or more halogen, C3-C6 cycloalkyl optionally substituted with one or more halogen, C1-C5 alkoxy optionally substituted with one or more halogen, C3-C6 alkenyloxy optionally substituted with one or more halogen, C3-C6 alkynyloxy optionally substituted with one or more halogen, C1-C5 alkylthio optionally substituted with one or more halogen, C1-C5 alkylsulfinyl optionally substituted with one or more halogen, C1-C5 alkylsulfonyl optionally substituted with one or more halogen, a group represented by $C(OR^{19})R^{20}R^{21}$, or hydrogen, $R^6$ is C1-C5 alkyl optionally substituted with one or more halogen, $R^{19}$ represents C1-C5 alkyl optionally substituted with one or more halogen, C3-C5 alkynyl optionally substituted with one or more halogen, or hydrogen, and $R^{20}$ and $R^{21}$ each represent C1-C5 alkyl optionally substituted with one or more halogen, or hydrogen.

* * * * *